(12) United States Patent
Wang et al.

(10) Patent No.: US 11,525,006 B2
(45) Date of Patent: Dec. 13, 2022

(54) BCMA-TARGETING ANTIBODY AND USE THEREOF

(71) Applicant: CRAGE medical Co., Limited, Hong Kong (CN)

(72) Inventors: Peng Wang, Shanghai (CN); Huamao Wang, Shanghai (CN); Hua Jiang, Shanghai (CN)

(73) Assignee: CRAGE medical Co., Limited, Hong Kong (CN)

( * ) Notice: Subject to any disclaimer, the term of this patent is extended or adjusted under 35 U.S.C. 154(b) by 489 days.

(21) Appl. No.: 16/479,365

(22) PCT Filed: Jan. 23, 2018

(86) PCT No.: PCT/CN2018/073863
§ 371 (c)(1),
(2) Date: Jul. 19, 2019

(87) PCT Pub. No.: WO2018/133877
PCT Pub. Date: Jul. 26, 2018

(65) Prior Publication Data
US 2019/0359726 A1 Nov. 28, 2019

(30) Foreign Application Priority Data

Jan. 23, 2017 (CN) .......................... 201710058581.8
Sep. 30, 2017 (CN) .......................... 201710920346.7

(51) Int. Cl.
| | | |
|---|---|---|
| C07K 16/28 | (2006.01) |
| A61P 35/00 | (2006.01) |
| C07K 14/725 | (2006.01) |
| C07K 14/705 | (2006.01) |
| C12N 5/0783 | (2010.01) |
| A61K 39/00 | (2006.01) |
| C07K 14/525 | (2006.01) |
| C07K 14/54 | (2006.01) |
| C07K 14/555 | (2006.01) |
| C07K 16/46 | (2006.01) |

(52) U.S. Cl.
CPC .......... *C07K 16/2878* (2013.01); *A61P 35/00* (2018.01); *C07K 14/525* (2013.01); *C07K 14/5434* (2013.01); *C07K 14/5443* (2013.01); *C07K 14/555* (2013.01); *C07K 14/7051* (2013.01); *C07K 14/70517* (2013.01); *C07K 14/70521* (2013.01); *C07K 14/70578* (2013.01); *C07K 16/2809* (2013.01); *C12N 5/0636* (2013.01); *A61K 2039/505* (2013.01); *C07K 16/468* (2013.01); *C07K 2317/526* (2013.01); *C07K 2317/565* (2013.01); *C07K 2317/622* (2013.01); *C07K 2317/73* (2013.01); *C07K 2317/76* (2013.01); *C07K 2317/92* (2013.01); *C07K 2319/02* (2013.01); *C07K 2319/03* (2013.01); *C07K 2319/30* (2013.01); *C07K 2319/33* (2013.01)

(58) Field of Classification Search
CPC .. C07K 16/00–468; C07K 2317/00–94; C07K 14/7051; A61K 35/17; C12N 5/0636
See application file for complete search history.

(56) References Cited

U.S. PATENT DOCUMENTS

| | | | |
|---|---|---|---|
| 10,077,315 B2 * | 9/2018 | Vu ...................... A61K 39/3955 |
| 10,174,095 B2 * | 1/2019 | Brogdon ................ C07K 16/28 |
| 11,084,880 B2 * | 8/2021 | Brogdon ................ A61P 35/02 |
| 2014/0105915 A1 | 4/2014 | Algate et al. |
| 2015/0344583 A1 | 12/2015 | Armitage et al. |
| 2015/0368351 A1 | 12/2015 | Vu et al. |
| 2015/0376287 A1 | 12/2015 | Vu et al. |
| 2021/0292427 A1 * | 9/2021 | Li ...................... C07K 14/7051 |
| 2022/0016166 A1 * | 1/2022 | Li .......................... A61K 35/17 |

FOREIGN PATENT DOCUMENTS

| | | |
|---|---|---|
| CN | 103562225 A | 2/2014 |
| CN | 104968682 A | 10/2015 |
| CN | 104968683 A | 10/2015 |
| CN | 105143263 A | 12/2015 |
| CN | 105777911 A | 7/2016 |
| WO | 2014/122143 A1 | 8/2014 |
| WO | 2015/112900 A1 | 7/2015 |
| WO | 2015/112900 A8 | 7/2015 |
| WO | 2015/117002 A1 | 8/2015 |
| WO | 2015/124297 A1 | 8/2015 |
| WO | 2016/014565 A2 | 1/2016 |
| WO | 2016/014565 A3 | 1/2016 |
| WO | 2016/090327 A2 | 6/2016 |
| WO | 2016/090327 A3 | 6/2016 |
| WO | 2019/052562 A1 | 3/2019 |
| WO | WO-2020020210 A1 * | 1/2020 ........... A61K 31/675 |
| WO | WO-2020057666 A1 * | 3/2020 ......... A61K 39/0011 |
| WO | WO-2020259707 A1 * | 12/2020 |

OTHER PUBLICATIONS

Ali et al., Blood 128(13):1688-1700 (Year: 2016).*
Priority document CN20170833528.0, filed Sep. 15, 2017, for PCT/CN2018/106034. (Year: 2017).*
Extended European Search Report corresponding to EP Appl 18741764.7 dated Mar. 26, 2021; 13 pages.
English Translation of the International Search Report corresponding to PCT/CN2018/073863 dated Apr. 25, 2018; 10 pages.

* cited by examiner

*Primary Examiner* — Jessica H Roark
(74) *Attorney, Agent, or Firm* — Mintz Levin Cohn Ferris Glovsky and Popeo, P.C.

(57) ABSTRACT

Provided in the present invention are a specific antibody of BCMA and a BCMA-targeting immune effector cell, and also provided are a chimeric antigen receptor-modified T cell prepared using the antibody and the use thereof.

24 Claims, 12 Drawing Sheets
Specification includes a Sequence Listing.

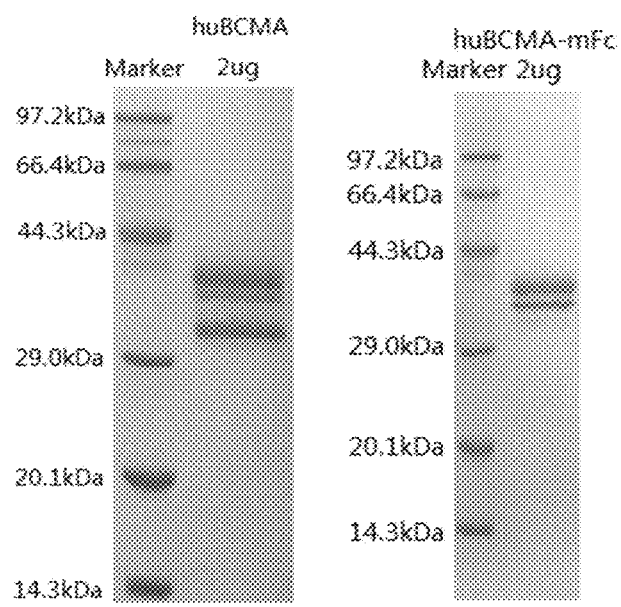
Fig. 1
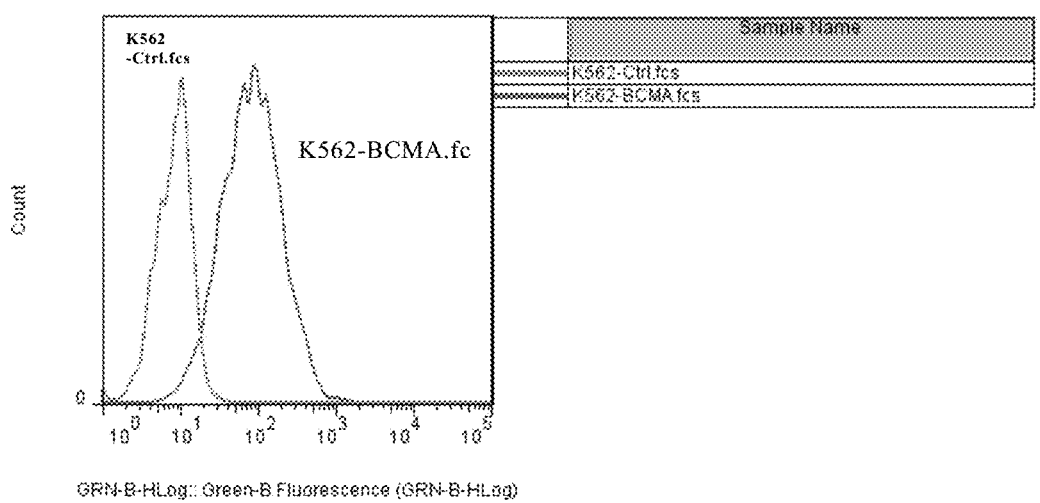
Fig. 2-A

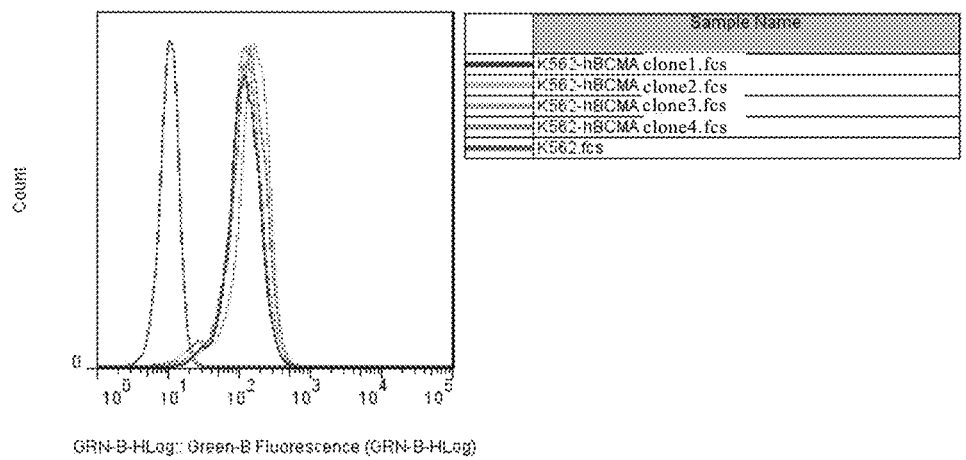
Fig. 2-B
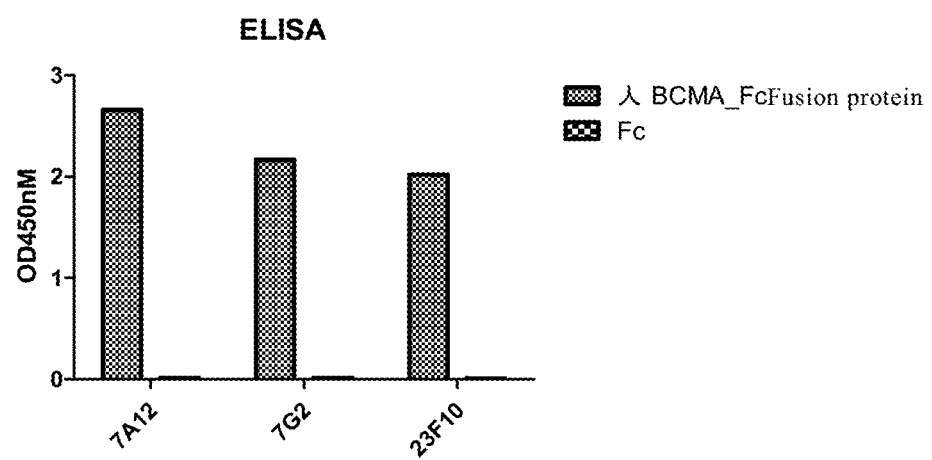
Fig. 3

SEQUENCE LISTING

<160> NUMBER OF SEQ ID NOS: 87

<210> SEQ ID NO 1
<211> LENGTH: 5
<212> TYPE: PRT
<213> ORGANISM: Artificial sequence

<220> FEATURE:
<223> OTHER INFORMATION: 7A12, 7G2, 23F10 HCDR1

<400> SEQUENCE: 1

Ser Tyr Ala Met Ser
1               5

<210> SEQ ID NO 2
<211> LENGTH: 17
<212> TYPE: PRT
<213> ORGANISM: Artificial sequence
<220> FEATURE:
<223> OTHER INFORMATION: 7A12, 7G2, 23F10 HCDR1

<400> SEQUENCE: 2

Ala Ile Ser Gly Ser Gly Gly Ser Thr Tyr Tyr Ala Asp Ser Val Lys
1               5                   10                  15

Gly

<210> SEQ ID NO 3
<211> LENGTH: 8
<212> TYPE: PRT
<213> ORGANISM: Artificial sequence
<220> FEATURE:
<223> OTHER INFORMATION: 7A12 HCDR3

<400> SEQUENCE: 3

Tyr Pro Tyr Leu Ala Phe Asp Tyr
1               5

<210> SEQ ID NO 4
<211> LENGTH: 9
<212> TYPE: PRT
<213> ORGANISM: Artificial sequence
<220> FEATURE:
<223> OTHER INFORMATION: 7G2 HCDR3

<400> SEQUENCE: 4

Leu Ser Gly Asp Ala Ala Met Asp Tyr
1               5

<210> SEQ ID NO 5
<211> LENGTH: 10
<212> TYPE: PRT
<213> ORGANISM: Artificial sequence
<220> FEATURE:
<223> OTHER INFORMATION: 23F10 HCDR3

<400> SEQUENCE: 5

Val Arg Pro Phe Trp Gly Thr Phe Asp Tyr
1               5                   10

<210> SEQ ID NO 6
<211> LENGTH: 12
<212> TYPE: PRT
<213> ORGANISM: Artificial sequence
<220> FEATURE:
<223> OTHER INFORMATION: 7A12, 7G2, 23F10 LCDR1

<400> SEQUENCE: 6

Arg Ala Ser Gln Ser Val Ser Ser Ser Tyr Leu Ala
1               5                   10

```
<210> SEQ ID NO 7
<211> LENGTH: 7
<212> TYPE: PRT
<213> ORGANISM: Artificial sequence
<220> FEATURE:
<223> OTHER INFORMATION: 7A12, 7G2, 23F10 LCDR2

<400> SEQUENCE: 7

Gly Ala Ser Ser Arg Ala Thr
1               5

<210> SEQ ID NO 8
<211> LENGTH: 9
<212> TYPE: PRT
<213> ORGANISM: Artificial sequence
<220> FEATURE:
<223> OTHER INFORMATION: 7A12 LCDR3

<400> SEQUENCE: 8

Gln Gln Tyr Gly Tyr Pro Pro Ser Tyr
1               5

<210> SEQ ID NO 9
<211> LENGTH: 9
<212> TYPE: PRT
<213> ORGANISM: Artificial sequence
<220> FEATURE:
<223> OTHER INFORMATION: 7G2 LCDR3

<400> SEQUENCE: 9

Gln Gln Tyr Gly Tyr Pro Pro Arg Tyr
1               5

<210> SEQ ID NO 10
<211> LENGTH: 9
<212> TYPE: PRT
<213> ORGANISM: Artificial sequence
<220> FEATURE:
<223> OTHER INFORMATION: 23F10 LCDR3

<400> SEQUENCE: 10

Gln Gln Tyr Phe Asn Pro Pro Glu Tyr
1               5

<210> SEQ ID NO 11
<211> LENGTH: 109
<212> TYPE: PRT
<213> ORGANISM: Artificial sequence
<220> FEATURE:
<223> OTHER INFORMATION: Amino acid sequence of 7A12 light chain
      variable regoin

<400> SEQUENCE: 11

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln Tyr Gly Tyr Pro Pro
            85                  90                  95

Ser Tyr Thr Phe Gly Gln Gly Thr Lys Val Glu Ile Lys
            100                 105

<210> SEQ ID NO 12
<211> LENGTH: 327
<212> TYPE: DNA
<213> ORGANISM: Artificial sequence
<220> FEATURE:
<223> OTHER INFORMATION: Nucleotide sequence of 7A12 light chain
      variable region

<400> SEQUENCE: 12
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtacggtt acccaccatc ttacacgttc     300
ggccagggga ccaaagtgga aatcaaa                                          327

<210> SEQ ID NO 13
<211> LENGTH: 117
<212> TYPE: PRT
<213> ORGANISM: Artificial sequence
<220> FEATURE:
<223> OTHER INFORMATION: Amino acid sequence of 7A12 heavy chain
      variable region

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Leu Ala Phe Asp Tyr Trp Gly Gln Gly Thr Leu
            100                 105                 110

Val Thr Val Ser Ser
        115

<210> SEQ ID NO 14
<211> LENGTH: 351
<212> TYPE: DNA
<213> ORGANISM: Artificial sequence
<220> FEATURE:
<223> OTHER INFORMATION: Nucleotide sequence of 7A12 heavy chain
      variable region

<400> SEQUENCE: 14
gaggtgcaat tgctggagtc tgggggaggc ttggtacagc ctgggggtc cctgagactc       60 tcctgtgcag cctccggatt cacctttagc agttatgcca tgagctgggt ccgccaggct     120

```
ccagggaagg ggctggagtg ggtctcagct attagtggta gtggtggtag cacatactac      180
gcagactccg tgaagggccg gttcaccatc tccagagaca attccaagaa cacgctgtat      240
ctgcagatga acagcctgag agccgaggac acggccgtat attactgtgc gcgttaccca      300
tacctggcat tcgactactg gggccaagga accctggtca ccgtctcgag t              351
```

<210> SEQ ID NO 15
<211> LENGTH: 109
<212> TYPE: PRT
<213> ORGANISM: Artificial sequence
<220> FEATURE:
<223> OTHER INFORMATION: Amino acid sequence of 7G2 light chain
      variable region

<400> SEQUENCE: 15

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Tyr Pro Pro
                85                  90                  95

Arg Tyr Thr Phe Gly Gln Gly Thr Lys Val Glu Ile Lys
            100                 105
```

<210> SEQ ID NO 16
<211> LENGTH: 327
<212> TYPE: DNA
<213> ORGANISM: Artificial sequence
<220> FEATURE:
<223> OTHER INFORMATION: Nucleotide sequence of 7G2 light variable
      region

<400> SEQUENCE: 16

```
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtacggtt acccaccaag atacacgttc     300
ggccagggga ccaaagtgga aatcaaa                                         327
```

<210> SEQ ID NO 17
<211> LENGTH: 118
<212> TYPE: PRT
<213> ORGANISM: Artificial sequence
<220> FEATURE:
<223> OTHER INFORMATION: Amino acid sequence of 7G2 heavy chain variable
      region

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Ser Gly Asp Ala Ala Met Asp Tyr Trp Gly Gln Gly Thr
             100                 105                 110

Leu Val Thr Val Ser Ser
             115
```

<210> SEQ ID NO 18
<211> LENGTH: 354
<212> TYPE: DNA
<213> ORGANISM: Artificial sequence
<220> FEATURE:
<223> OTHER INFORMATION: Nucleotide sequence of 7G2 heavy chain variable
      region

<400> SEQUENCE: 18

```
gaggtgcaat tgctggagtc tgggggaggc ttggtacagc ctggggggtc cctgagactc      60
tcctgtgcag cctccggatt cacctttagc agttatgcca tgagctgggt ccgccaggct     120
ccagggaagg gctggagtg gtctcagct attagtggta gtggtggtag cacatactac      180
gcagactccg tgaagggccg gttcaccatc tccagagaca attccaagaa cacgctgtat     240
ctgcagatga acagcctgag agccgaggac acggccgtat attactgtgc gaaactgtct     300
ggtgatgcag caatggacta ctggggccaa ggaaccctgg tcaccgtctc gagt           354
```

<210> SEQ ID NO 19
<211> LENGTH: 109
<212> TYPE: PRT
<213> ORGANISM: Artificial sequence
<220> FEATURE:
<223> OTHER INFORMATION: Amino acid sequence of 23F10 light chain
      variable region

<400> SEQUENCE: 19

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Phe Asn Pro Pro
                 85                  90                  95

Glu Tyr Thr Phe Gly Gln Gly Thr Lys Val Glu Ile Lys
             100                 105
```

<210> SEQ ID NO 20
<211> LENGTH: 327
<212> TYPE: DNA
<213> ORGANISM: Artificial sequence

```
<220> FEATURE:
<223> OTHER INFORMATION: Nucleotide sequence of 23F10 light chain
      variable region

<400> SEQUENCE: 20
gaaatcgtgt taacgcagtc tccaggcacc ctgtctttgt ctccagggga aagagccacc      60
ctctcttgca gggccagtca gagtgttagc agcagctact tagcctggta ccagcagaaa     120
cctggccagg ctcccaggct cctcatctat ggagcatcca gcagggccac tggcatccca     180
gacaggttca gtggcagtgg atccgggaca gacttcactc tcaccatcag cagactggag     240
cctgaagatt ttgcagtgta ttactgtcag cagtacttca acccaccaga atacacgttc     300
ggccagggga ccaaagtgga aatcaaa                                         327

<210> SEQ ID NO 21
<211> LENGTH: 119
<212> TYPE: PRT
<213> ORGANISM: Artificial sequence
<220> FEATURE:
<223> OTHER INFORMATION: Amino acid sequence of 23F10 heavy chain
      variable region

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Pro Phe Trp Gly Thr Phe Asp Tyr Trp Gly Gln Gly
            100                 105                 110

Thr Leu Val Thr Val Ser Ser
        115

<210> SEQ ID NO 22
<211> LENGTH: 357
<212> TYPE: DNA
<213> ORGANISM: Artificial sequence
<220> FEATURE:
<223> OTHER INFORMATION: Nucleotide sequence of 23F10 heavy chain
      variable region

<400> SEQUENCE: 22
gaggtgcaat tgctggagtc tgggggaggc ttggtacagc ctggggggtc cctgagactc      60
tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gaaagttcgt     300
ccattctggg gtactttcga ctactggggc caaggaaccc tggtcaccgt ctcgagt        357
```

<210> SEQ ID NO 23
<211> LENGTH: 21
<212> TYPE: PRT
<213> ORGANISM: Artificial sequence
<220> FEATURE:
<223> OTHER INFORMATION: Amino acid sequence of CD8alpha signal peptide

<400> SEQUENCE: 23

Met Ala Leu Pro Val Thr Ala Leu Leu Leu Pro Leu Ala Leu Leu Leu
1               5                   10                  15

His Ala Ala Arg Pro
            20

<210> SEQ ID NO 24
<211> LENGTH: 63
<212> TYPE: DNA
<213> ORGANISM: Artificial sequence
<220> FEATURE:
<223> OTHER INFORMATION: Nucleotide sequence of CD8alpha signal peptide

<400> SEQUENCE: 24
atggccttac cagtgaccgc cttgctcctg ccgctggcct tgctgctcca cgccgccagg     60
ccg                                                                  63

<210> SEQ ID NO 25
<211> LENGTH: 45
<212> TYPE: PRT
<213> ORGANISM: Artificial sequence
<220> FEATURE:
<223> OTHER INFORMATION: Amino acid sequence of CD8 hinge

<400> SEQUENCE: 25

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 26
<211> LENGTH: 135
<212> TYPE: DNA
<213> ORGANISM: Artificial sequence
<220> FEATURE:
<223> OTHER INFORMATION: Nucleotide sequence of CD8 hinge

<400> SEQUENCE: 26
accacgacgc cagcgccgcg accaccaaca ccggcgccca ccatcgcgtc gcagcccctg     60
tccctgcgcc cagaggcgtg ccggccagcg gcggggggcg cagtgcacac gagggggctg    120
gacttcgcct gtgat                                                    135

<210> SEQ ID NO 27
<211> LENGTH: 27
<212> TYPE: PRT
<213> ORGANISM: Artificial sequence
<220> FEATURE:
<223> OTHER INFORMATION: Amino acid sequence of CD28 transmembrane
      region -continued

<400> SEQUENCE: 27

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 28
<211> LENGTH: 81
<212> TYPE: DNA
<213> ORGANISM: Artificial sequence
<220> FEATURE:
<223> OTHER INFORMATION: Nucleotide sequence of CD28 transmembrane
      region

<400> SEQUENCE: 28
ttttgggtgc tggtggtggt tggtggagtc ctggcttgct atagcttgct agtaacagtg     60
gcctttatta ttttctgggt g                                              81

<210> SEQ ID NO 29
<211> LENGTH: 41
<212> TYPE: PRT
<213> ORGANISM: Artificial sequence
<220> FEATURE:
<223> OTHER INFORMATION: Amino acid sequence of CD28 intracellular
      region

<400> SEQUENCE: 29

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 30
<211> LENGTH: 123
<212> TYPE: DNA
<213> ORGANISM: Artificial sequence
<220> FEATURE:
<223> OTHER INFORMATION: Nucleotide sequence of CD28 intracellular
      region

<400> SEQUENCE: 30
aggagtaaga ggagcaggct cctgcacagt gactacatga acatgactcc ccgccgcccc     60
gggccaaccc gcaagcatta ccagccctat gccccaccac gcgacttcgc agcctatcgc    120
tcc                                                                  123

<210> SEQ ID NO 31
<211> LENGTH: 113
<212> TYPE: PRT
<213> ORGANISM: Artificial sequence
<220> FEATURE:
<223> OTHER INFORMATION: Amino acid sequence of CD3Z domain

<400> SEQUENCE: 31

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 32
<211> LENGTH: 339
<212> TYPE: DNA
<213> ORGANISM: Artificial sequence
<220> FEATURE:
<223> OTHER INFORMATION: Nucleotide sequence of CD3Z domain

<400> SEQUENCE: 32
agagtgaagt tcagcaggag cgcagacgcc cccgcgtacc agcagggcca gaaccagctc      60
tataacgagc tcaatctagg acgaagagag gagtacgatg tttgggacaa gagacgtggc     120 cgggacctg agatggggg aaagccgcag agaaggaaga accctcagga aggcctgtac       180
aatgaactgc agaaagataa gatggcggag gcctacagtg agattgggat gaaaggcgag     240
cgccggaggg gcaaggggca cgatggcctt taccagggtc tcagtacagc caccaaggac     300
acctacgacg cccttcacat gcaggccctg ccccctcgc                             339

<210> SEQ ID NO 33
<211> LENGTH: 21
<212> TYPE: PRT
<213> ORGANISM: Artificial sequence
<220> FEATURE:
<223> OTHER INFORMATION: Amino acid sequence of CD8 transmembrane region

<400> SEQUENCE: 33

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 34
<211> LENGTH: 63
<212> TYPE: DNA
<213> ORGANISM: Artificial sequence
<220> FEATURE:
<223> OTHER INFORMATION: Nucleotide sequence of CD8 transmembrane region

<400> SEQUENCE: 34
atctacatct gggcgccctt ggccgggact tgtgggtcc ttctcctgtc actggttatc       60
acc                                                                    63

<210> SEQ ID NO 35
<211> LENGTH: 42
<212> TYPE: PRT
<213> ORGANISM: Artificial sequence
<220> FEATURE:
<223> OTHER INFORMATION: Amino acid sequence of CD137 intracellular
      region

<400> SEQUENCE: 35

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 36
<211> LENGTH: 126
<212> TYPE: DNA
<213> ORGANISM: Artificial sequence
<220> FEATURE:
<223> OTHER INFORMATION: Nucleotide sequence of CD137 intracellular
      region

<400> SEQUENCE: 36
aaacggggca gaaagaaact cctgtatata ttcaaacaac catttatgag accagtacaa        60
actactcaag aggaagatgg ctgtagctgc cgatttccag aagaagaaga aggaggatgt       120
gaactg                                                                 126

<210> SEQ ID NO 37
<211> LENGTH: 184
<212> TYPE: PRT
<213> ORGANISM: Artificial sequence
<220> FEATURE:
<223> OTHER INFORMATION: BCMA amino acid sequence

<400> SEQUENCE: 37

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 38
<211> LENGTH: 54
<212> TYPE: PRT
<213> ORGANISM: Artificial sequence
<220> FEATURE:
<223> OTHER INFORMATION: Human BCMA extracellular segment Met1-Ala54

<400> SEQUENCE: 38

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50

<210> SEQ ID NO 39
<211> LENGTH: 162
<212> TYPE: DNA
<213> ORGANISM: Artificial sequence
<220> FEATURE:
<223> OTHER INFORMATION: Nucleotide sequence of human BCMA extracellular
      segment Met1-Ala54

<400> SEQUENCE: 39
atgctgcaga tggccggcca gtgcagccag aacgagtact tcgacagcct gctgcacgcc      60
tgcatcccct gccagctgcg gtgcagcagc aacacccccc ccctgacctg ccagcggtac     120
tgcaacgcca gcgtgaccaa cagcgtgaag ggcaccaacg cc                        162

<210> SEQ ID NO 40
<211> LENGTH: 283
<212> TYPE: PRT
<213> ORGANISM: Artificial sequence
<220> FEATURE:
<223> OTHER INFORMATION: BCMA_huFc

<400> SEQUENCE: 40

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Gly Ser Asp Lys Thr His Thr Cys Pro Pro
    50                  55                  60

Cys Pro Ala Pro Glu Leu Leu Gly Gly Pro Ser Val Phe Leu Phe Pro
65                  70                  75                  80

Pro Lys Pro Lys Asp Thr Leu Met Ile Ser Arg Thr Pro Glu Val Thr
            85                  90                  95

Cys Val Val Val Asp Val Ser His Glu Asp Pro Glu Val Lys Phe Asn
        100                 105                 110

Trp Tyr Val Asp Gly Val Glu Val His Asn Ala Lys Thr Lys Pro Arg
    115                 120                 125

Glu Glu Gln Tyr Asn Ser Thr Tyr Arg Val Val Ser Val Leu Thr Val
130                 135                 140

Leu His Gln Asp Trp Leu Asn Gly Lys Glu Tyr Lys Cys Lys Val Ser
145                 150                 155                 160

Asn Lys Ala Leu Pro Ala Pro Ile Glu Lys Thr Ile Ser Lys Ala Lys
                165                 170                 175

Gly Gln Pro Arg Glu Pro Gln Val Tyr Thr Leu Pro Pro Ser Arg Asp
            180                 185                 190

```
Glu Leu Thr Lys Asn Gln Val Ser Leu Trp Cys Leu Val Lys Gly Phe
        195                 200                 205

Tyr Pro Ser Asp Ile Ala Val Glu Trp Glu Ser Asn Gly Gln Pro Glu
    210                 215                 220

Asn Asn Tyr Lys Thr Thr Pro Pro Val Leu Asp Ser Asp Gly Ser Phe
225                 230                 235                 240

Phe Leu Tyr Ser Lys Leu Thr Val Asp Lys Ser Arg Trp Gln Gln Gly
                245                 250                 255

Asn Val Phe Ser Cys Ser Val Met His Glu Ala Leu His Asn His Tyr
            260                 265                 270

Thr Gln Lys Ser Leu Ser Leu Ser Pro Gly Lys
        275                 280

<210> SEQ ID NO 41
<211> LENGTH: 849
<212> TYPE: DNA
<213> ORGANISM: Artificial sequence
<220> FEATURE:
<223> OTHER INFORMATION: Nucleotide sequence of BCMA_huFc

<400> SEQUENCE: 41
atgctgcaga tggccggcca gtgcagccag aacgagtact tcgacagcct gctgcacgcc      60
tgcatcccct gccagctgcg gtgcagcagc aacaccccccc ccctgacctg ccagcggtac     120
tgcaacgcca gcgtgaccaa cagcgtgaag ggcaccaacg ccggatccga caaaactcac     180
acatgcccac cgtgcccagc acctgaactc ctggggggac cgtcagtctt cctcttcccc     240
ccaaaaccca aggacaccct catgatctcc cggacccctg aggtcacatg cgtggtggtg     300
gacgtgagcc acgaagaccc tgaggtcaag ttcaactggt acgtggacgg cgtggaggtg     360
cataatgcca agacaaagcc gcgggaggag cagtacaaca gcacgtaccg tgtggtcagc     420
gtcctcaccg tcctgcacca ggactggctg aatggcaagg agtacaagtg caaggtctcc     480
aacaaagccc tcccagcccc catcgagaaa accatctcca aagccaaagg cagccccga      540 gaaccacagg tgtacaccct gcccccatcc cgggatgagc tgaccaagaa ccaggtcagc     600
ctgtggtgcc tggtcaaagg cttctatccc agcgacatcg ccgtggagtg ggagagcaat     660
gggcagccgg agaacaacta caagaccacg cctcccgtgc tggactccga cggctccttc     720
ttcctctata gcaagctcac cgtggacaag agcaggtggc agcaggggaa cgtcttctca     780
tgctccgtga tgcatgaggc tctgcacaac cactacacgc agaagagcct ctccctgtct     840
ccgggtaaa                                                              849

<210> SEQ ID NO 42
<211> LENGTH: 281
<212> TYPE: PRT
<213> ORGANISM: Artificial sequence
<220> FEATURE:
<223> OTHER INFORMATION: BCMA_muFc

<400> SEQUENCE: 42

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Gly Ser Arg Asp Cys Gly Cys Lys Pro Cys
    50                  55                  60
```

```
Ile Cys Thr Val Pro Glu Val Ser Ser Val Phe Ile Phe Pro Pro Lys
 65                  70                  75                  80

Pro Lys Asp Val Leu Thr Ile Thr Leu Thr Pro Lys Val Thr Cys Val
                 85                  90                  95

Val Val Asp Ile Ser Lys Asp Asp Pro Glu Val Gln Phe Ser Trp Phe
            100                 105                 110

Val Asp Asp Val Glu Val His Thr Ala Gln Thr Gln Pro Arg Glu Glu
        115                 120                 125

Gln Phe Asn Ser Thr Phe Arg Ser Val Ser Glu Leu Pro Ile Met His
    130                 135                 140

Gln Asp Trp Leu Asn Gly Lys Glu Phe Lys Cys Arg Val Asn Ser Ala
145                 150                 155                 160

Ala Phe Pro Ala Pro Ile Glu Lys Thr Ile Ser Lys Thr Lys Gly Arg
                165                 170                 175

Pro Lys Ala Pro Gln Val Tyr Thr Ile Pro Pro Pro Lys Glu Gln Met
            180                 185                 190

Ala Lys Asp Lys Val Ser Leu Thr Cys Met Ile Thr Asp Phe Phe Pro
        195                 200                 205

Glu Asp Ile Thr Val Glu Trp Gln Trp Asn Gly Gln Pro Ala Glu Asn
    210                 215                 220

Tyr Lys Asn Thr Gln Pro Ile Met Asp Thr Asp Gly Ser Tyr Phe Val
225                 230                 235                 240

Tyr Ser Lys Leu Asn Val Gln Lys Ser Asn Trp Glu Ala Gly Asn Thr
                245                 250                 255

Phe Thr Cys Ser Val Leu His Glu Gly Leu His Asn His His Thr Glu
            260                 265                 270

Lys Ser Leu Ser His Ser Pro Gly Lys
        275                 280
```

<210> SEQ ID NO 43
<211> LENGTH: 843
<212> TYPE: DNA
<213> ORGANISM: Artificial sequence
<220> FEATURE:
<223> OTHER INFORMATION: Nucleotide sequence of BCMA_muFc

<400> SEQUENCE: 43

```
atgctgcaga tggccggcca gtgcagccag aacgagtact cgacagcct gctgcacgcc      60 tgcatcccct gccagctgcg gtgcagcagc aacacccccc ccctgacctg ccagcggtac     120
tgcaacgcca gcgtgaccaa cagcgtgaag ggcaccaacg ccggatccag ggattgtggt     180
tgtaagcctt gcatatgtac agtcccagaa gtatcatctg tcttcatctt ccccccaaag     240
cccaaggatg tgctcaccat tactctgact cctaaggtca cgtgtgttgt ggtagacatc     300
agcaaggatg atcccgaggt ccagttcagc tggtttgtag atgatgtgga ggtgcacaca     360
gctcagacgc aaccccggga ggagcagttc aacagcactt tccgctcagt cagtgaactt     420
cccatcatgc accaggactg gctcaatggc aaggagttca atgcagggt caacagtgca      480 gctttccctg cccccatcga gaaaaccatc tccaaaacca aggcagacc gaaggctcca     540 caggtgtaca ccattccacc tcccaaggag cagatggcca aggataaagt cagtctgacc     600
tgcatgataa cagacttctt ccctgaagac attactgtgg agtggcagtg gaatgggcag     660
ccagcggaga actacaagaa cactcagccc atcatggaca cagatggctc ttacttcgtc     720
tacagcaagc tcaatgtgca gaagagcaac tgggaggcag gaaatacttt cacctgctct     780
```

```
gtgttacatg agggcctgca caaccaccat actgagaaga gcctctccca ctctcctggt    840
aaa                                                                  843

<210> SEQ ID NO 44
<211> LENGTH: 589
<212> TYPE: DNA
<213> ORGANISM: Artificial sequence
<220> FEATURE:
<223> OTHER INFORMATION: Nucleotide sequence of human BCMA with
      introduced restriction sites MluI, SalI

<400> SEQUENCE: 44
acgcgtccta gcgctaccgg tcgccaccat gttgcagatg gctgggcagt gctcccaaaa     60
tgaatatttt gacagtttgt tgcatgcttg cataccttgt caacttcgat gttcttctaa    120
tactcctcct ctaacatgtc agcgttattg taatgcaagt gtgaccaatt cagtgaaagg    180
aacgaatgcg attctctgga cctgtttggg actgagctta ataatttctt tggcagtttt    240
cgtgctaatt ttttttgctaa ggaagataaa ctctgaacca ttaaaggacg agtttaaaaa    300
cacaggatca ggtctcctgg gcatggctaa cattgacctg gaaaagagca ggactggtga    360
tgaaattatt cttccgagag gcctcgagta cacggtggaa gaatgcacct gtgaagactg    420
catcaagagc aaaccgaagg tcgactctga ccattgcttt ccactcccag ctatggagga    480
aggcgcaacc attcttgtca ccacgaaaac gaatgactat tgcaagagcc tgccagctgc    540
tttgagtgct acggagatag agaaatcaat ttctgctagg taagtcgac               589

<210> SEQ ID NO 45
<211> LENGTH: 365
<212> TYPE: PRT
<213> ORGANISM: Artificial sequence
<220> FEATURE:
<223> OTHER INFORMATION: APRIL_huFc

<400> SEQUENCE: 45

His Ser Val Leu His Leu Val Pro Ile Asn Ala Thr Ser Lys Asp Asp
1               5                   10                  15

Ser Asp Val Thr Glu Val Met Trp Gln Pro Ala Leu Arg Arg Gly Arg
            20                  25                  30

Gly Leu Gln Ala Gln Gly Tyr Gly Val Arg Ile Gln Asp Ala Gly Val
        35                  40                  45

Tyr Leu Leu Tyr Ser Gln Val Leu Phe Gln Asp Val Thr Phe Thr Met
    50                  55                  60

Gly Gln Val Val Ser Arg Glu Gly Gln Gly Arg Gln Glu Thr Leu Phe
65                  70                  75                  80

Arg Cys Ile Arg Ser Met Pro Ser His Pro Asp Arg Ala Tyr Asn Ser
                85                  90                  95

Cys Tyr Ser Ala Gly Val Phe His Leu His Gln Gly Asp Ile Leu Ser
            100                 105                 110

Val Ile Ile Pro Arg Ala Arg Ala Lys Leu Asn Leu Ser Pro His Gly
        115                 120                 125

Thr Phe Leu Gly Phe Val Lys Leu Gly Ser Asp Lys Thr His Thr Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175
```

| | | | | | | | | | | |
|---|---|---|---|---|---|---|---|---|---|---|
|Val|Thr|Cys|Val|Val|Asp|Val|Ser|His|Glu|Asp|Pro|Glu|Val|Lys|
| | |180| | | |185| | | |190|

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Trp Cys Leu Val Lys
        275                 280                 285

Gly Phe Tyr Pro Ser Asp Ile Ala Val Glu Trp Glu Ser Asn Gly Gln
        290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365

<210> SEQ ID NO 46
<211> LENGTH: 1095
<212> TYPE: DNA
<213> ORGANISM: Artificial sequence
<220> FEATURE:
<223> OTHER INFORMATION: Nucleotide sequence of APRIL_huFc

<400> SEQUENCE: 46

```
cacagcgtgc tgcacctggt gcccatcaac gccaccagca aggacgacag cgacgtgacc    60
gaggtgatgt ggcagcccgc cctgcggcgg ggccggggcc tgcaggccca gggctacggc   120
gtgcggatcc aggacgccgg cgtgtacctg ctgtacagcc aggtgctgtt ccaggacgtg   180
accttcacca tgggccaggt ggtgagccgg gagggccagg ccggcagga gaccctgttc   240
cggtgcatcc ggagcatgcc cagccacccc gaccgggcct acaacagctg ctacagcgcc   300
ggcgtgttcc acctgcacca gggcgacatc ctgagcgtga tcatccccg ggcccgggcc   360
aagctgaacc tgagccccca cggcaccttc ctgggcttcg tgaagctggg atccgacaaa   420
actcacacat gcccaccgtg cccagcacct gaactcctgg ggggaccgtc agtcttcctc   480
ttccccccaa aacccaagga caccctcatg atctcccgga cccctgaggt cacatgcgtg   540
gtggtggacg tgagccacga agaccctgag gtcaagttca actggtacgt ggacggcgtg   600
gaggtgcata atgccaagac aaagccgcgg gaggagcagt acaacagcac gtaccgtgtg   660
gtcagcgtcc tcaccgtcct gcaccaggac tggctgaatg gcaaggagta caagtgcaag   720
gtctccaaca aagccctccc agcccccatc gagaaaacca tctccaaagc caaagggcag   780
ccccgagaac cacaggtgta caccctgccc ccatcccggg atgagctgac caagaaccag   840
gtcagcctgt ggtgcctggt caaaggcttc tatcccagcg acatcgccgt ggagtgggag   900
agcaatgggc agccggagaa caactacaag accacgcctc ccgtgctgga ctccgacggc   960
tccttcttcc tctatagcaa gctcaccgtg gacaagagca ggtggcagca ggggaacgtc  1020
```

```
ttctcatgct ccgtgatgca tgaggctctg cacaaccact acacgcagaa gagcctctcc   1080
ctgtctccgg gtaaa                                                    1095
```

<210> SEQ ID NO 47
<211> LENGTH: 242
<212> TYPE: PRT
<213> ORGANISM: Artificial sequence
<220> FEATURE:
<223> OTHER INFORMATION: 47 7A12 scFv

<400> SEQUENCE: 47

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Leu Ala Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Ser Ser Tyr Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Tyr
    210                 215                 220

Gly Tyr Pro Pro Ser Tyr Thr Phe Gly Gln Gly Thr Lys Val Glu Ile
225                 230                 235                 240

Lys Arg
```

<210> SEQ ID NO 48
<211> LENGTH: 243
<212> TYPE: PRT
<213> ORGANISM: Artificial sequence
<220> FEATURE:
<223> OTHER INFORMATION: 7G2 scFv

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Ser Gly Asp Ala Ala Met Asp Tyr Trp Gly Gln Gly Thr
            100                 105                 110

Leu Val Thr Val Ser Ser Gly Gly Gly Ser Gly Gly Gly Ser
        115                 120                 125

Gly Gly Gly Gly Ser Glu Ile Val Leu Thr Gln Ser Pro Gly Thr Leu
130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Lys Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
195                 200                 205

Ile Ser Arg Leu Glu Pro Glu Asp Phe Ala Val Tyr Tyr Cys Gln Gln
210                 215                 220

Tyr Gly Tyr Pro Pro Arg Tyr Thr Phe Gly Gln Gly Thr Lys Val Glu
225                 230                 235                 240

Ile Lys Arg

<210> SEQ ID NO 49
<211> LENGTH: 26
<212> TYPE: DNA
<213> ORGANISM: Artificial sequence
<220> FEATURE:
<223> OTHER INFORMATION: Primer LMF

<400> SEQUENCE: 49
caggaaacag ctatgaccat gattac                                          26

<210> SEQ ID NO 50
<211> LENGTH: 80
<212> TYPE: DNA
<213> ORGANISM: Artificial sequence
<220> FEATURE:
<223> OTHER INFORMATION: Primer BH1R
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

```
<220> FEATURE:
<221> NAME/KEY: misc_feature
<222> LOCATION: (59)..(60)
<223> OTHER INFORMATION: n is a, c, g, or t

<400> SEQUENCE: 50
tgagacccac tccagcccct tccctggagc ctggcggacc camnmnnmn nmnnmnnmnn        60 aaaggtgaat ccggaggctg                                                    80

<210> SEQ ID NO 51
<211> LENGTH: 67
<212> TYPE: DNA
<213> ORGANISM: Artificial sequence
<220> FEATURE:
<223> OTHER INFORMATION: Primer BH2F
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 51
ggctggagtg ggtctcannk attnnknnkn nknnkggtnn kacannktac gcagactccg        60
tgaaggg                                                                   67

<210> SEQ ID NO 52
<211> LENGTH: 30
<212> TYPE: DNA
<213> ORGANISM: Artificial sequence
<220> FEATURE:
<223> OTHER INFORMATION: Primer FdR

<400> SEQUENCE: 52
gacgttagta aatgaatttt ctgtatgagg                                          30

<210> SEQ ID NO 53
<211> LENGTH: 85
<212> TYPE: DNA
<213> ORGANISM: Artificial sequence
<220> FEATURE:
<223> OTHER INFORMATION: Primer BL1R
<220> FEATURE:
<221> NAME/KEY: misc_feature
<222> LOCATION: (44)..(45)
<223> OTHER INFORMATION: n is a, c, g, or t
```

<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t

<400> SEQUENCE: 53
gatgaggagc ctgggagcct ggccaggttt ctgctggtac camnntaamn nmnnmnnmnn    60
mnnmnnctga ctggccctgc aagag                                         85

<210> SEQ ID NO 54
<211> LENGTH: 58
<212> TYPE: DNA
<213> ORGANISM: Artificial sequence
<220> FEATURE:
<223> OTHER INFORMATION: Primer BL2F
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 54
ccaggctccc aggctcctca tcnnknnknn knnknnkagg gccactggca tcccagac     58

<210> SEQ ID NO 55
<211> LENGTH: 244
<212> TYPE: PRT
<213> ORGANISM: Artificial sequence
<220> FEATURE:
<223> OTHER INFORMATION: 23F10 scFv

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Arg Pro Phe Trp Gly Thr Phe Asp Tyr Trp Gly Gln Gly
            100                 105                 110

Thr Leu Val Thr Val Ser Ser Gly Gly Gly Ser Gly Gly Gly
            115                 120                 125

Ser Gly Gly Gly Ser Glu Ile Val Leu Thr Gln Ser Pro Gly Thr
130                 135                 140

Leu Ser Leu Ser Pro Gly Glu Arg Ala Thr Leu Ser Cys Arg Ala Ser
145                 150                 155                 160

Gln Ser Val Ser Ser Tyr Leu Ala Trp Tyr Gln Gln Lys Pro Gly
            165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
            195                 200                 205

Thr Ile Ser Arg Leu Glu Pro Glu Asp Phe Ala Val Tyr Tyr Cys Gln
            210                 215                 220

Gln Tyr Phe Asn Pro Pro Glu Tyr Thr Phe Gly Gln Gly Thr Lys Val
225                 230                 235                 240

Glu Ile Lys Arg

<210> SEQ ID NO 56
<211> LENGTH: 119
<212> TYPE: PRT
<213> ORGANISM: Artificial sequence
<220> FEATURE:
<223> OTHER INFORMATION: 25C2 VH(AA)

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Asn
            20                  25                  30

Ala Met Ser Trp Val Arg Gln Ala Pro Gly Lys Gly Leu Glu Trp Val
            35                  40                  45

Ser Ala Ile Ser Gly Asn Gly Gly Ser Thr Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Val Arg Pro Phe Trp Gly Thr Phe Asp Tyr Trp Gly Gln Gly
            100                 105                 110

Thr Leu Val Thr Val Ser Ser
            115

<210> SEQ ID NO 57
<211> LENGTH: 357
<212> TYPE: DNA
<213> ORGANISM: Artificial sequence
<220> FEATURE:
<223> OTHER INFORMATION: 25C2 VH

<400> SEQUENCE: 57

```
gaggtgcaat tgctggagtc tgggggaggc ttggtacagc ctgggggtc cctgagactc      60 tcctgtgcag cctccggatt cacctttggc ggtaatgcca tgtcctgggt ccgccaggct    120
ccagggaagg ggctggagtg gtctcagca attagtggta atggtggtag tacattctac     180
gcagactccg tgaagggccg gttcaccatc tccagagaca attccaagaa cacgctgtat    240
ctgcagatga acagcctgag agccgaggac acggccgtat attactgtgc gaaagttcgt    300
ccattctggg gtactttcga ctactggggc caaggaaccc tggtcaccgt ctcgagt       357
```

<210> SEQ ID NO 58
<211> LENGTH: 119
<212> TYPE: PRT
<213> ORGANISM: Artificial sequence
<220> FEATURE:
<223> OTHER INFORMATION: 25D2 VH(AA)

<400> SEQUENCE: 58

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Pro Phe Trp Gly Thr Phe Asp Tyr Trp Gly Gln Gly
            100                 105                 110

Thr Leu Val Thr Val Ser Ser
        115
```

<210> SEQ ID NO 59
<211> LENGTH: 357
<212> TYPE: DNA
<213> ORGANISM: Artificial sequence
<220> FEATURE:
<223> OTHER INFORMATION: 25D2 VH

<400> SEQUENCE: 59

```
gaggtgcaat tgctggagtc tgggggaggc ttggtacagc ctgggggtc cctgagactc      60 tcctgtgcag cctccggatt cacctttagg agctatgcca tgagctgggt ccgccaggct    120
ccagggaagg ggctggagtg gtctcagct attagtggcg gtggtggtaa cacattctac     180
gcagactccg tgaagggccg gttcaccatc tccagagaca attccaagaa cacgctgtat    240
ctgcagatga acagcctgag agccgaggac acggccgtat attactgtgc gaaagttcgt    300
ccattctggg gtactttcga ctactggggc caaggaaccc tggtcaccgt ctcgagt       357
```

```
<210> SEQ ID NO 60
<211> LENGTH: 5
<212> TYPE: PRT
<213> ORGANISM: Artificial sequence
<220> FEATURE:
<223> OTHER INFORMATION: 25C2 HCDR1

<400> SEQUENCE: 60

Gly Asn Ala Met Ser
1               5

<210> SEQ ID NO 61
<211> LENGTH: 17
<212> TYPE: PRT
<213> ORGANISM: Artificial sequence
<220> FEATURE:
<223> OTHER INFORMATION: 25C2 HCDR2

<400> SEQUENCE: 61

Ala Ile Ser Gly Asn Gly Gly Ser Thr Phe Tyr Ala Asp Ser Val Lys
1               5                   10                  15
Gly

<210> SEQ ID NO 62
<211> LENGTH: 5
<212> TYPE: PRT
<213> ORGANISM: Artificial sequence
<220> FEATURE:
<223> OTHER INFORMATION: 25D2 HCDR1

<400> SEQUENCE: 62

Ser Tyr Ala Met Ser
1               5

<210> SEQ ID NO 63
<211> LENGTH: 17
<212> TYPE: PRT
<213> ORGANISM: Artificial sequence
<220> FEATURE:
<223> OTHER INFORMATION: 25D2 HCDR2

<400> SEQUENCE: 63

Ala Ile Ser Gly Gly Gly Gly Asn Thr Phe Tyr Ala Asp Ser Val Lys
1               5                   10                  15
Gly

<210> SEQ ID NO 64
<211> LENGTH: 732
<212> TYPE: DNA
<213> ORGANISM: Artificial sequence
<220> FEATURE:
<223> OTHER INFORMATION: 25C2 scFv

<400> SEQUENCE: 64
gaggtgcaat tgctggagtc tgggggaggc ttggtacagc ctggggggtc cctgagactc        60
tcctgtgcag cctccggatt cacctttggc ggtaatgcca tgtcctgggt ccgccaggct       120
ccagggaagg gctggagtg gtctcagca attagtggta atggtggtag tacattctac         180
gcagactccg tgaagggccg gttcaccatc tccagagaca attccaagaa cacgctgtat       240
ctgcagatga acagcctgag agccgaggac acggccgtat attactgtgc gaaagttcgt       300
ccattctggg gtactttcga ctactggggc caaggaaccc tggtcaccgt ctcgagtggt       360
ggaggcggtt caggcggagg tggttctggc ggtggcggat cggaaatcgt gttaacgcag       420
```

```
tctccaggca ccctgtcttt gtctccaggg gaaagagcca ccctctcttg cagggccagt      480
cagagtgtta gcagcagcta cttagcctgg taccagcaga aacctggcca ggctcccagg      540
ctcctcatct atggagcatc cagcagggcc actggcatcc cagacaggtt cagtggcagt      600
ggatccggga cagacttcac tctcaccatc agcagactgg agcctgaaga ttttgcagtg      660
tattactgtc agcagtactt caacccacca gaatacacgt tcggccaggg gaccaaagtg      720
gaaatcaaac gt                                                         732
```

```
<210> SEQ ID NO 65
<211> LENGTH: 244
<212> TYPE: PRT
<213> ORGANISM: Artificial sequence
<220> FEATURE:
<223> OTHER INFORMATION: 25C2 scFv(AA)

<400> SEQUENCE: 65
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Asn
            20                  25                  30

Ala Met Ser Trp Val Arg Gln Ala Pro Gly Lys Gly Leu Glu Trp Val
        35                  40                  45

Ser Ala Ile Ser Gly Asn Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Pro Phe Trp Gly Thr Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Glu Ile Val Leu Thr Gln Ser Pro Gly Thr
    130                 135                 140

Leu Ser Leu Ser Pro Gly Glu Arg Ala Thr Leu Ser Cys Arg Ala Ser
145                 150                 155                 160

Gln Ser Val Ser Ser Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220

Gln Tyr Phe Asn Pro Pro Glu Tyr Thr Phe Gly Gln Gly Thr Lys Val
225                 230                 235                 240

Glu Ile Lys Arg

```
<210> SEQ ID NO 66
<211> LENGTH: 732
<212> TYPE: DNA
<213> ORGANISM: Artificial sequence
<220> FEATURE:
<223> OTHER INFORMATION: 25D2 scFv
```

<400> SEQUENCE: 66

```
gaggtgcaat tgctggagtc tgggggaggc ttggtacagc ctgggggtc cctgagactc      60
tcctgtgcag cctccggatt cacctttagg agctatgcca tgagctgggt ccgccaggct    120
ccagggaagg ggctggagtg ggtctcagct attagtggcg gtggtggtaa cacattctac    180
gcagactccg tgaagggccg gttcaccatc tccagagaca attccaagaa cacgctgtat    240
ctgcagatga acagcctgag agccgaggac acggccgtat attactgtgc gaaagttcgt    300
ccattctggg gtactttcga ctactggggc caaggaaccc tggtcaccgt ctcgagtggt    360
ggaggcggtt caggcggagg tggttctggc ggtggcggat cggaaatcgt gttaacgcag    420
tctccaggca ccctgtcttt gtctccaggg gaaagagcca ccctctcttg cagggccagt    480
cagagtgtta gcagcagcta cttagcctgg taccagcaga aacctggcca ggctcccagg    540
ctcctcatct atggagcatc cagcagggcc actggcatcc cagacaggtt cagtggcagt    600
ggatccggga cagacttcac tctcaccatc agcagactgg agcctgaaga ttttgcagtg    660
tattactgtc agcagtactt caacccacca gaatacacgt tcggccaggg gaccaaagtg    720
gaaatcaaac gt                                                         732
```

<210> SEQ ID NO 67
<211> LENGTH: 244
<212> TYPE: PRT
<213> ORGANISM: Artificial sequence
<220> FEATURE:
<223> OTHER INFORMATION: 25D2 scFv(AA)

<400> SEQUENCE: 67

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Pro Phe Trp Gly Thr Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Gly Thr
    130                 135                 140

Leu Ser Leu Ser Pro Gly Glu Arg Ala Thr Leu Ser Cys Arg Ala Ser
145                 150                 155                 160

Gln Ser Val Ser Ser Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220
```

Gln Tyr Phe Asn Pro Pro Glu Tyr Thr Phe Gly Gln Gly Thr Lys Val
225                 230                 235                 240

Glu Ile Lys Arg

<210> SEQ ID NO 68
<211> LENGTH: 60
<212> TYPE: DNA
<213> ORGANISM: Artificial sequence
<220> FEATURE:
<223> OTHER INFORMATION: PD-1 signal peptide sequence

<400> SEQUENCE: 68
atgcagatcc cacaggcgcc ctggccagtc gtctgggcgg tgctacaact gggctggcgg    60

<210> SEQ ID NO 69
<211> LENGTH: 450
<212> TYPE: DNA
<213> ORGANISM: Artificial sequence
<220> FEATURE:
<223> OTHER INFORMATION: PD-1 extracellular segment sequence

<400> SEQUENCE: 69
ccaggatggt tcttagactc cccagacagg ccctggaacc cccccacctt ctccccagcc    60
ctgctcgtgg tgaccgaagg ggacaacgcc accttcacct gcagcttctc caacacatcg   120
gagagcttcg tgctaaactg gtaccgcatg agccccagca accagacgga caagctggcc   180
gccttccccg aggaccgcag ccagcccggc caggactgcc gcttccgtgt cacacaactg   240
cccaacgggc gtgacttcca catgagcgtg gtcagggccc ggcgcaatga cagcggcacc   300
tacctctgtg gggccatctc cctggccccc aaggcgcaga tcaaagagag cctgcgggca   360
gagctcaggg tgacagagag aagggcagaa gtgcccacag cccaccccag ccctcacccc   420
aggccagccg ccagttccaa accctggtg                                      450

<210> SEQ ID NO 70
<211> LENGTH: 321
<212> TYPE: DNA
<213> ORGANISM: Artificial sequence
<220> FEATURE:
<223> OTHER INFORMATION: DNA sequence of CH3 domain

<400> SEQUENCE: 70
cccccatgcc caccatgccc agcacctgag ttcctggggg gaccatcagt cttcctgttc    60
cccccaaaac ccaaggacac tctcatgatc tcccggaccc ctgaggtcac gtgcgtggtg   120
gtggacgtga gccaggaaga ccccgaggtc cagttcaact ggtacgtgga tggcgtggag   180
gtgcataatg ccaagacaaa gccgcgggag gagcagttca acagcacgta ccgtgtggtc   240
agcgtcctca ccgtcctgca ccaggactgg ctgaacggca aggagtacaa gtgcaaggtc   300
tccaacaaag gcctcccgtc c                                              321

<210> SEQ ID NO 71
<211> LENGTH: 49
<212> TYPE: DNA
<213> ORGANISM: Artificial sequence
<220> FEATURE:
<223> OTHER INFORMATION: Primer

<400> SEQUENCE: 71
acgcgtccta gcgctaccgg tcgccaccat gcagatccca caggcgccc                49

-continued

<210> SEQ ID NO 72
<211> LENGTH: 41
<212> TYPE: DNA
<213> ORGANISM: Artificial sequence
<220> FEATURE:
<223> OTHER INFORMATION: Primer

<400> SEQUENCE: 72
ctctcggggc tgcccaccat acaccagggt ttggaactgg c        41

<210> SEQ ID NO 73
<211> LENGTH: 27
<212> TYPE: DNA
<213> ORGANISM: Artificial sequence
<220> FEATURE:
<223> OTHER INFORMATION: Primer

<400> SEQUENCE: 73
tatggtgggc agccccgaga gccacag        27

<210> SEQ ID NO 74
<211> LENGTH: 40
<212> TYPE: DNA
<213> ORGANISM: Artificial sequence
<220> FEATURE:
<223> OTHER INFORMATION: Primer

<400> SEQUENCE: 74
aaaattcaaa gtctgtttca ctttacccgg agacagggag        40

<210> SEQ ID NO 75
<211> LENGTH: 465
<212> TYPE: PRT
<213> ORGANISM: Artificial sequence
<220> FEATURE:
<223> OTHER INFORMATION: 7A12-BBZ

<400> SEQUENCE: 75

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Leu Ala Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Gly Thr Leu Ser
    130                 135                 140

Leu Ser Pro Gly Glu Arg Ala Thr Leu Ser Cys Arg Ala Ser Gln Ser
145                 150                 155                 160

Val Ser Ser Ser Tyr Leu Ala Trp Tyr Gln Gln Lys Pro Gly Gln Ala
                165                 170                 175

```
Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Tyr
    210                 215                 220

Gly Tyr Pro Pro Ser Tyr Thr Phe Gly Gln Gly Thr Lys Val Glu Ile
225                 230                 235                 240

Lys Arg Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Ile
        275                 280                 285

Tyr Ile Trp Ala Pro Leu Ala Gly Thr Cys Gly Val Leu Leu Leu Ser
    290                 295                 300

Leu Val Ile Thr Leu Tyr Cys Lys Arg Gly Arg Lys Lys Leu Leu Tyr
305                 310                 315                 320

Ile Phe Lys Gln Pro Phe Met Arg Pro Val Gln Thr Thr Gln Glu Glu
                325                 330                 335

Asp Gly Cys Ser Cys Arg Phe Pro Glu Glu Glu Glu Gly Gly Cys Glu
            340                 345                 350

Leu Arg Val Lys Phe Ser Arg Ser Ala Asp Ala Pro Ala Tyr Lys Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415

Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg
465

<210> SEQ ID NO 76
<211> LENGTH: 467
<212> TYPE: PRT
<213> ORGANISM: Artificial sequence
<220> FEATURE:
<223> OTHER INFORMATION: 25C2-BBZ

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Asn
            20                  25                  30

Ala Met Ser Trp Val Arg Gln Ala Pro Gly Lys Gly Leu Glu Trp Val
        35                  40                  45

Ser Ala Ile Ser Gly Asn Gly Ser Thr Phe Tyr Ala Asp Ser Val
    50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Arg Pro Phe Trp Gly Thr Phe Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Glu Ile Val Leu Thr Gln Ser Pro Gly Thr
            130                 135                 140

Leu Ser Leu Ser Pro Gly Glu Arg Ala Thr Leu Ser Cys Arg Ala Ser
145                 150                 155                 160

Gln Ser Val Ser Ser Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
            195                 200                 205

Thr Ile Ser Arg Leu Glu Pro Glu Asp Phe Ala Val Tyr Tyr Cys Gln
    210                 215                 220

Gln Tyr Phe Asn Pro Pro Glu Tyr Thr Phe Gly Gln Gly Thr Lys Val
225                 230                 235                 240

Glu Ile Lys Arg Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
            275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
            355                 360                 365

Lys Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
            435                 440                 445

Ser Thr Ala Thr Lys Asp Thr Tyr Asp Ala Leu His Met Gln Ala Leu
    450                 455                 460

Pro Pro Arg
465
```

<210> SEQ ID NO 77
<211> LENGTH: 467
<212> TYPE: PRT
<213> ORGANISM: Artificial sequence
<220> FEATURE:
<223> OTHER INFORMATION: 25D2-BBZ

<400> SEQUENCE: 77

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Pro Phe Trp Gly Thr Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Glu Ile Val Leu Thr Gln Ser Pro Gly Thr
    130                 135                 140

Leu Ser Leu Ser Pro Gly Glu Arg Ala Thr Leu Ser Cys Arg Ala Ser
145                 150                 155                 160

Gln Ser Val Ser Ser Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220

Gln Tyr Phe Asn Pro Pro Glu Tyr Thr Phe Gly Gln Gly Thr Lys Val
225                 230                 235                 240

Glu Ile Lys Arg Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
        355                 360                 365
```

```
Lys Gln Gly Gln Asn Gln Leu Tyr Asn Glu Leu Asn Leu Gly Arg Arg
    370                 375                 380

Glu Glu Tyr Asp Val Leu Asp Lys Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
                435                 440                 445

Ser Thr Ala Thr Lys Asp Thr Tyr Asp Ala Leu His Met Gln Ala Leu
    450                 455                 460

Pro Pro Arg
465

<210> SEQ ID NO 78
<211> LENGTH: 466
<212> TYPE: PRT
<213> ORGANISM: Artificial sequence
<220> FEATURE:
<223> OTHER INFORMATION: 7G2-BBZ

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Asp Ala Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Lys Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Gly Tyr Pro Pro Arg Tyr Thr Phe Gly Gln Gly Thr Lys Val Glu
225                 230                 235                 240

Ile Lys Arg Thr Thr Thr Pro Ala Pro Arg Pro Pro Thr Pro Ala Pro
                245                 250                 255
```

```
Thr Ile Ala Ser Gln Pro Leu Ser Leu Arg Pro Glu Ala Cys Arg Pro
                260                 265                 270

Ala Ala Gly Gly Ala Val His Thr Arg Gly Leu Asp Phe Ala Cys Asp
            275                 280                 285

Ile Tyr Ile Trp Ala Pro Leu Ala Gly Thr Cys Gly Val Leu Leu Leu
        290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Lys
        355                 360                 365

Gln Gly Gln Asn Gln Leu Tyr Asn Glu Leu Asn Leu Gly Arg Arg Glu
        370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
        450                 455                 460

Pro Arg
465

<210> SEQ ID NO 79
<211> LENGTH: 468
<212> TYPE: PRT
<213> ORGANISM: Artificial sequence
<220> FEATURE:
<223> OTHER INFORMATION: 7A12-28Z

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Pro Tyr Leu Ala Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Leu Thr Gln Ser Pro Gly Thr Leu Ser
    130                 135                 140
```

Leu Ser Pro Gly Glu Arg Ala Thr Leu Ser Cys Arg Ala Ser Gln Ser
145                 150                 155                 160

Val Ser Ser Ser Tyr Leu Ala Trp Tyr Gln Gln Lys Pro Gly Gln Ala
            165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
        195                 200                 205

Ser Arg Leu Glu Pro Glu Asp Phe Ala Val Tyr Tyr Cys Gln Gln Tyr
    210                 215                 220

Gly Tyr Pro Pro Ser Tyr Thr Phe Gly Gln Gly Thr Lys Val Glu Ile
225                 230                 235                 240

Lys Arg Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Gln Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg
465

<210> SEQ ID NO 80
<211> LENGTH: 510
<212> TYPE: PRT
<213> ORGANISM: Artificial sequence
<220> FEATURE:
<223> OTHER INFORMATION: 7A12-28BBZ

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
           35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Pro Tyr Leu Ala Phe Asp Tyr Trp Gly Gln Gly Thr Leu
                100                 105                 110

Val Thr Val Ser Ser Gly Gly Gly Ser Gly Gly Gly Gly Ser Gly
            115                 120                 125

Gly Gly Gly Ser Glu Ile Val Leu Thr Gln Ser Pro Gly Thr Leu Ser
            130                 135                 140

Leu Ser Pro Gly Glu Arg Ala Thr Leu Ser Cys Arg Ala Ser Gln Ser
145                 150                 155                 160

Val Ser Ser Ser Tyr Leu Ala Trp Tyr Gln Gln Lys Pro Gly Gln Ala
                165                 170                 175

Pro Arg Leu Leu Ile Tyr Gly Ala Ser Ser Arg Ala Thr Gly Ile Pro
            180                 185                 190

Asp Arg Phe Ser Gly Ser Gly Ser Gly Thr Asp Phe Thr Leu Thr Ile
            195                 200                 205

Ser Arg Leu Glu Pro Glu Asp Phe Ala Val Tyr Tyr Cys Gln Gln Tyr
            210                 215                 220

Gly Tyr Pro Pro Ser Tyr Thr Phe Gly Gln Gly Thr Lys Val Glu Ile
225                 230                 235                 240

Lys Arg Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Phe
            275                 280                 285

Trp Val Leu Val Val Val Gly Gly Val Leu Ala Cys Tyr Ser Leu Leu
290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
            325                 330                 335

Thr Arg Lys His Tyr Gln Pro Tyr Ala Pro Pro Arg Asp Phe Ala Ala
            340                 345                 350

Tyr Arg Ser Lys Arg Gly Arg Lys Lys Leu Leu Tyr Ile Phe Lys Gln
            355                 360                 365

Pro Phe Met Arg Pro Val Gln Thr Thr Gln Glu Glu Asp Gly Cys Ser
            370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Gln Arg
            435                 440                 445

```
Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 81
<211> LENGTH: 469
<212> TYPE: PRT
<213> ORGANISM: Artificial sequence
<220> FEATURE:
<223> OTHER INFORMATION: 7G2-28Z

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Asp Ala Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Lys Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Gly Tyr Pro Pro Arg Tyr Thr Phe Gly Gln Gly Thr Lys Val Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Phe Trp Val Leu Val Val Val Gly Gly Val Leu Ala Cys Tyr Ser Leu
    290                 295                 300
```

```
Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
            325                 330                 335

Pro Thr Arg Lys His Tyr Gln Pro Tyr Ala Pro Pro Arg Asp Phe Ala
            340                 345                 350

Ala Tyr Arg Ser Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Gln Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
                420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
450                 455                 460

Ala Leu Pro Pro Arg
465

<210> SEQ ID NO 82
<211> LENGTH: 511
<212> TYPE: PRT
<213> ORGANISM: Artificial sequence
<220> FEATURE:
<223> OTHER INFORMATION: 7G2-28BBZ

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ser Gly Asp Ala Ala Met Asp Tyr Trp Gly Gln Gly Thr
            100                 105                 110

Leu Val Thr Val Ser Ser Gly Gly Gly Gly Ser Gly Gly Gly Gly Ser
            115                 120                 125

Gly Gly Gly Gly Ser Glu Ile Val Leu Thr Gln Ser Pro Gly Thr Leu
130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Lys Pro Gly Gln
                165                 170                 175

Ala Pro Arg Leu Leu Ile Tyr Gly Ala Ser Ser Arg Ala Thr Gly Ile
            180                 185                 190
```

```
Pro Asp Arg Phe Ser Gly Ser Gly Ser Gly Thr Asp Phe Thr Leu Thr
            195                 200                 205

Ile Ser Arg Leu Glu Pro Glu Asp Phe Ala Val Tyr Tyr Cys Gln Gln
    210                 215                 220

Tyr Gly Tyr Pro Pro Arg Tyr Thr Phe Gly Gln Gly Thr Lys Val Glu
225                 230                 235                 240

Ile Lys Arg Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Phe Trp Val Leu Val Val Val Gly Gly Val Leu Ala Cys Tyr Ser Leu
    290                 295                 300

Leu Val Thr Val Ala Phe Ile Ile Phe Trp Val Arg Ser Lys Arg Ser
305                 310                 315                 320

Arg Leu Leu His Ser Asp Tyr Met Asn Met Thr Pro Arg Arg Pro Gly
                325                 330                 335

Pro Thr Arg Lys His Tyr Gln Pro Tyr Ala Pro Pro Arg Asp Phe Ala
            340                 345                 350

Ala Tyr Arg Ser Lys Arg Gly Arg Lys Lys Leu Leu Tyr Ile Phe Lys
        355                 360                 365

Gln Pro Phe Met Arg Pro Val Gln Thr Thr Gln Glu Glu Asp Gly Cys
    370                 375                 380

Ser Cys Arg Phe Pro Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Gln
        435                 440                 445

Arg Arg Lys Asn Pro Gln Glu Gly Leu Tyr Asn Glu Leu Gln Lys Asp
    450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
                485                 490                 495

Lys Asp Thr Tyr Asp Ala Leu His Met Gln Ala Leu Pro Pro Arg
            500                 505                 510

<210> SEQ ID NO 83
<211> LENGTH: 470
<212> TYPE: PRT
<213> ORGANISM: Artificial sequence
<220> FEATURE:
<223> OTHER INFORMATION: 23F10-28Z

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Val Arg Pro Phe Trp Gly Thr Phe Asp Tyr Trp Gly Gln Gly
                100                 105                 110
Thr Leu Val Thr Val Ser Ser Gly Gly Gly Gly Ser Gly Gly Gly Gly
            115                 120                 125
Ser Gly Gly Gly Gly Ser Glu Ile Val Leu Thr Gln Ser Pro Gly Thr
    130                 135                 140
Leu Ser Leu Ser Pro Gly Glu Arg Ala Thr Leu Ser Cys Arg Ala Ser
145                 150                 155                 160
Gln Ser Val Ser Ser Ser Tyr Leu Ala Trp Tyr Gln Gln Lys Pro Gly
                165                 170                 175
Gln Ala Pro Arg Leu Leu Ile Tyr Gly Ala Ser Ser Arg Ala Thr Gly
                180                 185                 190
Ile Pro Asp Arg Phe Ser Gly Ser Gly Ser Gly Thr Asp Phe Thr Leu
                195                 200                 205
Thr Ile Ser Arg Leu Glu Pro Glu Asp Phe Ala Val Tyr Tyr Cys Gln
            210                 215                 220
Gln Tyr Phe Asn Pro Pro Glu Tyr Thr Phe Gly Gln Gly Thr Lys Val
225                 230                 235                 240
Glu Ile Lys Arg Thr Thr Thr Pro Ala Pro Arg Pro Thr Pro Thr Pro Ala
                245                 250                 255
Pro Thr Ile Ala Ser Gln Pro Leu Ser Leu Arg Pro Glu Ala Cys Arg
            260                 265                 270
Pro Ala Ala Gly Gly Ala Val His Thr Arg Gly Leu Asp Phe Ala Cys
            275                 280                 285
Asp Phe Trp Val Leu Val Val Val Gly Gly Val Leu Ala Cys Tyr Ser
            290                 295                 300
Leu Leu Val Thr Val Ala Phe Ile Ile Phe Trp Val Arg Ser Lys Arg
305                 310                 315                 320
Ser Arg Leu Leu His Ser Asp Tyr Met Asn Met Thr Pro Arg Arg Pro
                325                 330                 335
Gly Pro Thr Arg Lys His Tyr Gln Pro Tyr Ala Pro Pro Arg Asp Phe
                340                 345                 350
Ala Ala Tyr Arg Ser Arg Val Lys Phe Ser Arg Ser Ala Asp Ala Pro
            355                 360                 365
Ala Tyr Gln Gln Gly Gln Asn Gln Leu Tyr Asn Glu Leu Asn Leu Gly
            370                 375                 380
Arg Arg Glu Glu Tyr Asp Val Leu Asp Lys Arg Arg Gly Arg Asp Pro
385                 390                 395                 400
Glu Met Gly Gly Lys Pro Gln Arg Arg Lys Asn Pro Gln Glu Gly Leu
                405                 410                 415
Tyr Asn Glu Leu Gln Lys Asp Lys Met Ala Glu Ala Tyr Ser Glu Ile
                420                 425                 430
Gly Met Lys Gly Glu Arg Arg Arg Gly Lys Gly His Asp Gly Leu Tyr
            435                 440                 445
```

Gln Gly Leu Ser Thr Ala Thr Lys Asp Thr Tyr Asp Ala Leu His Met
            450                 455                 460

Gln Ala Leu Pro Pro Arg
465                 470

<210> SEQ ID NO 84
<211> LENGTH: 512
<212> TYPE: PRT
<213> ORGANISM: Artificial sequence
<220> FEATURE:
<223> OTHER INFORMATION: 23F10-28BBZ

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Pro Phe Trp Gly Thr Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Gly Thr
    130                 135                 140

Leu Ser Leu Ser Pro Gly Glu Arg Ala Thr Leu Ser Cys Arg Ala Ser
145                 150                 155                 160

Gln Ser Val Ser Ser Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220

Gln Tyr Phe Asn Pro Pro Glu Tyr Thr Phe Gly Gln Gly Thr Lys Val
225                 230                 235                 240

Glu Ile Lys Arg Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Phe Trp Val Leu Val Val Val Gly Gly Val Leu Ala Cys Tyr Ser
    290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
                325                 330                 335

```
Gly Pro Thr Arg Lys His Tyr Gln Pro Tyr Ala Pro Pro Arg Asp Phe
                340                 345                 350
Ala Ala Tyr Arg Ser Lys Arg Gly Arg Lys Leu Leu Tyr Ile Phe
            355                 360                 365
Lys Gln Pro Phe Met Arg Pro Val Gln Thr Thr Gln Glu Glu Asp Gly
        370                 375                 380
Cys Ser Cys Arg Phe Pro Glu Glu Glu Glu Gly Cys Glu Leu Arg
385                 390                 395                 400
Val Lys Phe Ser Arg Ser Ala Asp Ala Pro Ala Tyr Gln Gln Gly Gln
                405                 410                 415
Asn Gln Leu Tyr Asn Glu Leu Asn Leu Gly Arg Arg Glu Glu Tyr Asp
            420                 425                 430
Val Leu Asp Lys Arg Arg Gly Arg Asp Pro Glu Met Gly Gly Lys Pro
        435                 440                 445
Gln Arg Arg Lys Asn Pro Gln Glu Gly Leu Tyr Asn Glu Leu Gln Lys
    450                 455                 460
Asp Lys Met Ala Glu Ala Tyr Ser Glu Ile Gly Met Lys Gly Glu Arg
465                 470                 475                 480
Arg Arg Gly Lys Gly His Asp Gly Leu Tyr Gln Gly Leu Ser Thr Ala
                485                 490                 495
Thr Lys Asp Thr Tyr Asp Ala Leu His Met Gln Ala Leu Pro Pro Arg
            500                 505                 510

<210> SEQ ID NO 85
<211> LENGTH: 470
<212> TYPE: PRT
<213> ORGANISM: Artificial sequence
<220> FEATURE:
<223> OTHER INFORMATION: 25D2-28Z

<400> SEQUENCE: 85

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Arg Ser Tyr
            20                  25                  30
Ala Met Ser Trp Val Arg Gln Ala Pro Gly Lys Gly Leu Glu Trp Val
        35                  40                  45
Ser Ala Ile Ser Gly Gly Gly Asn Thr Phe Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Val Arg Pro Phe Trp Gly Thr Phe Asp Tyr Trp Gly Gln Gly
            100                 105                 110
Thr Leu Val Thr Val Ser Ser Gly Gly Gly Ser Gly Gly Gly Gly
        115                 120                 125
Ser Gly Gly Gly Gly Ser Glu Ile Val Leu Thr Gln Ser Pro Gly Thr
    130                 135                 140
Leu Ser Leu Ser Pro Gly Glu Arg Ala Thr Leu Ser Cys Arg Ala Ser
145                 150                 155                 160
Gln Ser Val Ser Ser Ser Tyr Leu Ala Trp Tyr Gln Gln Lys Pro Gly
                165                 170                 175
Gln Ala Pro Arg Leu Leu Ile Tyr Gly Ala Ser Ser Arg Ala Thr Gly
            180                 185                 190
```

```
Ile Pro Asp Arg Phe Ser Gly Ser Gly Ser Gly Thr Asp Phe Thr Leu
            195                 200                 205

Thr Ile Ser Arg Leu Glu Pro Glu Asp Phe Ala Val Tyr Tyr Cys Gln
    210                 215                 220

Gln Tyr Phe Asn Pro Pro Glu Tyr Thr Phe Gly Gln Gly Thr Lys Val
225                 230                 235                 240

Glu Ile Lys Arg Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
                260                 265                 270

Pro Ala Ala Gly Gly Ala Val His Thr Arg Gly Leu Asp Phe Ala Cys
                275                 280                 285

Asp Phe Trp Val Leu Val Val Val Gly Gly Val Leu Ala Cys Tyr Ser
        290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
                325                 330                 335

Gly Pro Thr Arg Lys His Tyr Gln Pro Tyr Ala Pro Pro Arg Asp Phe
                340                 345                 350

Ala Ala Tyr Arg Ser Arg Val Lys Phe Ser Arg Ser Ala Asp Ala Pro
                355                 360                 365

Ala Tyr Gln Gln Gly Gln Asn Gln Leu Tyr Asn Glu Leu Asn Leu Gly
                370                 375                 380

Arg Arg Glu Glu Tyr Asp Val Leu Asp Lys Arg Arg Gly Arg Asp Pro
385                 390                 395                 400

Glu Met Gly Gly Lys Pro Gln Arg Arg Lys Asn Pro Gln Glu Gly Leu
                405                 410                 415

Tyr Asn Glu Leu Gln Lys Asp Lys Met Ala Glu Ala Tyr Ser Glu Ile
                420                 425                 430

Gly Met Lys Gly Glu Arg Arg Arg Gly Lys Gly His Asp Gly Leu Tyr
                435                 440                 445

Gln Gly Leu Ser Thr Ala Thr Lys Asp Thr Tyr Asp Ala Leu His Met
    450                 455                 460

Gln Ala Leu Pro Pro Arg
465                 470

<210> SEQ ID NO 86
<211> LENGTH: 512
<212> TYPE: PRT
<213> ORGANISM: Artificial sequence
<220> FEATURE:
<223> OTHER INFORMATION: 25D2-28BBZ

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Gly Asn Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                 85                  90                  95

Ala Lys Val Arg Pro Phe Trp Gly Thr Phe Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Glu Ile Val Leu Thr Gln Ser Pro Gly Thr
        130                 135                 140

Leu Ser Leu Ser Pro Gly Glu Arg Ala Thr Leu Ser Cys Arg Ala Ser
145                 150                 155                 160

Gln Ser Val Ser Ser Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
                180                 185                 190

Ile Pro Asp Arg Phe Ser Gly Ser Gly Ser Gly Thr Asp Phe Thr Leu
            195                 200                 205

Thr Ile Ser Arg Leu Glu Pro Glu Asp Phe Ala Val Tyr Tyr Cys Gln
    210                 215                 220

Gln Tyr Phe Asn Pro Pro Glu Tyr Thr Phe Gly Gln Gly Thr Lys Val
225                 230                 235                 240

Glu Ile Lys Arg Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
            275                 280                 285

Asp Phe Trp Val Leu Val Val Val Gly Val Leu Ala Cys Tyr Ser
            290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
                325                 330                 335

Gly Pro Thr Arg Lys His Tyr Gln Pro Tyr Ala Pro Pro Arg Asp Phe
            340                 345                 350

Ala Ala Tyr Arg Ser Lys Arg Gly Arg Lys Lys Leu Leu Tyr Ile Phe
            355                 360                 365

Lys Gln Pro Phe Met Arg Pro Val Gln Thr Thr Gln Glu Glu Asp Gly
    370                 375                 380

Cys Ser Cys Arg Phe Pro Glu Glu Glu Glu Gly Gly Cys Glu Leu Arg
385                 390                 395                 400

Val Lys Phe Ser Arg Ser Ala Asp Ala Pro Ala Tyr Gln Gln Gly Gln
                405                 410                 415

Asn Gln Leu Tyr Asn Glu Leu Asn Leu Gly Arg Arg Glu Glu Tyr Asp
            420                 425                 430

Val Leu Asp Lys Arg Arg Gly Arg Asp Pro Glu Met Gly Gly Lys Pro
        435                 440                 445

Gln Arg Arg Lys Asn Pro Gln Glu Gly Leu Tyr Asn Glu Leu Gln Lys
    450                 455                 460

Asp Lys Met Ala Glu Ala Tyr Ser Glu Ile Gly Met Lys Gly Glu Arg
465                 470                 475                 480
```

```
Arg Arg Gly Lys Gly His Asp Gly Leu Tyr Gln Gly Leu Ser Thr Ala
                485                 490                 495

Thr Lys Asp Thr Tyr Asp Ala Leu His Met Gln Ala Leu Pro Pro Arg
            500                 505                 510

<210> SEQ ID NO 87
<211> LENGTH: 466
<212> TYPE: PRT
<213> ORGANISM: Artificial sequence
<220> FEATURE:
<223> OTHER INFORMATION: C11D5.3-BBZ

<400> SEQUENCE: 87

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser Gly Gly Gly Ser Gly Gly Gly Ser Gly
        115                 120                 125

Gly Gly Gly Ser Asp Ile Val Leu Thr Gln Ser Pro Pro Ser Leu Ala
130                 135                 140

Met Ser Leu Gly Lys Arg Ala Thr Ile Ser Cys Arg Ala Ser Glu Ser
145                 150                 155                 160

Val Thr Ile Leu Gly Ser His Leu Ile His Trp Tyr Gln Gln Lys Pro
                165                 170                 175

Gly Gln Pro Pro Thr Leu Leu Ile Gln Leu Ala Ser Asn Val Gln Thr
            180                 185                 190

Gly Val Pro Ala Arg Phe Ser Gly Ser Gly Ser Arg Thr Asp Phe Thr
        195                 200                 205

Leu Thr Ile Asp Pro Val Glu Glu Asp Val Ala Val Tyr Tyr Cys
    210                 215                 220

Leu Gln Ser Arg Thr Ile Pro Arg Thr Phe Gly Gly Gly Thr Lys Leu
225                 230                 235                 240

Glu Ile Lys Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
    290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335
```

-continued

```
Glu Asp Gly Cys Ser Cys Arg Phe Pro Glu Glu Glu Glu Gly Gly Cys
                340                 345                 350
Glu Leu Arg Val Lys Phe Ser Arg Ser Ala Asp Ala Pro Ala Tyr Lys
        355                 360                 365
Gln Gly Gln Asn Gln Leu Tyr Asn Glu Leu Asn Leu Gly Arg Arg Glu
    370                 375                 380
Glu Tyr Asp Val Leu Asp Lys Arg Arg Gly Arg Asp Pro Glu Met Gly
385                 390                 395                 400
Gly Lys Pro Arg Arg Lys Asn Pro Gln Glu Gly Leu Tyr Asn Glu Leu
                405                 410                 415
Gln Lys Asp Lys Met Ala Glu Ala Tyr Ser Glu Ile Gly Met Lys Gly
                420                 425                 430
Glu Arg Arg Arg Gly Lys Gly His Asp Gly Leu Tyr Gln Gly Leu Ser
            435                 440                 445
Thr Ala Thr Lys Asp Thr Tyr Asp Ala Leu His Met Gln Ala Leu Pro
    450                 455                 460
Pro Arg
465
```

BCMA-TARGETING ANTIBODY AND USE THEREOF

TECHNICAL FIELD

The present invention belongs to the field of tumor immunotherapy or diagnosis; and in particular, the present invention relates to an antibody that targets BCMA and uses thereof.

REFERENCE TO A "SEQUENCE LISTING"

The Sequence_Listing.txt created on May 23, 2022 (114, 688 bytes in size), machine format IBM-PC, MS-Windows operating system, is hereby incorporated by reference in its entirety for all purposes.

BACKGROUND

Multiple myeloma (MM) is a common hematological malignancy, accounting for 2% of all deaths resulted from cancer. MM is a heterogeneous disease and mainly caused by chromosomal translocation of t(11;14), t(4;14), t(8;14), del(13), del(17) (among others) (Drach et al., (1998) Blood 92(3): 802-809; Gertz et al., (2005) Blood 106 (8): 2837-2840; Facon et al., (2001) Blood 97 (6): 1566-1571). The main condition of multiple myeloma (MM) is the infinite expansion and enrichment of plasma cells in bone marrow, thereby leading to osteonecrosis. MM-affected patients may experience a variety of disease-related symptoms due to bone marrow infiltration, bone destruction, renal failure, immunodeficiency, and the psychological burden of cancer diagnosis. At present, the main treatments are chemotherapy and stem cell transplantation. The mainly used chemotherapy drugs are steroid, thalidomide, lenalidomide, bortezomib or a combination of various cytotoxic agents. For younger patients, high-dose chemotherapy can be used in combination with autologous stem cell transplantation.

BCMA (B-cell maturation antigen) is B-cell maturation antigen, a type III transmembrane protein consisting of 185 amino acid residues, and belongs to TNF receptor superfamily. The ligand of BCMA belongs to TNF superfamily, such as proliferation-inducing ligand (APRIL), B lymphocyte stimulating factor (BAFF). After binding to its ligand, BCMA activates B cell proliferation and survival. BCMA is specifically and highly expressed on the surface of plasma cells and multiple myeloma cells, but not expressed in hematopoietic stem cells and other normal tissue cells, therefore BCMA can be an ideal target for targeted therapy of MM.

Summing up, there is an urgent need in the art for antibodies specific to BCMA and immune effector cells targeting BCMA.

SUMMARY OF INVENTION

It is an object of the present invention to provide antibodies specific to BCMA and immune effector cells that target BCMA.

In a first aspect, an antibody that targets BCMA is provided in the invention, and the antibody is selected from the group consisting of:

(1) an antibody, comprising a heavy chain variable region comprising HCDR1 as shown in SEQ ID NO: 1, 60 or 62, and/or comprising HCDR2 as shown in SEQ ID NO: 2, 61 or 63, and/or HCDR3 as shown in any one of SEQ ID NO: 3, SEQ ID NO: 4 or SEQ ID NO: 5;

(2) an antibody, comprising a light chain variable region comprising LCDR1 as shown in SEQ ID NO: 6, and/or comprising LCDR2 as shown in SEQ ID NO: 7, and/or comprising LCDR3 as shown in any one of SEQ ID NO: 8, SEQ ID NO: 9 or SEQ ID NO: 10;

(3) an antibody, comprising a heavy chain variable region of the antibody of (1) and a light chain variable region of the antibody of (2);

(4) an antibody, which is a variant of the antibody of any one of (1) to (3) and has the same or similar activity as the antibody of any one of (1) to (3).

In a specific embodiment, the antibody is selected from the group consisting of:

(1) an antibody, comprising HCDR1 as shown in SEQ ID NO: 1, HCDR 2 as shown in SEQ ID NO: 2, HCDR3 as shown in SEQ ID NO: 3, and LCDR1 as shown in SEQ ID NO: 6, LCDR2 as shown in SEQ ID NO: 7 and LCDR3 as shown in SEQ ID NO: 8;

(2) an antibody, comprising HCDR1 as shown in SEQ ID NO: 1, HCDR 2 as shown in SEQ ID NO: 2, HCDR3 as shown in SEQ ID NO: 4, LCDR1 as shown in SEQ ID NO: 6, LCDR2 as shown in SEQ ID NO: 7 and LCDR3 as shown in SEQ ID NO: 9;

(3) an antibody, comprising HCDR1 as shown in SEQ ID NO: 1, HCDR2 as shown in SEQ ID NO: 2, HCDR3 as shown in SEQ ID NO: 5, LCDR1 as shown in SEQ ID NO: 6, LCDR2 as shown in SEQ ID NO: 7 and LCDR3 as shown in SEQ ID NO: 10;

(4) an antibody, comprising HCDR1 as shown in SEQ ID NO: 60, HCDR2 as shown in SEQ ID NO: 61, HCDR3 as shown in SEQ ID NO: 5, LCDR1 as shown in SEQ ID NO: 6, LCDR2 as shown in SEQ ID NO: 7 and LCDR3 as shown in SEQ ID NO: 10;

(5) an antibody, comprising HCDR1 as shown in SEQ ID NO: 62, HCDR2 as shown in SEQ ID NO: 63, HCDR3 as shown in SEQ ID NO: 5, LCDR1 as shown in SEQ ID NO: 6, LCDR2 as shown in SEQ ID NO: 7 and LCDR3 as shown in SEQ ID NO: 10;

(6) an antibody, which is a variant of any one of (1) to (5) and has the same or similar activity as the antibody of any one of (1) to (5).

In a specific embodiment, the antibody is selected from the group consisting of:

(1) an antibody, wherein the heavy chain variable region of the antibody has the amino acid sequence of SEQ ID NO: 13, the amino acid sequence of SEQ ID NO: 17, the amino acid sequence of SEQ ID NO: 21, or the amino acid sequence of SEQ ID NO: 56 or the amino acid sequence of SEQ ID NO: 58;

(2) an antibody, wherein the light chain variable region of the antibody has the amino acid sequence of SEQ ID NO: 11, the amino acid sequence of SEQ ID NO: 15, or the amino acid sequence of SEQ ID NO: 19;

(3) an antibody, comprising a heavy chain variable region of the antibody of (1) and a light chain variable region of the antibody of (2);

(4) an antibody, which is a variant of any one of (1) to (3) and has the same or similar activity as the antibody of any one of (1) to (3).

In a specific embodiment, the antibody is selected from the group consisting of:

(1) an antibody, wherein the heavy chain variable region of the antibody has the amino acid sequence of SEQ ID NO: 13 and the light chain variable region of the antibody has the amino acid sequence of SEQ ID NO: 11;

(2) an antibody, wherein the heavy chain variable region of the antibody has the amino acid sequence of SEQ ID NO:

17 and the light chain variable region of the antibody has the amino acid sequence of SEQ ID NO: 15;

(3) an antibody, wherein the heavy chain variable region of the antibody has the amino acid sequence of SEQ ID NO: 21 and the light chain variable region of the antibody has the amino acid sequence of SEQ ID NO: 19;

(4) an antibody, wherein the heavy chain variable region of the antibody has the amino acid sequence of SEQ ID NO: 56 and the light chain variable region of the antibody has the amino acid sequence of SEQ ID NO: 19;

(5) an antibody, wherein the heavy chain variable region of the antibody has the amino acid sequence of SEQ ID NO: 58 and the light chain variable region of the antibody has the amino acid sequence of SEQ ID NO: 19;

(6) an antibody, which is a variant of any one of (1) to (5) and has the same or similar activity as the antibody of any one of (1) to (5).

In a second aspect, an antibody is provided in the present invention, recognizing the same antigenic determinant as the antibody of the first aspect of the invention.

In a third aspect, a nucleic acid is provided in the present invention, encoding the antibody of the first or second aspect of the invention.

In a fourth aspect, an expression vector is provided in the present invention, comprising the nucleic acid of the third aspect of the invention.

In a fifth aspect, a host cell is provided in the present invention, comprising the expression vector of the fourth aspect of the invention or has the nucleic acid of the third aspect of the invention integrated in the genome.

In a sixth aspect, the use of the antibody of the first or second aspect of the present invention is provided in the present invention, for the preparation of a targeting drug, an antibody drug conjugate or a multifunctional antibody which specifically targets tumor cells expressing BCMA; or for the preparation of an agent for diagnosis of a tumor expressing BCMA; or for the preparation of a chimeric antigen receptor-modified immune cell; and preferably, the immune cell includes T lymphocyte, NK cell or NKT lymphocyte.

In a seventh aspect, a multifunctional immunoconjugate is provided in the present invention, comprising:

an antibody of the first or second aspect of the invention; and a functional molecule linked thereto; said functional molecule being selected from the group consisting of a molecule that targets a tumor surface marker, a molecule that inhibits tumors, a molecule that targets a surface marker of an immune cell, and a detectable label.

In a specific embodiment, the molecule that inhibits tumors is an antitumor cytokine or an antitumor toxin. Preferably, the cytokine comprises: IL-12, IL-15, type I interferon, TNF-alpha.

In a specific embodiment, the molecule that targets a surface marker of an immune cell is an antibody or a ligand that binds to a surface marker of an immune cell; and preferably, the surface marker of an immune cell comprises: CD3, CD16, CD28, and more preferably, the antibody that binds to a surface marker of an immune cell is an anti-CD3 antibody.

In a specific embodiment, the molecule that targets a surface marker of an immune cell is an antibody that binds to a surface marker of a T cell.

In an eighth aspect, a nucleic acid is provided in the present invention, encoding the multifunctional immunoconjugate of the seventh aspect of the invention.

In a ninth aspect, the use of the multifunctional immunoconjugate of the seventh aspect of the present invention is provided in the present invention, for the preparation of an antitumor drug, or for the preparation of an agent for diagnosis of a tumor expressing BCMA; or for the preparation of a chimeric antigen receptor-modified immune cell; and preferably, the immune cell comprises: T lymphocytes, NK cells or NKT lymphocytes.

In a tenth aspect, a chimeric antigen receptor is provided in the present invention, comprising an extracellular domain, a transmembrane domain and an intracellular signal domain, the extracellular domain comprises the antibody of the first or second aspect of the invention, and the antibody preferably is a single-chain antibody or domain antibody.

In a specific embodiment, the intracellular signal domain comprises one or more co-stimulatory signal domains and/or primary signal domains.

In a specific embodiment, the chimeric antigen receptor further comprises a hinge domain.

In a specific embodiment, the transmembrane domain is selected from the group consisting of alpha, beta, zeta chain of TCR, transmembrane regions of CD3ε, CD3ζ, CD4, CD5, CD8α, CD9, CD16, CD22, CD27, CD28, CD33, CD37, CD45, CD64, CD80, CD86, CD134, CD137, CD152, CD154 and PD1; and/or the costimulatory signal domain is selected from the group consisting of intracellular signal regions of CARD11, CD2, CD7, CD27, CD28, CD30, CD40, CD54, CD83, OX40, CD137, CD134, CD150, CD152, CD223, CD270, PD-L2, PD-L1, CD278, DAP10, LAT, NKD2C SLP76, TRIM, FcεRIγ, MyD88 and 41BBL; and/or the primary signal domain is selected from the group consisting of TCR ξ, FcR γ, FcR β, CD3γ, CD3δ, CD3ε, CD5, CD22, CD79a, CD79b, CD278 (also named as "ICOS"), CD66d and CD3ζ, preferably, the transmembrane domain is selected from the group consisting of transmembrane domains of CD8α, CD4, CD45, PD1, CD154 and CD28; and/or the co-stimulatory signal domain is selected from the group consisting of CD137, CD134, CD28 and OX40; and/or the primary signal domain is selected from CD3ζ, most preferably, the transmembrane domain is selected from CD8α or CD28, the co-stimulatory signal domain is selected from the intracellular signal domain of CD137 or CD28, and the primary signal domain is selected from CD3ζ.

In a specific embodiment, the chimeric antigen receptor comprises the following sequentially linked an antibody, a transmembrane region and an intracellular signal region:

the antibody of the first or second aspect of the invention, the transmembrane region of CD8 and CD3ζ;

the antibody of the first or second aspect of the invention, the transmembrane region of CD8, the intracellular signal region of CD137 and CD3ζ;

the antibody of the first or second aspect of the invention, the transmembrane region of CD28, the intracellular signal region of CD28, and CD3ζ; or the antibody of the first or second aspect of the invention, the transmembrane region of CD28, the intracellular signal region of CD28, CD137 and CD3ζ.

In an eleventh aspect, a nucleic acid is provided in the present invention, encoding the chimeric antigen receptor of the tenth aspect of the invention.

In a twelfth aspect, an expression vector is provided in the present invention, comprising the nucleic acid of the eleventh aspect of the invention.

In a thirteenth aspect, a virus is provided in the present invention, comprising the vector of the twelfth aspect of the invention.

In a preferred embodiment, the virus is a lentivirus.

In a fourteenth aspect, the use of the chimeric antigen receptor of the tenth aspect of the present invention, or the nucleic acid of the eleventh aspect of the present invention, or the expression vector of the twelfth aspect of the present invention, or the virus of the thirteenth aspect of the present invention is provided in the present invention, for the preparation of genetically modified immune cells targeting a tumor cell expressing BCMA.

In a preferred embodiment, the tumor expressing BCMA is multiple myeloma.

In a fifteenth aspect, a genetically modified immune cell is provided in the present invention, which is transduced with the nucleic acid of the eleventh aspect of the invention, or the expression vector of the twelfth aspect of the invention or the thirteenth aspect of the invention or the virus of the thirteenth aspect of the present invention; or expresses the chimeric antigen receptor of the tenth aspect of the invention.

The immune cells are preferably selected from T lymphocytes, NK cells or NKT cells.

In a specific embodiment, the genetically modified immune cell further expresses a sequence other than the chimeric antigen receptor of the tenth aspect of the invention, and the other sequence comprises a cytokine, or another chimeric antigen receptor, or a chemokine receptor, or an siRNA that reduces PD-1 expression, or a protein that blocks PD-L1, or a TCR, or a safety switch;

Preferably, the cytokine comprises IL-12, IL-15, IL-21, or type I interferon;

Preferably, the chemokine receptor comprises CCR2, CCR5, CXCR2, or CXCR4;

Preferably, the safety switch comprises iCaspase-9, Truncated EGFR or RQR8.

In a sixteenth aspect, the use of the genetically modified immune cell of the fifteenth aspect of the present invention is provided in the present invention, for preparing a tumor-suppressing drug, and the tumor is a tumor expressing BCMA.

In a preferred embodiment, the tumor expressing BCMA is multiple myeloma.

In a seventeenth aspect, a pharmaceutical composition is provided in the present invention, comprising:

an antibody of the first or second aspect of the invention or a nucleic acid encoding the antibody; or an immunoconjugate of the seventh aspect of the invention or a nucleic acid encoding the immunoconjugate; or a chimeric antigen receptor of the tenth aspect of the invention, or a nucleic acid encoding the chimeric antigen receptor; or a genetically modified immune cell of the fifteenth aspect of the invention.

It is to be understood that the various technical features of the present invention mentioned above and the various technical features specifically described hereinafter (as in the Examples) may be combined with each other within the scope of the present invention to constitute a new or preferred technical solution, which will not be repeated one by one herein.

DESCRIPTION OF FIGURES

FIG. 1 shows SDS electropherograms of BCMA_huFc and BCMA_muFc (reduction conditions).

FIGS. 2-A and 2-B show the expression of BCMA in a stable cell line K562-BCMA detected by FACs. FIG. 2-A shows FACs for mixed clone. FIG. 2-B shows FACs for clones 1-4.

FIG. 3 shows the results of ELISA assays for antibodies 7A12, 7G2 and 23F10.

MODES FOR CARRYING OUT THE INVENTION

Figure 4:
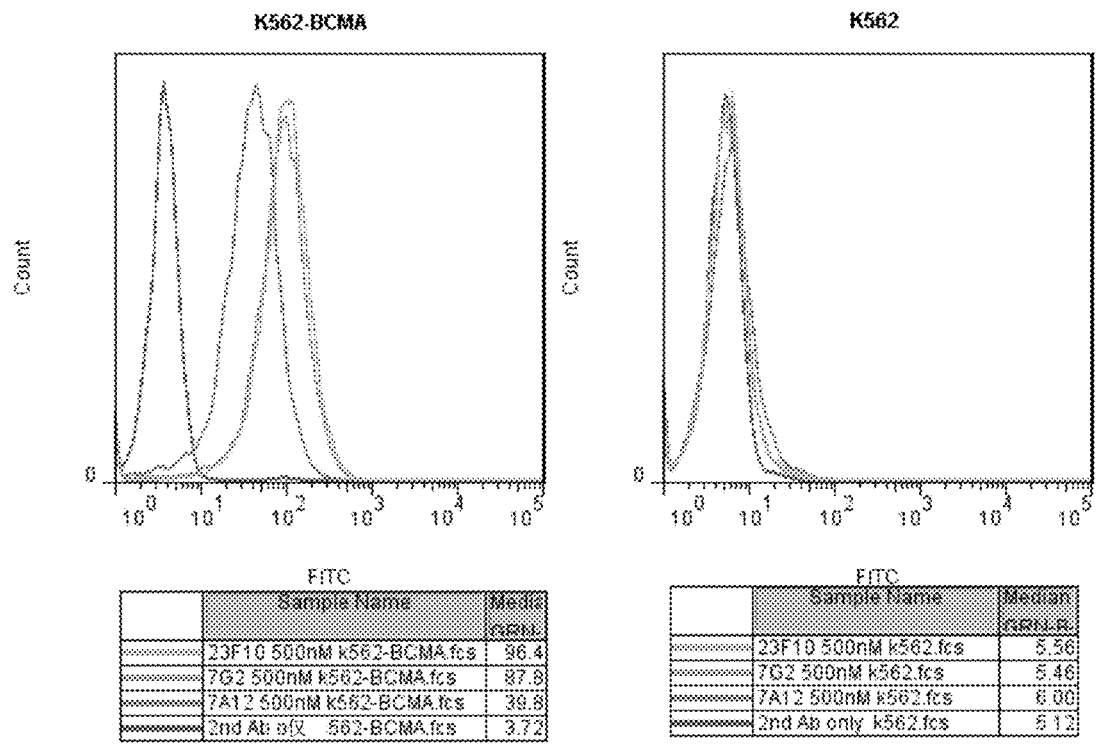
FIG. 4 shows the binding of antibodies 7A12, 7G2 and 23F10 to K562-BCMA and K562 detected by FACs.

Through extensive and intensive research, the inventors have unexpectedly discovered antibodies that specifically bind to BCMA, and these antibodies can be applied to prepare various targeted antitumor drugs and drugs for diagnosing tumors. The present invention has been completed based on the above findings.

The technical terms used herein have the same or similar meanings as conventionally understood by a skilled person. Some terms are defined as follows for understanding the invention.

The term "BCMA" as used herein refers to a B cell maturation antigen, which is a type III transmembrane protein consisting of 184 amino acid residues (NCBI Reference Sequence: NP_001183.2), and the amino acid sequence is shown in SEQ ID No: 37. In a specific embodiment, BCMA refers to human BCMA.

The term "APRIL" as used herein refers to A proliferation-inducing ligand, which is a proliferation-inducing ligand consisting of 184 amino acid residues (NCBI Reference Sequence: NP_003799.1), and belongs to TNF superfamily The term "antibody" as used herein refers to an antigen-binding protein of the immune system. The term "antibody" as used herein includes an intact full length antibody having an antigen binding region and any fragments thereof retaining an "antigen-binding portion" or "antigen-binding region", or a single strand thereof, such as a single chain variable fragment (scFv). A native antibody refers to a glycoprotein comprising at least two heavy (H) chains and two light (L) chains or antigen-binding fragments thereof interconnected by a disulfide bond. The term "antibody" also includes all recombinant forms of antibodies, particularly the antibodies described herein, such as antibodies expressed in prokaryotic cells, unglycosylated antibodies, and antibody fragments that bind to antigens and derivatives hereinafter. Each heavy chain consists of a heavy chain variable region (abbreviated herein as VH) and a heavy chain constant region. Each light chain consists of a light chain variable region (abbreviated herein as VL) and a light chain constant region. VH and VL can be further subdivided into hypervariable regions named complementarity determining regions (CDRs), which are interspersed in more conserved regions named framework regions (FR). Each VH and VL consists of three CDRs and four FRs, from the amino terminus to the carboxy terminus in the following order: FR1, CDR1, FR2, CDR2, FR3, CDR3, FR4. The variable regions of the heavy and light chains contain binding domains that interact with an antigen. The constant region of the antibody can mediate binding of the immunoglobulin to host tissues or factors, including various cells of the immune system (such as effector cells) and the first component (C1q) of the classical complement system.

Antibody fragments include, but are not limited to, (i) Fab fragments consisting of VL, VH, CL and CH1 domains, including Fab' and Fab'-SH, (ii) Fd fragments consisting of VH and CH1 domains, (iii) Fv fragment consisting of VL and VH domains of a single antibody; (iv) a dAb fragment consisting of a single variable region (Ward et al, 1989, Nature 341: 544-546); (v) F(ab')$_2$ fragment, a bivalent fragment comprising two linked Fab fragments; (vi) a single-chain Fv molecule antigen binding site (Bird et al, 1988, Science 242: 423-426; Huston et al, 1988, Proc. Natl. Acad. Sci. USA 85:5879-5883); (vii) bispecific single-chain Fv dimer (PCT/US92/09965); (viii) "dibody" or "tribody", multi-valent or multi-specific fragments constructed by gene fusion (Tomlinson et al, 2000, Methods Enzymol. 326: 461-479; WO94/13804; Holliger et al, 1993, Proc. Natl. Acad. Sci. USA 90:6444-6448); and (ix) scFv genetically fused to identical or different antibodies (Coloma & Morrison, 1997, Nature Biotechnology 15, 159-163).

The term "Fc" or "Fc region" as used herein includes a polypeptide comprising an antibody constant region other than the first constant region immunoglobulin domain. Therefore, Fc refers to the last two constant region immunoglobulin domains of IgA, IgD and IgG, and the last three constant region immunoglobulin domains of IgE and IgM, and flexible hinges at N-terminus of these domains. For IgA and IgM, Fc can include J chain. For IgG, Fc includes hinges between immunoglobulin domains Cγ2 and Cγ3 as well as Cγ1 and Cγ2. Boundaries of Fc region may vary, however, the human IgG heavy chain Fc region is generally defined as comprising residues C226 or P230 at its carboxy terminus, where numbering is based on EU index of Kabat. For human IgG1, Fc is defined herein to include residue P232 to its carboxy terminus, where numbering is based on EU index of Kabat. Fc may refer to the isolated region, or the region in the environment of Fc polypeptide, such as an antibody. The "hinge" as said above includes a flexible polypeptide comprising amino acids between the first and second constant domains of an antibody. Structurally, IgG CH1 domain ends at position EU220 and IgG CH2 domain begins at residue EU237. Therefore, for IgG, the antibody hinge herein is defined to include 221 (D221 of IgG1) to 231 (A231 of IgG1), where the numbering is based on EU index of Kabat.

The term "parent antibody" or "parent immunoglobulin" as used herein includes an unmodified antibody which is to be modified to produce variants. The parent antibody can be a naturally occurring antibody, or a variant or modified version of a naturally occurring antibody. A parent antibody can refer to the antibody itself, a composition comprising the parent antibody, or a nucleic acid sequence encoding the same. The term "parent antibody" or "parent immunoglobulin" as used herein includes a murine or chimeric antibody that is to be modified to produce a humanized antibody.

The term "variant antibody" or "antibody variant" as used herein includes an antibody sequence that differs from the parent antibody sequence by at least one amino acid modification compared with the parent antibody. A variant antibody sequence herein has at least about 80%, preferably at least about 90%, more preferably at least about 95% amino acid sequence identity to the parent antibody sequence. An antibody variant can refer to the antibody itself, a composition comprising the parent antibody, or a nucleotide sequence encoding the same.

The term "variant" as used herein includes an antibody sequence that differs from the parent antibody sequence by at least one amino acid modification compared with the parent antibody. In a specific embodiment, a variant antibody sequence herein has at least about 80%, preferably at least about 90%, more preferably at least about 95%, more preferably at least about 97%, more preferably at least about 98%, most preferably at least about 99% amino acid sequence identity to the parent antibody sequence. An antibody variant can refer to the antibody itself, a composition comprising the parent antibody, or a nucleotide sequence encoding the same. The term "amino acid modification" includes amino acid substitution, addition and/or deletion, and "amino acid substitution" refers to the replacement of an amino acid at a particular position in a parent polypeptide sequence with another amino acid. For example, substitution R94K means that the arginine at position 94 is replaced by lysine, and "amino acid insertion" as used herein refers to the addition of an amino acid at a particular position in a parent polypeptide sequence. As used herein, "amino acid deletion" or "deletion" refers to removal of an amino acid at a particular position in a parent polypeptide sequence.

The term "conservative modification" or "conservative sequence modification" as used herein refers to an amino acid modification that does not significantly affect or alter the binding characteristics of an antibody comprising the amino acid sequence. Such conservative modifications include amino acid substitutions, insertions, and deletions. Modifications can be introduced into the antibodies of the invention by standard techniques known in the art, such as site-directed mutagenesis and PCR-mediated mutagenesis. Conservative amino acid substitutions are substitutions in which amino acid residues are replaced with amino acid residues having similar side chains. A family of amino acid residues having similar side chains has been defined in the art. These families include amino acids containing basic side chains (e.g., lysine, arginine, histidine), acidic side chains (e.g., aspartic acid, glutamic acid), uncharged acute side chains (e.g., glycine, asparagine, serine, threonine, tyrosine, cysteine, tryptophan), non-polar side chains (e.g., alanine, valine, leucine, isoleucine, proline, phenylalanine, methionine), β-branched side chains (e.g., threonine, valine, isoleucine) and aromatic side chains (e.g., tyrosine, phenylalanine, tryptophan, histidine). Therefore, one or more amino acid residues in the CDR regions or the framework regions of the antibody of the present invention can be replaced with amino acid residues of other families with identical side chain, and the function retained by the altered antibody (variant antibody) can be tested.

All positions of immunoglobulin heavy chain constant region discussed in the present invention are numbered based on EU index of Kabat (Kabat et al., 1991, sequences of proteins of immunological interest, 5th edition, United States Public Health Service, National Institutes of Health, Bethesda, incorporated herein by reference in its entirety). "EU index of Kabat" refers to the residue numbering of human IgG1 EU antibody as described by Edelman et al., 1969, Biochemistry 63: 78-85.

The term "antigenic determinant" as used herein, also named as antigenic epitope, may consist of a contiguous sequence of BCMA protein sequence or a discontinuous three-dimensional structure of BCMA protein sequence.

The term "chimeric antigen receptor" or "CAR" as used herein, refers to a polypeptide comprising an extracellular domain capable of binding an antigen, a transmembrane domain, and a cytoplasmic signaling domain (i.e., an intracellular signal domain), and the intracellular signal domain refers to a protein that transmits signals into a cell by producing a second messenger through a defined signaling pathway, thereby regulating cellular activities, or a protein that corresponds to such a messenger and acts as an effector, including a primary signal domain and a functional signaling domain (i.e., a co-stimulatory signal domain) derived from a stimulatory molecule as defined below. The intracellular signal domain produces a signal that promotes the immune effector function of cells of the CAR (e.g., CAR T cells), and examples of immune effector functions, such as in CART cells, includes cell lytic activity and helper activity, including secretion of cytokine.

The term "primary signal domain" refers to modulating the initial activation of a TCR complex in an irritating manner. In one aspect, the primary signal domain is elicited by, for example, binding of a TCR/CD3 complex to a peptide-loaded MHC molecule, thereby mediating a T cell response (including, but not limited to, proliferation, activation, differentiation, etc.). The primary signal domain that functions in a stimulatory manner may comprise an immunoreceptor tyrosine activation motif or a signaling motif of ITAM. Examples of primary signal domains comprising ITAM that are particularly useful in the present invention include, but are not limited to, the sequence derived from TCR ξ, FcRγ, FcRβ, CD3γ, CD3δ, CD3ε, CD5, CD22, CD79a, CD79b, CD278 (also referred to as "ICOS") and CD66d. In an exemplary CAR of the invention, in any one or more of the CARs of the invention, the intracellular signaling domain comprises an intracellular signaling sequence, such as the primary signal domain of CD3ξ.

The term "co-stimulatory signal domain" refers to a "co-stimulatory molecule" which is a related binding partner on a T cell that specifically binds to a co-stimulatory ligand, thereby mediating a co-stimulatory response of a T cell, such as, but not limited to, proliferation. Co-stimulatory molecules are cell surface molecules or ligands thereof which are required for an effective immune response and non-antigen receptors. Co-stimulatory molecules include, but are not limited to, MHC class I molecules, BTLA and Toll ligand receptors, as well as OX40, CD2, CD27, CD28, CD5, ICAM-1, LFA-1 (CD11a/CD18) and 4-1BB (CD137).

In the present invention, in one aspect, the CAR comprises a chimeric fusion protein comprising an extracellular antigen recognition domain, a transmembrane domain and an intracellular signaling domain, and the intracellular signaling domain comprises a functional signaling domain derived from a stimulatory molecule. In one aspect, the CAR comprises a chimeric fusion protein comprising an extracellular antigen recognition domain, a transmembrane domain and an intracellular signaling domain, and the intracellular signaling domain comprises a functional signaling domain derived from a co-stimulatory molecule and a functional signaling domain derived from a stimulatory molecule. In one aspect, the CAR comprises a chimeric fusion protein comprising an extracellular antigen recognition domain, a transmembrane domain and an intracellular signaling domain, and the intracellular signaling domain comprises at least two functional signaling domains derived from one or more co-stimulatory molecules and a functional signaling domain derived from a stimulatory molecule. In one aspect, the CAR comprises an optional leader sequence at the amino acid (ND end) of the CAR fusion protein. In one aspect, the CAR further comprises a leader sequence at N-terminus of the extracellular antigen recognition domain, wherein the leader sequence is optionally cleaved from the antigen recognition domain (e.g., scFv) during processing and localization of the CAR to the cell membrane.

The term "CD3ξ" as used herein is defined as a protein provided by GenBan Accession No. BAG36664.1, or equivalent residues from a non-human species such as a mouse, rodent, monkey, ape, and the like. "CD3ξ domain" as used herein is defined as amino acid residues from the cytoplasmic domain of ξ chain sufficient to functionally deliver the initial signal required for T cell activation. In one aspect, the cytoplasmic domain of ξ comprises residues 52 to 164 of GenBan Accession No. BAG36664.1, a functional ortholog thereof—equivalent residues from non-human species such as a mouse, rodents, monkey, ape, etc.

The term "4-1BB" as used herein refers to a member of TNFR superfamily having the amino acid sequence of GenBank Acc. No. AAA62478.2, or equivalent residues from a non-human species such as a mouse, rodent, monkey, ape and the like. "4-1BB co-stimulatory domain" is defined as amino acid sequence 214-255 of GenBank ACC. No. AAA62478.2, or equivalent residues from non-classified species such as mouse, rodent, monkey, ape, etc. In one aspect, the "4-1BB co-stimulatory domain" is the sequence provided in SEQ ID NO: 35, or equivalent residues from a non-human species such as a mouse, rodent, monkey, ape, and the like.

The term "interferon" as used herein refers to a full-length interferon, or an interferon fragment (truncated interferon) or interferon mutant substantially retaining the biological activities of a full-length wild-type interferon (e.g., retaining at least 80%, preferably at least 90%, more preferably at least 95%, 98% or 99% of those of a full length interferon). Interferons include type I interferons (e.g., interferon α and interferon β) and type II interferons (e.g., interferon γ).

The antibody of the present invention or a variant thereof can be applied to prepare various targeted antitumor drugs as well as drugs for diagnosing tumors, in particular, for preparing immune effector cells targeting BCMA.

Anti-BCMA Antibody

In the present disclosure, antigen binding proteins having an antigen-binding region based on scFv, including antibodies, are described. A recombinant BCMA was used to select scFv from a human scFv phage display library. These molecules display fine specificity. For example, the antibody only recognizes K562 cells stably expressing BCMA and does not recognize K562 cells.

In some embodiments, the invention encompasses an antibody having scFv sequence, which is fused to one or more heavy chain constant regions to form an antibody having a human immunoglobulin Fc region to produce a bivalent protein, thereby increasing overall affinity and stability of an antibody. In addition, the Fe portion allows for direct conjugation of other molecules (including but not limited to fluorescent dyes, cytotoxins, radioisotopes, etc.) to, for example, antibodies used in antigen quantification studies in order to immobilize antibodies for affinity measurement, targeted delivery of therapeutic drugs, use of immune effector cells to test Fc-mediated cytotoxicity and many other applications.

The results presented herein highlight the specificity, sensitivity and utility of the antibodies of the invention in targeting BCMA.

The molecules of the invention are based on single-chain variable fragments (scFv) identified and selected by phage display, the amino acid sequence of which confers specificity to BCMA and forms the basis of all antigen binding proteins of the present disclosure. Therefore, the scFv can be used to design various different "antibody" molecules, including, for example, full length antibodies, fragments thereof such as Fab and F(ab')$_2$, fusion proteins (including scFv_Fc), multivalent antibodies, i.e., an antibody having more than one specificity to the same or different antigens, for example, bispecific T cell-binding antibody (BiTE), tri-antibody, etc. (Cuesta et al, Multivalent antibodies: when design surpasses evolution, Trends in Biotechnology 28: 355-362, 2010).

In one embodiment where the antigen binding protein is a full length antibody, the heavy and light chains of the antibodies of the invention may be of full length (for example, the antibody may comprise at least one, preferably two intact heavy chains, and at least one, preferably two intact light chains), and alternatively may comprise an antigen binding moiety (Fab, F(ab')2, Fv or scFv). In other embodiments, the antibody heavy chain constant region is selected, for example, from IgG1, IgG2, IgG3, IgG4, IgM, IgA1, IgA2, IgD, and IgE. The selection of antibody type will depend on the immune effector function that the designed antibody is intended to elicit. Suitable amino acid sequences for the constant regions of various immunoglobulin isotypes and methods for producing a wide variety of antibodies are known to a skilled person in the construction of recombinant immunoglobulins.

In a first aspect, an antibody or fragment thereof binding to BCMA is provided in the present invention, comprising heavy chain CDR1 comprising an amino acid sequence of any one of SEQ ID NO: 1, 60, 62, and/or heavy chain CDR2 comprising an amino acid sequence of any of SEQ ID NO: 2, 61, 63, and/or heavy chain CDR3 comprising an amino acid sequence of any one of SEQ ID NOs: 3, 4, 5. In another aspect, an antibody or fragment thereof binding to BCMA is provided in the present invention, comprising light chain CDR1 comprising an amino acid sequence of SEQ ID NO: 6, and/or light chain CDR2 comprising an amino acid sequence of SEQ ID NO: 7, and/or light chain CDR3 comprising an amino acid sequence of any of SEQ ID NO: 8, 9, 10. In another aspect, an antibody or fragment thereof binding to BCMA is provided in the present invention, comprising heavy chain CDR1 comprising an amino acid sequence of any one of SEQ ID NO: 1, 60, 62, and/or heavy chain CDR2 comprising an amino acid sequence of any one of SEQ ID NO: 2, 61, 63, and/or heavy chain CDR3 comprising an amino acid sequence of any one of SEQ ID NO: 3, 4, 5, and/or light chain CDR1 comprising an amino acid sequence of SEQ ID NO: 6, and/or light chain CDR2 comprising an amino acid sequence of SEQ ID NO: 7, and/or light chain CDR3 comprising an amino acid sequence of any one of SEQ ID NO: 6, and light chain CDR2 comprising an amino acid sequence of SEQ ID NO: 7, and light chain CDR3 comprising an amino acid sequence of any one of SEQ ID NOs: 8, 9, 10. More preferably, the BCMA-binding antibody or fragment thereof comprises heavy chain CDR1 comprising an amino acid sequence of any one of SEQ ID NO: 1, 60, 62, and heavy chain CDR2 comprising an amino acid sequence of any one of SEQ ID NO: 2, 61, 63, and heavy chain CDR3 comprising an amino acid sequence of any one of SEQ ID NO: 3, 4, 5, and light chain CDR1 comprising an amino acid sequence of SEQ ID NO: 6, and light chain CDR2 comprising an amino acid sequence of SEQ ID NO: 7, and light chain CDR3 comprising an amino acid sequence of any one of SEQ ID NOs: 8, 9, 10.

In another aspect, an antibody or fragment thereof binding to BCMA is provided in the present invention, comprising a heavy chain variable region sequence selected from the group consisting of SEQ ID NOs: 13, 17, 21, 56 and 58.

In another aspect, an antibody or fragment thereof binding to BCMA is provided in the present invention, comprising a light chain variable region sequence selected from the group consisting of SEQ ID NOs: 11, 15 and 19.

Each of the heavy and light chain variable region sequences can bind to BCMA, therefore, the heavy and light chain variable region sequences can be "mixed and matched" to produce anti-BCMA binding molecules of the invention.

In another aspect, variants of an antibody or fragment thereof binding to BCMA is provided in the present invention. Accordingly, an antibody or fragment thereof is provided in the present invention, having a heavy chain and/or light chain variable region that is at least 80% identical to the variable region sequence of the heavy or light chain. Preferably, the amino acid sequence identity of the heavy and/or light chain variable regions is at least 85%, preferably at least 90%, more preferably at least 95%, more preferably 96%, more preferably 97%, even more preferably 98%, the most preferably 99%, including, for example, 80%, 81%, 82%, 83%, 84%, 85%, 86%, 87%, 88%, 89%, 90%, 91%, 92%, 93%, 94%, 95%, 96%, 97%, 98%, 99% and 100%. The variant can be obtained from the antibody described in the present application as a parent antibody by yeast library screening, phage library screening, point mutation or the like. As in the method used in Example 10 of the present application, the antibody 23F10 was used as the parent antibody, and the phage library screening method was used for mutation modification.

In another aspect, an antibody that recognizes the same antigenic determinant as the anti-BCMA antibody described above is provided in the present invention.

Properties of Anti-BCMA Antibody

Standard assays for assessing the binding ability of an antibody, such as an anti-BCMA antibody, are known in the art and include, for example, ELISA, Western blot and flow cytometry analysis. Suitable assays are described in detail in the examples.

Nucleic Acids, Vectors and Host Cells

An isolated nucleic acid encoding an antibody binding to BCMA and fragment thereof, a vector and a host cell comprising the nucleic acid or vector, are also provided in the present invention. The nucleic acid can be present in an intact cell, cell lysate, or can be in a partially purified or substantially purified form.

The nucleic acid of the invention can be obtained using standard molecular biology techniques, for example, standard PCR amplification or cDNA cloning techniques, thereby obtaining cDNA encoding the light and heavy chains of an antibody or encoding VH and VL segments. For antibodies obtained from immunoglobulin gene libraries (e.g., using phage display technology), one or more nucleic acids encoding the antibodies can be recovered from the library. Methods for introducing foreign nucleic acids into host cells are generally known in the art and can vary with the used host cell.

Preferred nucleic acid molecules of the invention are those selected from the group consisting of SEQ ID NOs: 12, 16 and 20 which encode a light chain variable region, and/or those selected from the group consisting of SEQ ID NO: 14, 18, 22, 57 and 59 which encode a heavy chain variable region. A more preferred nucleic acid molecule comprises a sequence of SEQ ID NO: 14 encoding a heavy chain and a sequence of SEQ ID NO: 12 encoding a light chain, or comprises a sequence of SEQ ID NO: 18 encoding a heavy chain and a sequence of SEQ ID NO: 16 encoding a light chain, or comprises a sequence of SEQ ID NO: 22 encoding a heavy chain and a sequence of SEQ ID NO: 20 encoding the light chain, or comprises a sequence of SEQ ID NO: 57 encoding a heavy chain and a sequence of SEQ ID NO: 20 encoding the light chain, or comprises a sequence of SEQ ID NO: 59 encoding a heavy chain and a sequence of SEQ ID NO: 20 encoding the light chain.

For expressing a protein, a nucleic acid encoding an antibody of the invention can be integrated into an expression vector. A variety of expression vectors are available for protein expression. Expression vectors can include self-replicating extra-chromosomal vectors, or vectors integrated into the host genome. Expression vectors used in the present invention include, but are not limited to, those which enable expression of proteins in mammalian cells, bacteria, insect cells, yeast, and in vitro systems. As is known in the art, a variety of expression vectors which are commercially available or otherwise available, can be used in the present invention to express antibodies.

Immunoconjugate

In the present invention, a multifunctional immunoconjugate is also provided, comprising the antibodies described herein and further comprising at least one functional molecule of other type. The functional molecule is selected from, but not limited to, a molecule that targets a tumor surface marker, a tumor-suppressing molecule, a molecule that targets a surface marker of an immune cell, or a detectable label. The antibody and the functional molecule may form a conjugate by covalent attachment, coupling, attachment, cross-linking, or the like.

As a preferred mode, the immunoconjugate may comprise an antibody of the invention and at least one molecule that targets a tumor surface marker or a tumor-suppressing molecule. The tumor-suppressing molecule may be anti-tumor cytokines or anti-tumor toxins. Preferably, the cytokines include but are not limited to IL-2, IL-7, IL-12, IL-15, type I IFN, TNF-alpha. In a specific embodiment, the molecule that targets a tumor surface marker is a molecule that targets the same tumor surface marker as the antibody of the invention. For example, the molecule that targets a tumor surface marker can be an antibody or ligand that binds to a tumor surface marker, for example, can act synergistically with the antibodies of the invention to more precisely target tumor cells.

As a preferred mode, the immunoconjugate may comprise an antibody of the present invention and a detectable label. Such detectable labels include, but are not limited to, fluorescent labels, chromogenic labels such as enzymes, prosthetic groups, fluorescent materials, luminescent materials, bioluminescent materials, radioactive materials, positron-emitting metals and non-radioactive paramagnetic metal ion. More than one marker can also be included. The label used to label the antibody for the purpose of detection and/or analysis and/or diagnosis depends on the used particular detection/analysis/diagnosis technique and/or method, eg, immunohistochemical staining (tissue) samples, flow cytometry, and the like. Suitable labels for detection/analysis/diagnosis techniques and/or methods known in the art are well known to those skilled in the art.

As a preferred mode, the immunoconjugate may comprise: an antibody of the invention and a molecule that targets a surface marker of an immune cell. The molecule targeting a surface marker of a immune cell may be an antibody or a ligand binding to a surface marker of a immune cell, capable of recognizing the immune cell, and carry the antibody of the present invention to the immune cell. The antibody of the present invention can target the immune cell to tumor cells, thereby inducing the immune cell to specifically kill tumors. The immune cell surface marker may be selected from the group consisting of CD3, CD16, CD28, and preferably, the antibody binding to the immune cell surface marker is an anti-CD3 antibody. The immune cells can be selected from the group consisting of T cells, NK cells, and NKT cells.

As a means of chemically generating an immunoconjugate by conjugation, either directly or indirectly (eg, by a linker), the immunoconjugate can be produced as a fusion protein comprising an antibody of the invention and other suitable proteins. The fusion protein can be produced by a method known in the art, for example recombinantly produced by constructing and subsequently expressing the nucleic acid molecule which comprises the nucleotide sequence encoding the antibody in frame with a nucleotide sequence encoding a suitable label.

In another aspect of the invention, a nucleic acid molecule encoding at least one antibody of the invention, a functional variant, or an immunoconjugate thereof is provided. Once obtaining the relevant sequence, the recombination method can be used to obtain the relevant sequence in large quantities. This is usually done by cloning it into a vector, transferring it to a cell, and then isolating the relevant sequence from the proliferating host cells by conventional methods.

The present invention also relates to vectors comprising the appropriate DNA sequences described above as well as appropriate promoters or control sequences. These vectors can be used to transform an appropriate host cell to enable expression of the protein. The host cell may be a prokaryotic cell, such as a bacterial cell; or a lower eukaryotic cell, such as a yeast cell; or a higher eukaryotic cell, such as a mammalian cell.

Chimeric Antigen Receptor Containing Anti-BCMA Antibody

A plurality of chimeric antigen receptors (CAR) are provided in the present invention, comprising an antibody or antibody fragment of the present invention. The CAR T cell exhibits anti-tumor properties. In some embodiments, cells (e.g., T cells) are transduced with a viral vector encoding CAR. In some embodiments, the viral vector is a lentiviral vector. In some embodiments, the cells can stably express CAR.

In a preferred embodiment, the BCMA binding portion of a CAR is a scFv antibody fragment that retains an equivalent binding affinity, for example it binds to the same antigen with comparable efficacy, as compared with the IgG antibody from which it is derived. The antibody fragment is functional, thereby providing a biochemical reaction, which can include, but is not limited to, activating an immune response, inhibiting the initiation of signaling from its target antigen, inhibiting kinase activity, and the like. Accordingly, a BCMA-CAR which comprises a WT1 binding domain and engineered into a T cell, and a method for using it in adoptive immunotherapy are provided in the present invention.

In one aspect, the anti-BCMA antigen binding domain of CAR is a scFv antibody fragment that is humanized relative to the murine sequence scFv from which it is derived.

In one aspect, the CAR of the invention combines the antigen binding domain of a particular antibody with an intracellular signaling molecule. For example, in some aspects, intracellular signaling molecules include, but are not limited to, CD3 ξ chain, 4-1BB and CD28 signaling modules, and combinations thereof.

In one aspect, the BCMA-CAR comprises at least one intracellular signaling domain that is selected from a CD137 (4-1BB) signaling domain, a CD28 signaling domain, a CD3ξ signaling domain, or any combination thereof. In one aspect, the BCMA-CAR comprises at least one intracellular signaling domain derived from one or more co-stimulatory molecules that are not CD137 (4-1BB) or CD28.

Exemplarily, the sequence of BCMA-CAR can be 7A12-BBZ (SEQ ID NO: 75), 25C2-BBZ (SEQ ID NO: 76), 25D2-BBZ (SEQ ID NO: 77), 7G2-BBZ (SEQ ID NO: 78), 7A12-28Z (SEQ ID NO: 79), 7A12-28BBZ (SEQ ID NO: 80), 7G2-28Z (SEQ ID NO: 81), 7G2-28BBZ (SEQ ID NO: 82), 23F10-28Z (SEQ ID NO: 83), 23F10-28BBZ (SEQ ID NO: 84), 25D2-28Z (SEQ ID NO: 85), 25D2-28BBZ (SEQ ID NO: 86). Conventional transmembrane domain and intracellular domain can be selected by a skilled person to replace the transmembrane domain and intracellular domain of the above SEQ ID NO: 75-86, which will fall within the scope of this application.

Chimeric Antigen Receptor Modified T Cell

An immune cell comprising a chimeric antigen receptor of the invention is also provided in the present invention.

In another aspect, the chimeric antigen receptor-modified T cell provided in the present invention further carries an encoding sequence for a foreign cytokine; preferably, the cytokine comprises: IL-12, IL-15 or IL-21. The immune cells are preferably selected from T lymphocytes, NK cells or NKT cells.

In another aspect, the chimeric antigen receptor-modified T cell provided in the present invention further comprise a PD-L1 blocker or a protein that blocks PD-L1, such as native PD-1, or a mutant PD-1 capable of binding to PD-L1, or a fragment of native or mutant PD-1 capable of binding to PD-L1, or an antibody against PD-L1. Exemplarily, the PD-L1 blocker may comprise an amino acid sequence encoded by SEQ ID NO:70.

Pharmaceutical Composition

The antibodies, immunoconjugates comprising the antibodies, and genetically modified immune cells of the present invention can be used in the preparation of a pharmaceutical composition or diagnostic reagent. In addition to an effective amount of the antibody, immunological conjugate, or immune cell, the composition may further comprise a pharmaceutically acceptable carrier. The term "pharmaceutically acceptable" means that when the molecular entities and compositions are properly administered to animals or humans, they do not cause adverse, allergic or other untoward reactions.

Specific examples of some of the substances which may be used as pharmaceutically acceptable carriers or components thereof are sugars, such as lactose, dextrose and sucrose; starches, such as corn starch and potato starch; cellulose and its derivatives, such as carboxymethylcellulose sodium, ethylcellulose and methylcellulose; gum tragacanth; malt; gelatin; talc; solid lubricants such as stearic acid and magnesium stearate; calcium sulfate; vegetable oils, such as peanut oil, cottonseed oil, sesame oil, olive oil, corn oil and cocoa butter; polyhydric alcohols such as propylene glycol, glycerin, sorbitol, mannitol and polyethylene glycol; alginic acid; emulsifiers such as Tween®; wetting agents such as sodium lauryl sulfate; coloring agents; flavoring agents; tablets, stabilizers; antioxidants; preservatives; pyrogen-free water; isotonic saline solutions; and phosphate buffers and the like.

The composition of the present invention can be prepared into various dosage forms as needed, and the dosage to be administered to a patient can be determined by a physician according to factors, such as type, age, body weight, and general disease condition of a patient, mode of administration, and the like. For example, injection or other treatment may be used.

Advantages of the Invention:

1. Specific antibodies against BCMA are provided in the invention;

2. Immune effector cells that target BCMA are provided in the invention; and

3. The antibody of the present invention is capable of efficiently binding to tumor cells expressing BCMA, and the immune effector cells of the present invention exhibit significant killing ability against tumor cells expressing BCMA, and therefore, the antibody and immune effector cells of the present invention can be efficiently and safely applied to the treatment of multiple myeloma, thereby constituting a material foundation for the treatment of multiple myeloma.

The invention will be further illustrated hereinafter in conjunction with specific examples. It is to be understood that the examples are not intended to limit the scope of the invention. The experimental methods in the following examples which do not specify the specific conditions are usually prepared according to conventional conditions such as J. Sambrook et al., Molecular Cloning Experimental Guide, Third Edition, Science Press, 2002, or according to the conditions recommended by the manufacturer.

Example 1. Preparation of BCMA Recombinant Protein a. Construction of BCMA_huFc, BCMA_muFc Expression Plasmid The gene (SEQ ID NO: 39) of extracellular segment of human BCMA, Met1-Ala54 (SEQ ID NO: 38), was in vitro synthesized, inserted into the eukaryotic expression plasmid containing the Fc fragment Asp104-Lys330 of human IgG1 heavy chain constant region, and linked with "GS" to form a fusion expression protein BCMA_huFc (SEQ ID NO: 40), and the corresponding gene sequence is shown in SEQ ID NO: 41.

The gene (SEQ ID NO: 39) of extracellular segment of human BCMA was inserted into the eukaryotic expression plasmid containing Fc fragment Arg100-Lys324 of murine IgG1 heavy chain constant region, and linked with "GS" to form a fusion expression protein BCMA_muFc (SEQ ID NO: 42), and the corresponding gene sequence is shown in SEQ ID NO: 43.

b. Expression of BCMA_huFc, BCMA_muFc by Transient Transfection

1) One day before transfection, $6\text{-}7\times10^5$/ml 293F cells were inoculated in 125 ml culture flasks;

2) On the day of transfection, $3\times10^7$ cells were adjusted in 28 ml FreeStyle™ 293 expression medium;

3) Lipid-DNA complex was prepared by the following steps:

30 ug of DNA was diluted with Opti-MEM I at final volume of 1 ml, and mixed thoroughly;

60 ul of 293Fectin™ was diluted with Opti-MEM I to a final volume of 1 ml and mixed thoroughly;

the mixture was incubated for 5 minutes at room temperature;

4) the diluted DNA was diluted with 293Fectin™ and incubated for 20 minutes at room temperature;

5) 2 ml of DNA-293fectin complex was added to 28 ml of cells, cultured at 37° C., under 8% $CO_2$, 125 rpm for 3-4 days, and the supernatant was collected.

c. Purification of BCMA_huFc, BCMA_muFc

1) The supernatant was centrifuged at 13000 rpm for 15 min;

2) Protein A filler was used in affinity purification with the steps being listed as follows:

Balance: 10 column volumes of balance buffer was used for protein A filler.

Loading: the sample processed with 0.45 μm filter was loaded.

Washing: 20 column volume balance buffer were used for removing impurities until there was no flow-through.

Elution: 10 column volumes of elution buffer were added to elute the protein of interest (6% of neutralization buffer was pre-added to the collection tube).

Solution formulation:

Balance buffer: PBS pH 7.4
Elution buffer: 0.1 M glycine pH 2.6
Neutralize buffer: 1 M Tris 3) The elution was filtered through a 0.22 um membrane, concentrated in a millipore ultrafiltration tube with a cut-off of 10 KD to a volume of 1 ml, and desalted using a PD-Midi desalting column. 1.5 ml of the sample was collected. Protein concentration was measured by OD280/1.47.

2 ug was taken for SDS-PAGE and the results are shown in FIG. 1.

Example 2. Construction of K562-BCMA Stable Cell Line

1. Construction of pWPT-BCMA Packaging Plasmid

The full length gene (SEQ ID NO: 37) of human BCMA was synthesized in vitro, and cleavage sites MluI, SalI (SEQ ID NO: 44) were introduced, which were inserted into the lentiviral packaging plasmid pWPT by double digestion.

2. Packaging of Lentiviruses a) Lenti-x 293T was digested and plated to a 10 cm dish at $8\times10^6$ cells, and cultured at 37° C.

b) The next morning: plasmid/PEI mixture was prepared pWPT-BCMA 5 ug
psPAX.2 7.5 ug
pMD2.G 2.5 ug added into 800 uL of DMEM and incubated. The corresponding PEI volume was 45 uL, and the incubation was carried out for 5 min in 800 uL of OMEM.

c) the plasmid mixture was added dropwise to PEI incubation solution, mixed gently and incubated for 20 min at room temperature.

d) the prepared plasmid/PEI mixture was added dropwise into cells and mixed. The solution was changed after 5 hours.

e) virus supernatant was collected after 72 h, filtered through a 0.45 um filter and temporarily stored at 4° C.

3. BCMA Virus-Infected K562 Cells a) The afternoon of Day 1: well-grown K562 cells were plated at $1\times10^5$ cells to a 6 cm dish.

b) The afternoon of Day 2: supernatant of K562 cells was discarded, 3 mL of fresh complete medium was added, and 1 mL of virus stock solution was added to a final concentration of 6 ug/mL of polybrene.

c) The morning of Day 3: the supernatant was discarded and 5 mL of fresh complete medium was added.

d) The morning of Day 6: some cells were taken for flow detection.

4. Identification of K562-BCMA Mixed Clone a) K562-BCMA mixed clones and K562 negative cells were washed with 1% NCS (PBS containing 1% calf serum) for 2 times and then incubated with primary antibody: huBCMA antibody (abcam, #17323) diluted with 1% NCS at 1:1000 (each 50 uL) and incubated for 50 min at 4° C.

b) Cells were washed twice with 1% NCS and then incubated with secondary antibody: DyLight488-labeled goat anti-rat IgG (abeam, #ab98420), diluted with 1% NCS at 1:200 (each 50 uL), and incubated for 45 min at 4° C.

c) Cells were washed 3 times with 1% NCS and resuspended in 1% NCS and detected using a Guava easyCyte™ HT System instrument. The results are shown in FIG. 2A.

5. K562-BCMA Monoclonal Plating a) Cells in K562-BCMA mixed clone were counted and monoclones were plated by limiting dilution.

b) The growth of clones was observed one week later and the medium was supplemented.

c) Two weeks later, cells in the wells of the monoclonal growth were taken and expanded for culture.

6. Identification of K562-BCMA Monoclone

The detection method was the same as identification of the mixed clone, and the experimental results are shown in FIG. 2B. 4 of the monoclonal clones were BCMA positive clones.

Example 3. Screening for BCMA-Specific scFv Using a Whole Human Phage Display Library The phage display library used in the present invention is a whole human natural scFv phage library constructed by the present company, and has a storage capacity of 1E+11. The scFv fragment highly specific for BCMA was obtained using screening methods known to a skilled person. Briefly, 10 ug/ml antigen BCMA_huFc and human Fc fragment were coated in immunotubes, respectively. To reduce the effect from Fc fragment, the phage library was added to the immunotube coated with human Fc fragment for 1 hr. The supernatant was taken and added to the immunotube coated with BCMA_huFc for 1.5 hours, then the non-specific phage was washed away, and the bound phage was eluted and used to infect *E. coli* TG1 in logarithmic growth phase. The phage eluted was expanded and the expanded phage library was purified using PEG/NaCl precipitation for the next round of screening. Panning was performed for 3-4 cycles to enrich scFv phage clones that specifically bind to BCMA. Positive clones were determined by standard ELISA methods for BCMA_huFc. Human Fc fragment was used as an unrelated antigen in ELISA to verify the specificity of the antibody. A total of 2470 clones were screened, in which 160 clones specifically bound to BCMA_huFc, while did not bind to human Fc fragment in ELISA assays. 76 clones with high signal values were picked for sequencing, and 23 single sequences were obtained. These 23 clones were purified and expressed to obtain three clones specifically binding to K562-BCMA cells (FIG. 4), and the clone were named as 7G2, 7A12 and 23F10. By sequencing analysis, the heavy chain variable region of 7A12 is the amino acid sequence shown in SEQ ID NO: 13, and the light chain variable region is the amino acid sequence shown in SEQ ID NO: 11; the heavy chain variable region of 7G2 is the amino acid sequence shown in SEQ ID NO: 17, and the light chain variable region is the amino acid sequence shown in SEQ ID NO: 15; and the heavy chain variable region of 23F10 is the amino acid sequence shown in SEQ ID NO: 21, and the light chain variable region is the amino acid sequence shown in SEQ ID NO: 19.

```
Amino acid sequence of the heavy chain variable region of 7A12 (SEQ
ID NO: 13):
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCARYPYLA
FDYWGQGTLVTVSS (CDR sequences are shown in bold and underlined)

Nucleotide sequence of the heavy chain variable region of 7A12 (SEQ
ID NO: 14):
GAGGTGCAATTGCTGGAGTCTGGGGGAGGCTTGGTACAGCCTGGGGGG

TCCCTGAGACTCTCCTGTGCAGCCTCCGGATTCACCTTTAGCAGTTATGCCAT

GAGCTGGGTCCGCCAGGCTCCAGGGAAGGGGCTGGAGTGGGTCTCAGCTATT

AGTGGTAGTGGTGGTAGCACATACTACGCAGACTCCGTGAAGGGCCGGTTCA

CCATCTCCAGAGACAATTCCAAGAACACGCTGTATCTGCAGATGAACAGCCT

GAGAGCCGAGGACACGGCCGTATATTACTGTGCGCGTTACCCATACCTGGCA

TTCGACTACTGGGGCCAAGGAACCCTGGTCACCGTCTCGAGT

Amino acid sequence of the light chain variable region of 7A12 (SEQ
ID NO: 11)
EIVLTQSPGTLSLSPGERATLSCRASQSVSSSYLAWYQQKPGQAPRLLIYGA
SSRATGIPDRFSGSGSGTDFTLTISRLEPEDFAVYYCQQYGYPPSYTFGQGTKVEI
K (CDR sequences are shown in bold and underlined)

Nucleotide sequence of the light chain variable region of 7A12 (SEQ
ID NO: 12):
GAAATCGTGTTAACGCAGTCTCCAGGCACCCTGTCTTTGTCTCCAGGGG

AAAGAGCCACCCTCTCTTGCAGGGCCAGTCAGAGTGTTAGCAGCAGCTACTT

AGCCTGGTACCAGCAGAAACCTGGCCAGGCTCCCAGGCTCCTCATCTATGGA

GCATCCAGCAGGGCCACTGGCATCCCAGACAGGTTCAGTGGCAGTGGATCCG

GGACAGACTTCACTCTCACCATCAGCAGACTGGAGCCTGAAGATTTTGCAGT

GTATTACTGTCAGCAGTACGGTTACCCACCATCTTACACGTTCGGCCAGGGG

ACCAAAGTGGAAATCAAA

Amino acid sequence of the heavy chain variable region of 7G2 (SEQ
ID NO: 17):
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKLSGDA
AMDYWGQGTLVTVSS (CDR sequences are shown in bold and underlined)

Nucleotide sequence of the heavy chain variable region of 7G2 (SEQ
ID NO: 17):
GAGGTGCAATTGCTGGAGTCTGGGGGAGGCTTGGTACAGCCTGGGGGG

TCCCTGAGACTCTCCTGTGCAGCCTCCGGATTCACCTTTAGCAGTTATGCCAT

GAGCTGGGTCCGCCAGGCTCCAGGGAAGGGGCTGGAGTGGGTCTCAGCTATT

AGTGGTAGTGGTGGTAGCACATACTACGCAGACTCCGTGAAGGGCCGGTTCA

CCATCTCCAGAGACAATTCCAAGAACACGCTGTATCTGCAGATGAACAGCCT

GAGAGCCGAGGACACGGCCGTATATTACTGTGCGAAACTGTCTGGTGATGCA

GCAATGGACTACTGGGGCCAAGGAACCCTGGTCACCGTCTCGAGT
```

-continued

Amino acid sequence of the light chain variable region of 7G2 (SEQ ID NO: 15):
EIVLTQSPGTLSLSPGERATLSCRASQSVSSSYLAWYQQKPGQAPRLLIY**GA
SSRATGIPDRFSGSGSGTDFTLTISRLEPEDFAVYYCQQYGYPPRYT**FGQGTKVEI
K (CDR sequences are shown in bold and underlined)

Nucleotide sequence of the light chain variable region of 7G2 (SEQ ID NO: 16):
GAAATCGTGTTAACGCAGTCTCCAGGCACCCTGTCTTTGTCTCCAGGGG

AAAGAGCCACCCTCTCTTGCAGGGCCAGTCAGAGTGTTAGCAGCAGCTACTT

AGCCTGGTACCAGCAGAAACCTGGCCAGGCTCCCAGGCTCCTCATCTATGGA

GCATCCAGCAGGGCCACTGGCATCCCAGACAGGTTCAGTGGCAGTGGATCCG

GGACAGACTTCACTCTCACCATCAGCAGACTGGAGCCTGAAGATTTTGCAGT

GTATTACTGTCAGCAGTACGGTTACCCACCAAGATACACGTTCGGCCAGGGG

ACCAAAGTGGAAATCAAA

Amino acid sequence of the heavy variable region of 23F10 (SEQ ID NO: 21):
EVQLLESGGGLVQPGGSLRLSCAASGFTFSSYAMSWVRQAPGKGLEWVS**A
ISGSGGSTYYADSVKGRFTISRDNSKNTLYLQMNSLRAEDTAVYYCAKVRPFW
GTFDY**WGQGTLVTVSS (CDR sequences are shown in bold and underlined)

Amino acid sequence of the heavy chain variable region of 23F10 (SEQ ID NO: 22):
GAGGTGCAATTGCTGGAGTCTGGGGGAGGCTTGGTACAGCCTGGGGGG

TCCCTGAGACTCTCCTGTGCAGCCTCCGGATTCACCTTTAGCAGTTATGCCAT

GAGCTGGGTCCGCCAGGCTCCAGGGAAGGGGCTGGAGTGGGTCTCAGCTATT

AGTGGTAGTGGTGGTAGCACATACTACGCAGACTCCGTGAAGGGCCGGTTCA

CCATCTCCAGAGACAATTCCAAGAACACGCTGTATCTGCAGATGAACAGCCT

GAGAGCCGAGGACACGGCCGTATATTACTGTGCGAAAGTTCGTCCATTCTGG

GGTACTTTCGACTACTGGGGCCAAGGAACCCTGGTCACCGTCTCGAGT

Amino acid sequence of the heavy chain variable region of 23F10 (SEQ ID NO: 19):
EIVLTQSPGTLSLSPGERATLSCRASQSVSSSYLAWYQQKPGQAPRLLIY**GA
SSRATGIPDRFSGSGSGTDFTLTISRLEPEDFAVYYCQQYFNPPEY**TFGQGTKVEI
K (CDR sequences are shown in bold and underlined)

Amino acid sequence of the heavy chain variable region of 23F10 (SEQ ID NO: 20):
GAAATCGTGTTAACGCAGTCTCCAGGCACCCTGTCTTTGTCTCCAGGGG

AAAGAGCCACCCTCTCTTGCAGGGCCAGTCAGAGTGTTAGCAGCAGCTACTT

AGCCTGGTACCAGCAGAAACCTGGCCAGGCTCCCAGGCTCCTCATCTATGGA

GCATCCAGCAGGGCCACTGGCATCCCAGACAGGTTCAGTGGCAGTGGATCCG

GGACAGACTTCACTCTCACCATCAGCAGACTGGAGCCTGAAGATTTTGCAGT

GTATTACTGTCAGCAGTACTTCAACCCACCAGAATACACGTTCGGCCAGGGG

ACCAAAGTGGAAATCAAA

Figure 5:
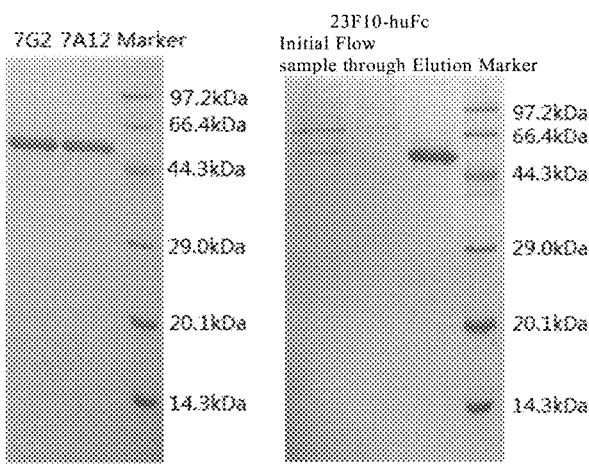
FIG. 5 shows analysis of purified anti-BCMA scFv_Fc antibody by SDS PAGE (reduction conditions).

Example 4. Construction of Anti-BCMA scFv_Fc Fusion Antibody and Transient Expression, Purification and Activity Identification Thereof in Eukaryotic Cells Primers were designed for VH and VL fragments of 7G2, 7A12, 23F10, respectively, and a (Gly$_4$Ser)$_3$ linker consisting of 15 flexible amino acids was introduced to form a scFv; a NheI cleavage site and protective bases were introduced upstream to VH, and a BamHI cleavage site and protective bases were introduced downstream to VL. The PCR product was analyzed by 1% agarose gel electrophoresis, purified and recovered. After digestion, it was ligated into V152 eukaryotic expression vector (purchased from Shanghai Ruijin Biotechnology Co., Ltd.). 293F cells in logarithmic growth phase were transiently transfected with 293Fectin™ Transfection reagent (Invitrogen, 12347-019) or polyethyleneimine (PEI) (Sigma-Aldrich, 408727). At 5-7 days after transfection, the supernatant was collected and subjected to affinity purification of Protein A. The obtained antibodies were quantitatively and qualitatively analyzed by SDS PAGE (FIG. 5).

Figure 6:
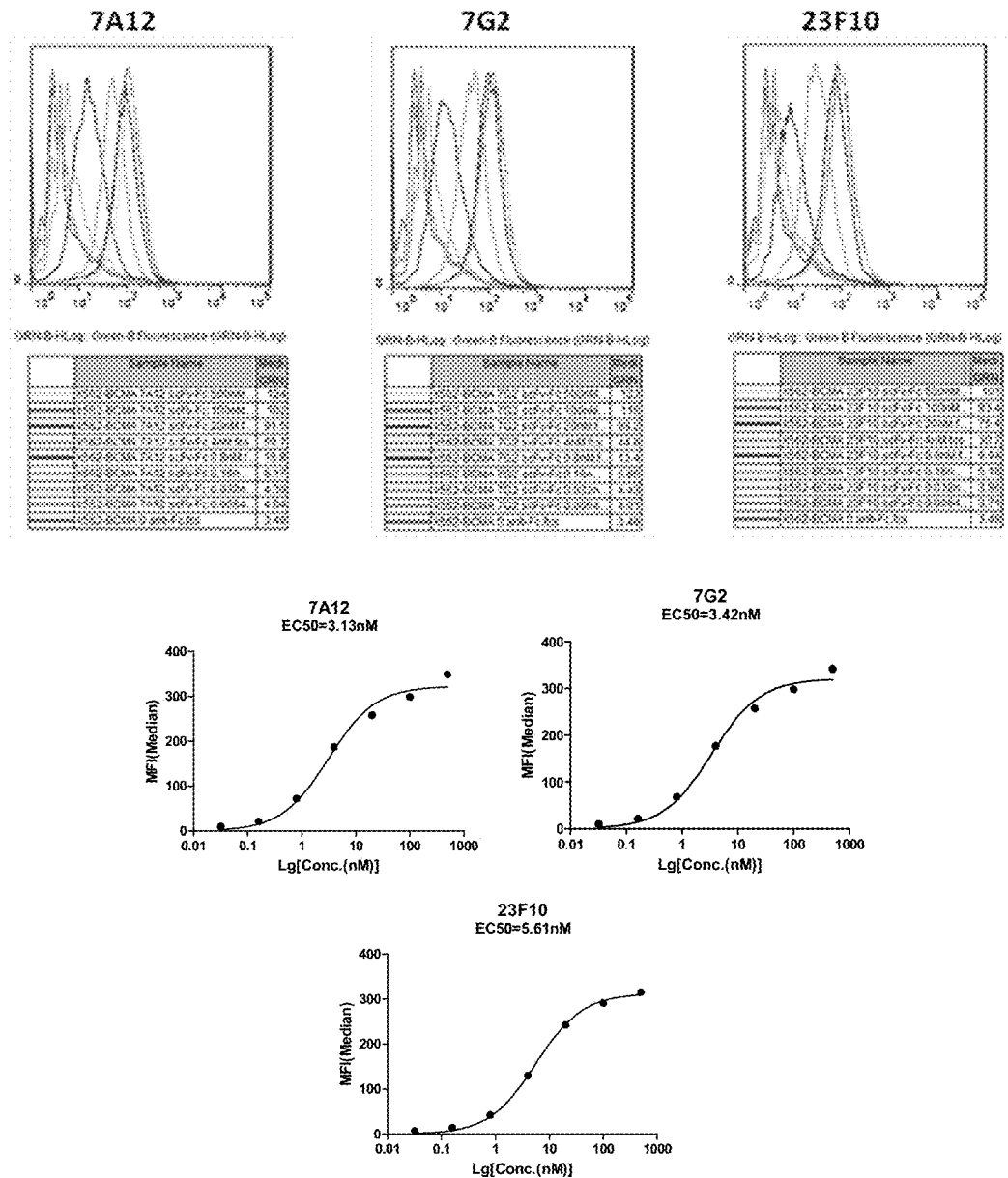
FIG. 6 shows the binding of gradient-diluted purified scFv_Fc to K562-BCMA determined by FACs assay.

The binding of the antibody to K562 stably expressing BCMA was tested by flow cytometry. The method for FACs detection is as follows: cells were harvested, washed once with growth medium, and resuspended in PBS. The cell concentration was adjusted to 4E+5 cells/ml. The gradient-diluted scFv_Fc fusion antibody was incubated with the cells for 30 minutes on ice, the initial concentration of the antibody was 500 nM, which was 5-fold diluted for 7 gradients in total. Thereafter, the antibody was incubated with FITC-labeled anti-mouse IgG secondary antibody, and, after washed twice, detected using Guava easyCyte™ HT System. FIG. 6 shows the binding of scFv_Fc fusion forms of antibody 7A12, 7G2 and 23F10 to K562-BCMA. All the three antibodies exhibited a concentration-dependent binding with an EC50 of 3.13 nM, 3.42 nM and 5.61 nM, respectively.

Example 5. Determination of Antibody Affinity Using Surface Plasmon Resonance (SPR)

Figure 7A:
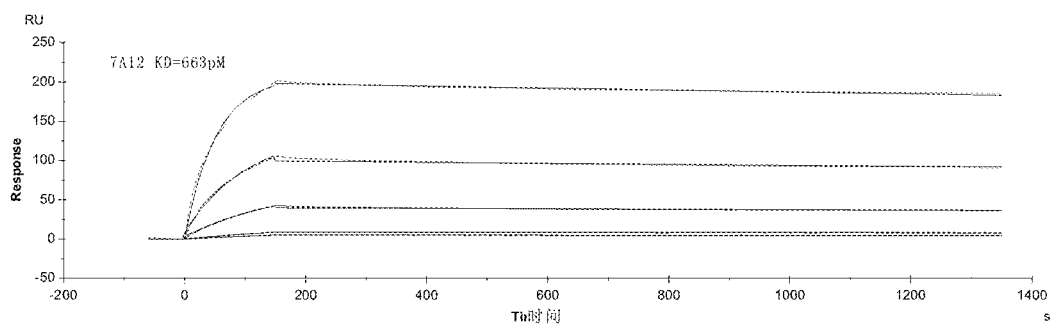
FIG. 7 shows the affinity of antibodies 7A12, 7G2 and 23F10 to BCMA determined by Biacore.
Figure 7B:
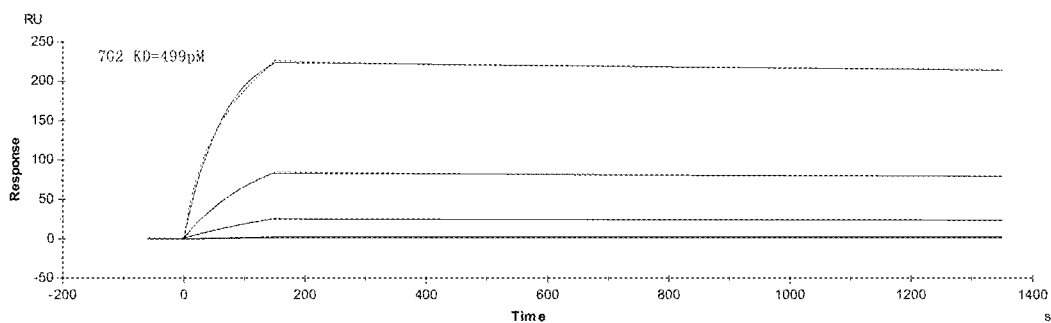
Figure 7C:
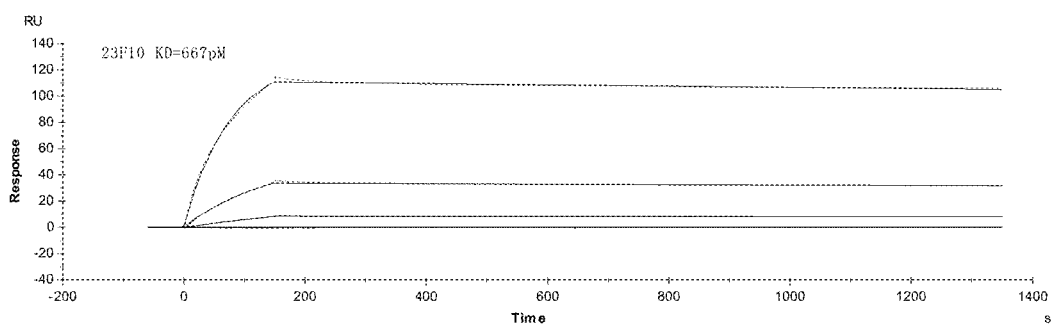

The affinities of different antibodies to BCMA were determined using biacore T200. The used method was as follows:

BCMA_huFc was coated on a CM5 chip by amino coupling to about 500 RU, and the gradient-diluted antibody as a mobile phase was passed through the antigen-coated channel at a flow rate of 30 ul/min. The running buffer was HBS-N and the temperature was 25° C. The experimental data was analyzed by BIAevaluation 3.2 and the kinetic curves were fitted using 1:1 langmuir model. KD of 7A12 (scFv_Fc) was 663 pM, KD of 7G2 (scFv_Fc) was 499 pM, and KD of 23F10 (scFv_Fc) was 667 pM (see FIG. 7). The parameters are shown in the following table:

| Clone | ka (1/Ms) | kd (1/s) | KD (M) |
|---|---|---|---|
| 7G2 | 7.52E+04 | 3.75E−05 | 4.99E−10 |
| 7A12 | 9.84E+04 | 6.53E−05 | 6.63E−10 |
| 23F10 | 6.64E+04 | 4.43E−05 | 6.67E−10 |

Example 6. Determination of Binding of Antibodies to Tumor Cell Lines by FACs

Figure 8:
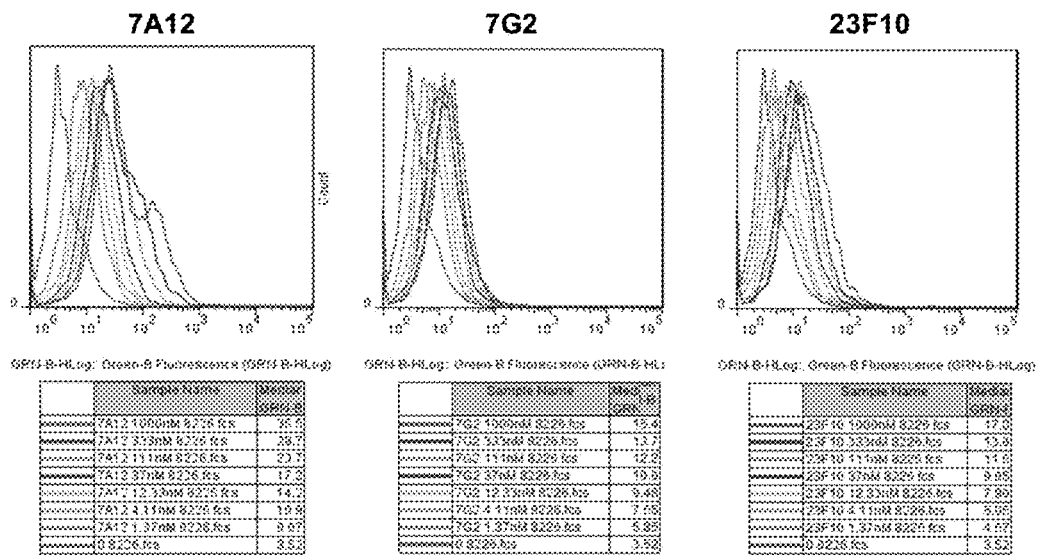
FIG. 8 shows the binding of antibodies 7A12, 7G2 and 23F10 to RPMI8226 cell line determined by FACs.

RPMI8226 is a peripheral blood B lymphocyte of human multiple myeloma. The method for FACs detection is as follows: cells were harvested, washed once with growth medium, and resuspended in PBS. The cell concentration was adjusted to 4E+5 cells/ml. The gradient-diluted scFv_Fc fusion antibody was incubated with the cells for 30 minutes on ice, and the initial concentration of the antibody was 500 nM, and 5-fold diluted for 7 gradients in total. Thereafter, the antibody was incubated with a FITC-labeled anti-mouse IgG secondary antibody, and, after washed twice, detected by Guava easyCyte™ HT System. FIG. 8 shows the concentration-dependent binding of scFv_Fc fusion forms of antibody 7A12, 7G2 and 23F10 on cell line RPMI8226.

Example 7. Competitive Binding Assay of Anti-BCMA Antibody to BCMA Ligand APRIL

1. Expression of Purified Recombinant APRIL Fusion Protein

The fusion protein of human APRIL His115-Leu250 and Fc fragment Asp104-Lys330 of human IgG1 heavy chain constant region linked by "GS" was recombinantly expressed. The fusion protein APRIL_huFc (SEQ ID NO: 45), the corresponding gene sequence was SEQ ID NO: 46. Transient transfection, expression and purification were performed as described in Example 1.

2. Competitive ELISA

A ELISA plate was coated with 50 ng/ml 100 ul/empty BCMA_muFc at 4° C. overnight. On the next day, the plate was washed with PBS for 3 times, and PBS containing 2% skim milk powder was added and blocked at room temperature for 1 hour. 40 ng/ml APRIL_huFc and gradient-diluted antibody 7A12, 7G2 or 23F10 (starting concentration 200 nM, 3-fold dilution, 7 gradients) were simultaneously added. The resulted mixture was incubated for 1 hour at room temperature, washed for three times with PBST, and three times with PBS. A 1:1000 dilution of HRP-labeled mouse anti-human Fc antibody was added, incubated for 1 hour at room temperature, and washed three times with PBST, and three times with PBS. TMB was added for development and read with a microplate reader.

Figure 9:
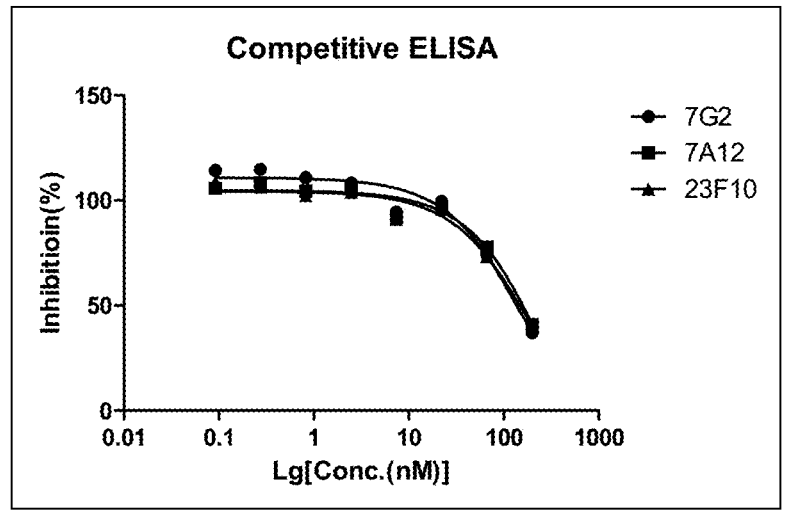
FIG. 9 shows the competitive binding of antibodies and APRIL to BCMA determined by ELISA.

The experimental results are shown in FIG. 9. All of 7A12, 7G2 and 23F10 can significantly inhibit the binding of APRIL to BCMA, which demonstrates that the antibodies of the invention can inhibit the binding of BCMA to its natural ligand.

Example 8. Construction of Anti-BCMA Chimeric Antigen Receptor Plasmid (CAR)

a. Construction of Anti-BCMA Antibody 7A12 Chimeric Antigen Receptor Plasmid

Lentiviral plasmids expressing the second and third generation chimeric antigen receptors of antibody 7A12 were constructed using PRRLSIN-cPPT.EF-1α as a vector, including PRRLSIN-cPPT.EF-1α-7A12-28Z, PRRLSIN-cPPT.EF-1α-7A12-BBZ and PRRLSIN-cPPT.EF-1α-7A12-28BBZ. 7A12-28Z sequence consists of CD8α signal peptide (SEQ ID NO: 23), 7A12 scFv (SEQ ID NO: 47), CD8 hinge (SEQ ID NO: 25), CD28 transmembrane region (SEQ ID NO: 27), intracellular signaling domain (SEQ ID NO: 29) and intracellular segment CD3ξ (SEQ ID NO: 31) of CD3; 7A12-BBZ sequence consists of CD8α signal peptide (SEQ ID NO: 23), 7A12 scFv (SEQ ID NO: 47), CD8 hinge (SEQ ID NO: 25), transmembrane region (SEQ ID NO: 33), CD137 intracellular signaling domain (SEQ ID NO: 35) and CD3ξ (SEQ ID NO: 31); 7A12-28BBZ sequence consists of CD8α signal peptide (SEQ ID NO: 23), 7A12-scFv (SEQ ID NO: 47), CD8 hinge (SEQ ID NO: 25), CD28 transmembrane region (SEQ ID NO: 27), intracellular segment (SEQ ID NO: 29), CD137 intracellular signaling domain (SEQ ID NO: 35) and CD3ξ (SEQ ID NO: 31).

b. Construction of Plasmid for Chimeric Antigen Receptor of Anti-BCMA Antibody 7G2

Lentiviral plasmids expressing the second and third generation chimeric antigen receptors of antibody 7G2 were constructed using PRRLSIN-cPPT.EF-1α as a vector, including PRRLSIN-cPPT.EF-1α-7G2-28Z, PRRLSIN-cPPT.EF-1α-7G2-BBZ and PRRLSIN-cPPT.EF-1α-7G2-28BBZ. 7G2-28Z sequence consists of CD8α signal peptide (SEQ ID NO: 23), 7G2 scFv (SEQ ID NO: 48), CD8 hinge (SEQ ID NO: 25), CD28 transmembrane region (SEQ ID NO: 27), intracellular signaling domain (SEQ ID NO: 29) and intracellular segment CD3ξ (CD ID NO: 31) of CD3; 7G2-BBZ sequence consists of CD8α signal peptide (SEQ ID NO: 23), 7G2 scFV (SEQ ID NO: 48)), CD8 hinge (SEQ ID NO: 25), transmembrane region (SEQ ID NO: 33), CD137 intracellular signaling domain (SEQ ID NO: 35) and CD3ξ (SEQ ID NO: 31); 7G2-28BBZ sequence consists of CD8α signal peptide (SEQ ID NO: 23), 7G2-scFv (SEQ ID NO: 48), CD8 hinge (SEQ ID NO: 25), CD28 transmembrane region (SEQ ID NO: 27), intracellular segment (SEQ ID NO: 29), CD137 intracellular signaling domain (SEQ ID NO: 35) and CD3ξ (SEQ ID NO: 31).

Example 9. Preparation of CAR-T Cells

1. Lentiviral Packaging, Virus Concentration and Titer Determination of Lentiviral Vector of CAR Targeting BCMA a. Lentiviral Packaging 1) 293T cells were inoculated in a 10 cm cell culture dish, and cultured overnight at 37° C., 5% $CO_2$ for transfection, and the medium was DMEM containing 10% fetal bovine serum (Gibico);

2) 5.4 μg of target gene plasmid PRRLSIN-cPPT.EF-1α-EGFP (Mock) or related CAR plasmid and 6.2 μg of packaging plasmid pRsv-REV, 6.2 μg of RRE-PMDLg, 2.4 μg of Vsvg were dissolved in 800 μL blank DMEM medium and mixed;

3) 60 μg of PEI was dissolved in 800 μl of serum-free DMEM medium, mixed gently (or vortexed at 1000 rpm for 5 seconds), and incubated for 5 min at room temperature;

4) Formation of transfection complex: the plasmid mixture was added to PEI mixture, and immediately after the addition, the mixture was vortexed or gently mixed, and incubated at room temperature for 20 min;

5) 1.6 ml of transfection complex was added to a 10 cm culture dish containing 11 ml of DMEM medium (unnecessary to change the medium); after 4-5 hours, the transfected 293T cells were exchanged with DMEM medium containing 10% FBS and incubated for 72 h at 37° C. and the viral supernatant was collected.

b. Lentivirus Concentration

1) Preparation of 5×PEG8000 NaCl: 8.766 g of NaCl and 50 g of PEG8000 were weighed and dissolved in 200 ml Milli-Q pure water; sterilized at 121° C. for 30 min; and stored at 4° C.;

2) Lentiviral supernatant was filtered with a 0.45 μm filter; 7.5 ml of 5×PEG-8000 NaCl stock solution was added per 30 ml of the filtered virus initial solution; mixed once every 20 to 30 minutes for 3-5 times; placed at 4° C. overnight; and centrifuged at 4° C., 4000 g for 20 min;

3) The supernatant was aspirated and discarded, the tube was placed for 1 to 2 minutes, and the residual liquid was aspirated and discarded; an appropriate amount of lentivirus solution was added to dissolve the lentiviral precipitate; and dispensed and stored at −80° C.

c. Titer Determination of Lentiviral 1) 293T cells were inoculated in a 6-well culture plate at $2\times10^5$ cells, 1 ml/well; 10 μg/μl (initial concentration) polybrene solution was added at 0.6 μl/ml to a final concentration of 6 μg/ml; cultured at 37° C., 5% $CO_2$ for 1 hours, and the medium was DMEM containing 10% fetal bovine serum;

2) virus concentrate was added at 10 μL/well, 5-fold dilution, 3 gradients, and cultured at 37° C., 5% $CO_2$;

3) After 72 hours of infection, trypsin was used to digest (30 s) 293T cells, 1 ml DMEM (10% FBS) was added to quench digestion, the cell suspension was transferred into a 2 ml centrifuge tube (two aliquots), centrifuged at 5000 rpm for 5 min, and the supernatant was discarded; the cells were washed twice with PBS (2% NBS);

4) 50 μl of PE-SA (1:200 dilution) antibody was added into cells in Control group, incubated for 45 min on ice, washed twice with PBS (2% NBS), and resuspended as a control;

5) 50 μl of 1:50 diluted biotin-Goat anti human IgG, F(ab')2 antibody was added into cells in Test group cells, incubated on ice for 45 min; and washed twice with PBS (2% NBS); 50 μl of PE-SA (1:200 dilution) antibody was added and incubated on ice for 45 min;

6) 2 ml of PBS (2% NBS) was added to resuspend the cells, and centrifuged at 4° C., 5000 rpm/min for 5 minutes; the supernatant was discarded; which was repeated twice;

7) 500 μl of PBS (2% NBS) was added and transferred to a flow tube. PE channel was detected by a flow cytometry, and the number of cells with a positive rate of 5-20% was appropriate. Titer (PFUs/mL)=cell number×positive rate/virus volume was calculated.

2. Lentiviral-Transduced T Lymphocyte—Preparation of CAR-Positive T Lymphocytes

1) Activation of T lymphocyte: lymphocytes were added into a lymphocyte culture medium at a density of about $1\times10^6$/mL, and magnetic beads (Invitrogen) coated with anti-CD3 and CD28 antibodies at a magnetic bead:cell ratio of 2:1 and recombinant human IL-2 (Shanghai Huaxin Biotech Co., Ltd.) at a final concentration of 500 U/mL were simultaneously added and incubated for 48 h;

2) One day before infection, a 24-well plate was coated by Retronectin at a final concentration of 5 μg/ml, and incubated overnight at 4° C.;

3) the retronectin solution (PBS) in the 24-well plate was discarded and the plate was washed twice with 1 ml of PBS;

4) the concentrated lentivirus was added to PBMCs cells at MOI=10, centrifuged at 1000 g for 40 min, and transferred to a cell incubator;

5) Amplification: The infected cells were passaged every other day at a density of $5\times10^5$/mL, and recombinant human IL-2 at a final concentration of 500 U/mL was supplemented in the lymphocyte culture solution.

3. Expression of Chimeric Antigen Receptor of T Lymphocyte

1) On the day 7 of culture, $1\times10^6$ of lentivirus-infected T lymphocytes were taken in a centrifuge tube;

2) the T cells were centrifuged at 4° C., 5000 rpm for 5 min, the supernatant was discarded, and the residue was washed twice with PBS;

3) 50 μl of biotin-Goat anti human IgG, F(ab')2 antibody (1:50 dilution) were added into the cells to be tested, incubated for 45 min on ice; washed twice with PBS (2% NBS); and 50 μl of PE-SA (1:200 dilution) antibody was added and incubated on ice for 45 min;

4) 2 ml of PBS (2% NBS) was added to resuspend the cells and centrifuged at 4° C., 5000 rpm/min for 5 minutes, the supernatant was discarded; which was repeated twice;

5) 500 μl of PBS (2% NBS) was added and transferred to a flow tube. PE channel was detected by a flow cytometry to determine the proportion of CAR-positive T cells.

Figure 10:
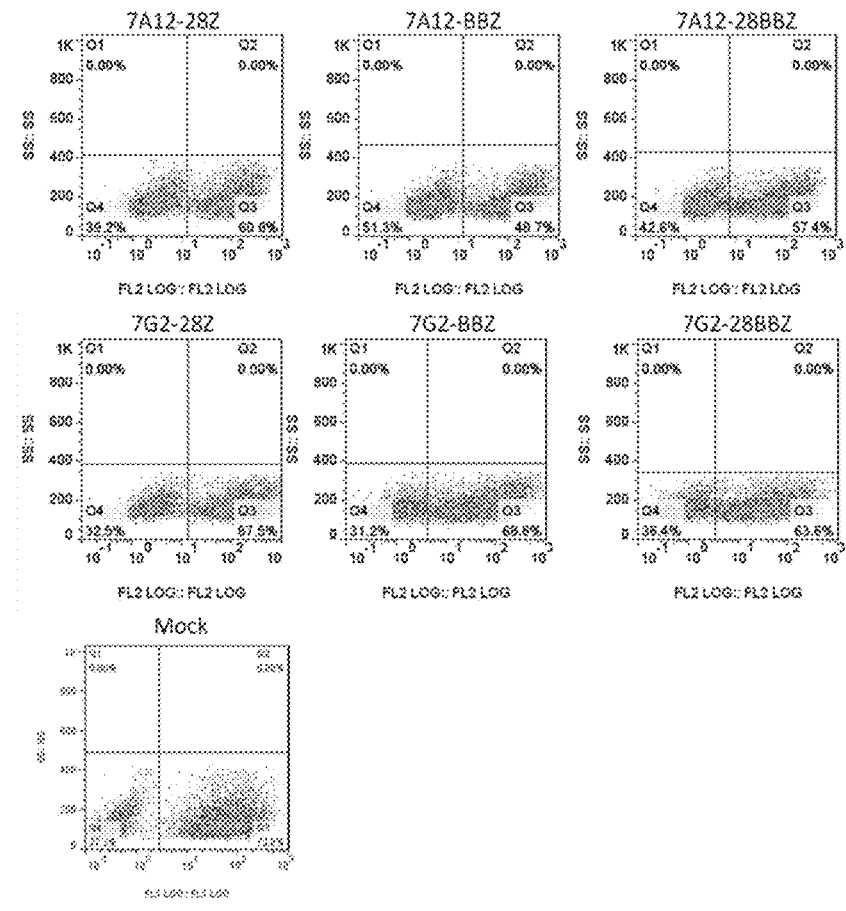
FIG. 10 shows the positive rate of BCMA-CAR T virus-infected T lymphocytes detected by FACS.

The positive infection rates of Mock, 7A12-28Z, 7A12-BBZ, 7A12-28BBZ, 7G2-28Z, 7G2-BBZ and 7G2-28BBZ T cell in the in vitro toxicity killing experiment are shown in FIG. 10, which are 72.8%, 60.8%, 48.7%, 57.4%, 67.5%, 68.8%, 63.6%, respectively.

4. Cytotoxicity Assay of CAR T Cells Targeting BCMA

CytoTox 96 non-radioactive cytotoxicity assay kit (Promega) was used with reference to the instructions of Cyto-Tox 96 non-radioactive cytotoxicity assay kit.

Target cells: 75 μl of $2\times10^5$/mL K562, K562-BCMA and RPMI-8226 cells were inoculated into 96 well plates, respectively. Effector cells: T-Mock and CAR T cells expressing different chimeric antigen receptors were added at an effector target ratio of 3:1, 1:1 or 1:3. Quadruplicate wells were set for each group, and the average of 4 replicate wells was taken. The detection time was hour 18 of incubation of the cells. Each experimental group and each control group are as follows:

Each experimental group: each target cell+CAR T expressing different chimeric antigen receptors;

Control group 1: maximum release of LDH from target cells;

Control group 2: spontaneous release of LDH from target cells;

Control group 3: spontaneous release of LDH from effector cells;

The cytotoxicity calculation formula is: cytotoxicity %=[(experimental group−effector cell control−target cell control)/(target cell maximum−target cell control)]×100%.

Figure 11A:
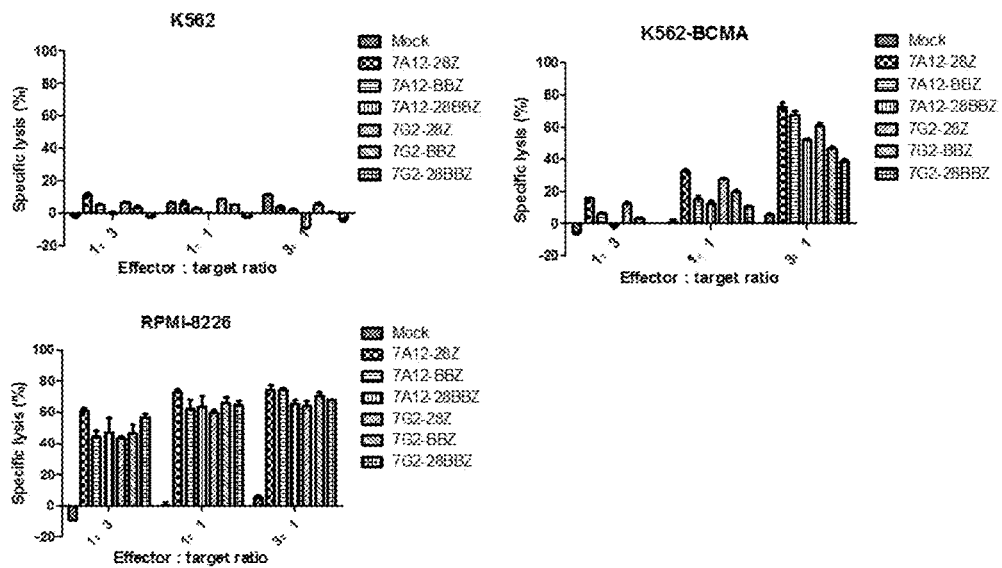
FIG. 11A shows the results of in vitro toxicity tests of BCMA-CAR T on BCMA-expression positive and negative cells.

The results showed that each of the CAR T cells expressing different chimeric antigen receptors had significant in vitro killing activities against BCMA-positive K562-BCMA and RPMI-8226 cells, especially for RPMI-8226 cells endogenously expressing BCMA, while almost no killing effect on BCMA-negative K562 cells (FIG. 11A).

5. Treatment of NOD/SCID Mice Loaded with Peripheral Blood B Lymphocytes RPMI-8226 of Multiple Myeloma RPMI-8226 cells were inoculated into 40 NOD/SCID mice at $8 \times 10^6$/mice, respectively. On Day 12 after subcutaneous inoculation of tumor cells, the average tumor volume was 75 mm$^3$, the mice were randomly divided into 4 groups, and $1 \times 10^7$ CAR T were injected into the tail vein. And cyclophosphamide was intraperitoneally injected before the injection at a doseage of 100 mg/kg for clearing residual T cells in mice in advance. On Day 17 of CAR T injection, the mice were sacrificed by cervical dislocation.

Figures 11B, 12:
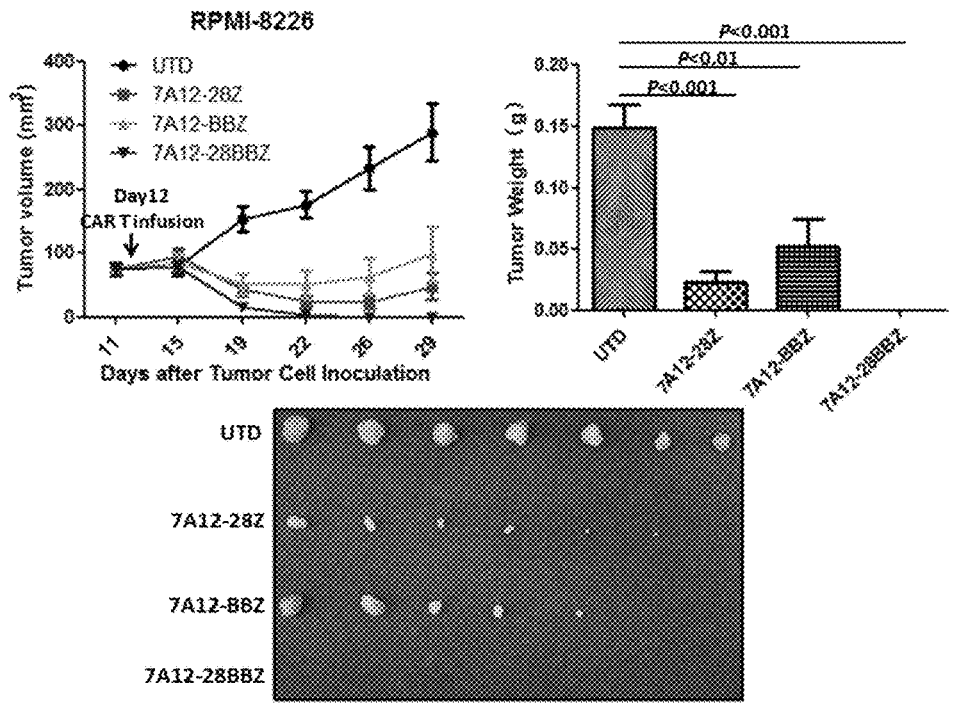
FIG. 11B shows the results of in vivo experiments of BCMA-CAR T in mice.
FIG. 12 compares the heavy chain amino acid sequences of clones 25C2, 25D2 and 23F10, corresponding to SEQ ID NOS: 56, 58, and 21, respectively.

The tumor size of the mice was analyzed. The results are shown in FIG. 11B. Compared with UTD group, the antitumor effects in 7A12-28Z, 7A12-BBZ and 7A12-28BBZ treatment groups were significant, and on Day 17 of CAR T injection, there was 1 case of tumor regression in 7 mice of 7A12-28Z treatment group, 2 cases of tumor regression in 7 mice of 7A12-BBZ treatment group, and 7 cases of tumor regression in 7 mice of 7A12-28BBZ treatment group. The tumor inhibition rates were 7A12-28Z (84.6%), 7A12-BBZ (65.4%) and 7A12-28BBZ (100%), respectively.

Example 10. Modification of Antibody 23F10

In this example, 23F10 was used as a parent antibody, and 23F10 was modified by phage display method. A phage library was constructed based on 23F10 with CDR3 regions of the light and heavy chain being retained, and two phage libraries were constructed by randomizing CDR1 and CDR2 of the light chain or CDR1 and CDR2 of the heavy chain with degenerate primers, respectively. Primer information is as follows:

2.1 Construction of 23F10 Mutant

A template plasmid was firstly constructed based on antibody 23F10 (scFv) (SEQ ID NO: 55). For phage libraries of randomized light chain CDR1 and CDR2, primers LMF and BL1R were used to PCR-amplify fragment 1; primers BL2F and FdR were used to PCR-amplify fragment 2; then fragment 1 and fragment 2 were ligated by bridge-PCR to obtain a full length scFv containing the randomized sequence, and afterwards the full-length fragment was digested with NcoI and NotI and ligated into an identically digested template plasmid by T4 ligase. The plasmid was transduced into TG1 competent cells by electroporation, the storage capacity of which was 1.50E+9. For phage libraries of randomized heavy chain CDR1 and CDR2, primers LMF and BH1R were used to PCR-amplify fragment 3; primers BH2F and FdR were used to PCR-amplify fragment 4; then fragment 3 and fragment 4 were ligated by bridge-PCR to obtain a full length scFv containing the randomized sequence, and afterwards the full-length fragment was digested with NcoI and NotI and ligated into an identically digested template plasmid by T4 ligase. The plasmid was transduced into TG1 competent cells by electroporation, the storage capacity of which was 2.2E+9.

Screening of phage libraries. Referring to the method in Example 3, the initial concentration of antigen BCMA_huFc was 20 nM, and a 5-fold gradient dilution was performed for the next round of screening. Panning was performed for 2-3 cycles to enrich scFv phage clones specifically binding to BCMA_huFc. Positive clones were determined by standard ELISA methods for BCMA_huFc. In ELISA, human Fc fragment was used as an unrelated antigen to verify the specificity of the antibody. A total of 80 ELISA-positive clones were picked and the dissociation constant $K_d$ of the supernatant was determined by biacore after reinduction. Among them, there are two clones, 25C2 and 25D2, the $K_d$ of which is 10 times lower than the parental clone 23F10, as shown in the following table:

| Clone | Dissociation constant $(K_d, S^{-1})$ |
|---|---|
| 23F10 | 3.43E−03 |
| 25C2 | 3.64E−04 |
| 25D2 | 3.74E−04 |

| SEQ ID NO | name | Sequence |
|---|---|---|
| 49 | Primer LMF | CAGGAAACAGCTATGACCATGATTAC |
| 50 | Primer BH1R | TGAGACCCACTCCAGCCCCTTCCCTGGAGCCTGGCGGACCCAMNNM NNMNMNNMNMNNMNNAAAGGTGAATCCGGAGGCTG |
| 51 | Primer BH2F | GGCTGGAGTGGGTCTCANNKATTNNKNNKNNKNNKGGTNNKACAN NKTACGCAGACTCCGTGAAGGG |
| 52 | Primer FdR | GACGTTAGTAAATGAATTTTCTGTATGAGG |
| 53 | Primer BL1R | GATGAGGAGCCTGGGAGCCTGGCCAGGTTTCTGCTGGTACCAMNNT AAMNNMNNMNNMNNMNNMNNCTGACTGGCCCTGCAAGAG |
| 54 | Primer BL2F | CCAGGCTCCCAGGCTCCTCATCNNKNNKNNKNNKNNKAGGGCCACT GGCATCCCAGAC |

The light chains of clones 25C2 and 25D2 were sequenced as being identical to 23F10. In FIG. 12, the heavy chain amino acid sequences of clones 25C2, 25D2 and 23F10 were compared, wherein, compared with the parent antibody 23F10, there are 5 point mutations on the heavy chain in clone 25C2 (SEQ ID NOs: 56, 57 are the amino acid sequence and the nucleotide sequence of 25C2 heavy chain variable region, respectively), and there are 2 point mutations on CDR1, serine to glycine at 31$^{st}$ position and tyrosine to asparagine at 32$^{nd}$ position; there are 2 point mutations on CDR2, serine to asparaginyl at the 54$^{th}$ position and tyrosine to phenylalanine at the 59$^{th}$ position, and there is 1 point mutation in the framework region, serine to glycine at the 30$^{th}$ position. Compared with the parent antibody 23F10, there are 4 point mutations on the heavy chain of Clone 25D2 (SEQ ID NO: 58, 59 are the amino acid sequence and nucleotide sequence of the heavy chain variable region of 25D2, respectively), wherein there are 3 point mutations in CDR2 region, serine to glycine at the 54$^{th}$ position, serine to asparagine at the 57$^{th}$ position and tyrosine to phenylalanine at the 59$^{th}$ position, and there is 1 point mutation in the framework region, serine to arginine at the 30$^{th}$ position.

The sequence of HCDR1 of 25C2 is set forth in SEQ ID NO: 60, and the sequence of HCDR2 of 25C2 is set forth in SEQ ID NO: 61. The sequence of HCDR1 of 25D2 is set forth in SEQ ID NO: 62, and the sequence of HCDR2 of 25D2 is set forth in SEQ ID NO: 63. The nucleotide sequence and amino acid sequence of 25C2 scFv are shown in SEQ ID NO: 64, 65, respectively, and the nucleotide sequence and amino acid sequence of the 25D2 scFv are shown in SEQ ID NO: 66, 67, respectively.

2.2 Expression and Purification of Clone 25C2, 25D2 (scFv_Fc)

According to Example 4, appropriate cleavage sites and protecting bases were introduced upstream to VH, and appropriate cleavage sites and protecting bases were introduced downstream to VL. The PCR product was analyzed by 1% agarose gel electrophoresis, purified and recovered. After digestion, it was ligated into eukaryotic expression vector V152 containing human Fc fragment (purchased from Shanghai Ruijin Biotechnology Co., Ltd.), and transiently transfected into 293F cells by 293Fectin and expressed.

Figure 13A:
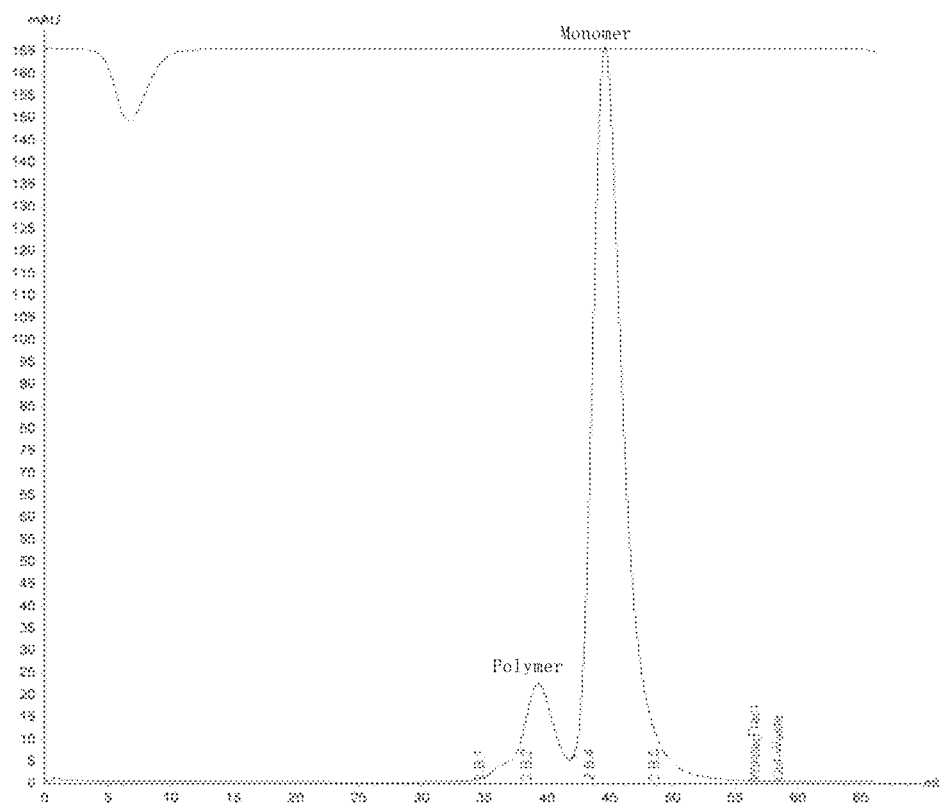
FIG. 13A shows the aggregation of antibody 25C2.
Figure 13B:
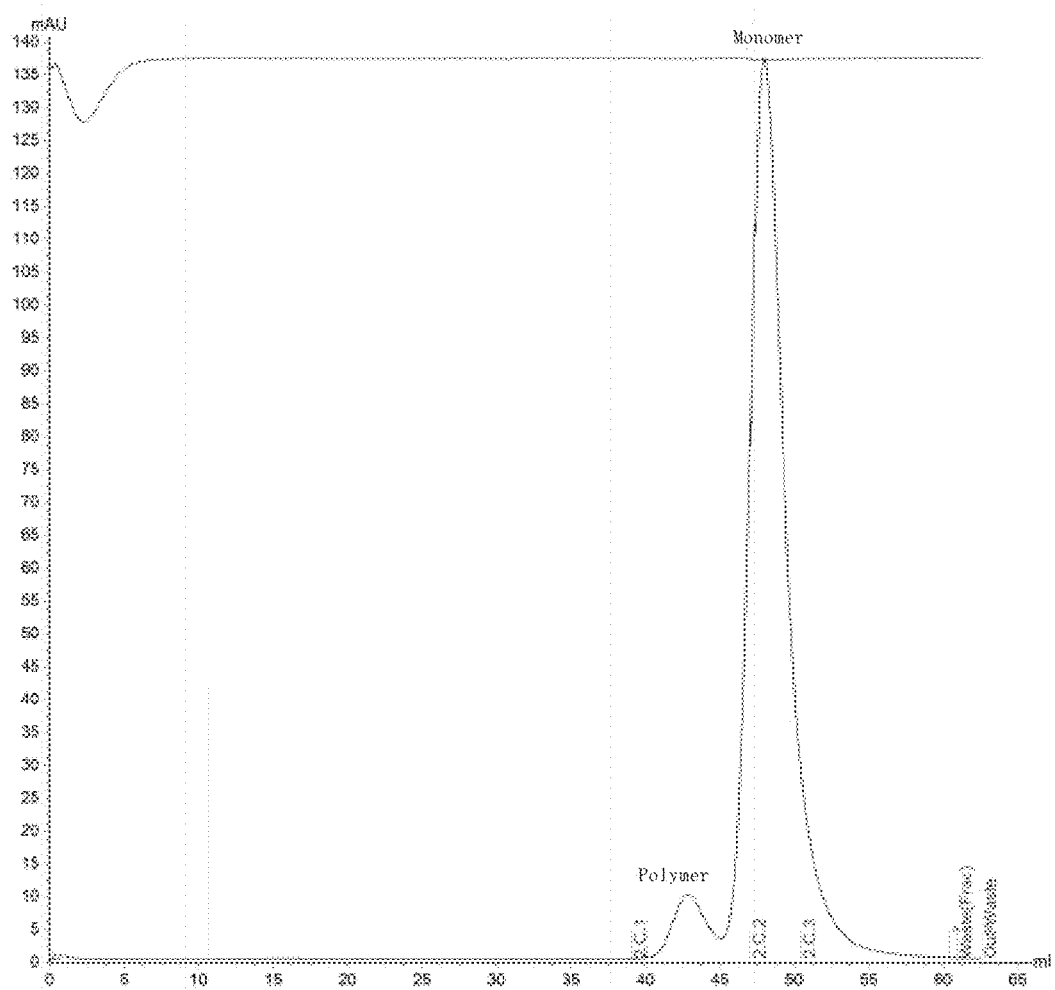
FIG. 13B shows the aggregation of antibody 25D2.
Figure 13C:
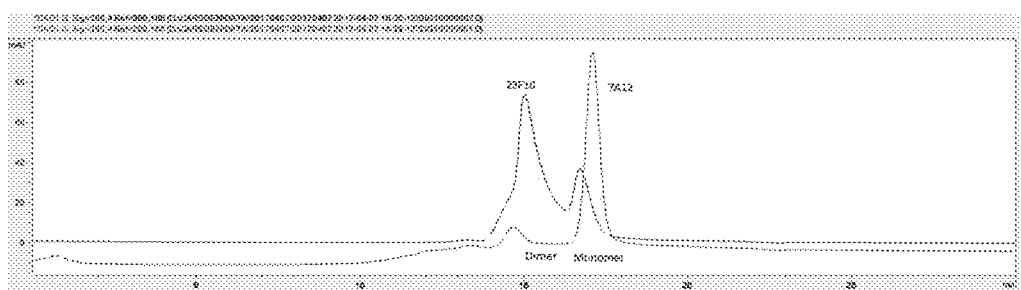
FIG. 13C shows the aggregation of antibodies 23F10 and 7A12.

The aggregation of 25C2 and 25D2 was analyzed by SEC. As shown in FIGS. 13A and 13B, the antibody in a monomer form accounted for 91% and 97%, respectively. Compared with the parent antibody 23F10 (30% monomer rate), the monomer rate was increased by 61% and 67%, respectively, and the aggregation was significantly reduced. After concentration by ultrafiltration, the obtained antibodies were quantitatively and qualitatively analyzed by SDS PAGE. The yields were 80 ug/ml and 60 ug/ml, respectively (yield=weight of final product/transfection volume).

2.3 Binding Characteristics of Clones 25C2, 25D2

Figure 14A:
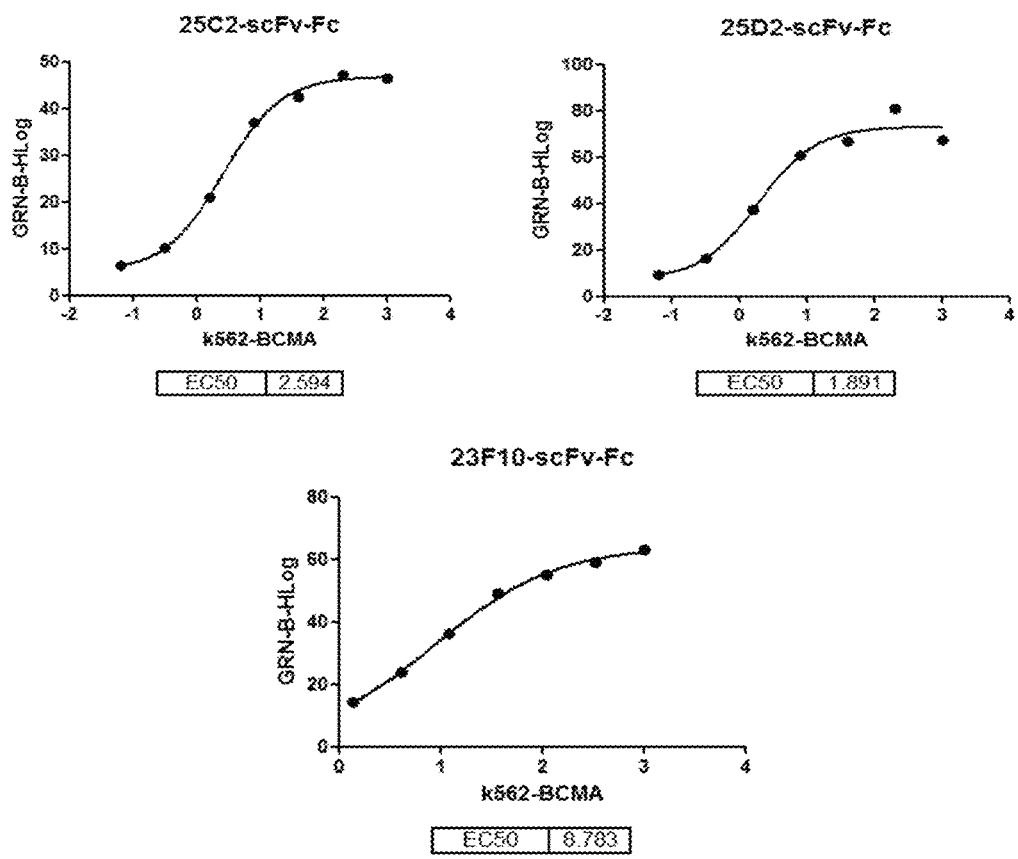
FIG. 14A shows the binding of 25C2 and 25D2 to K562-BCMA and K562 cells.

K562 and K562 cells (K562-BCMA) stably expressing human BCMA were used and harvested, washed with complete growth medium, and plated into U-bottom microtiter plates at about 1 to 5×10$^5$ cells/well. The gradient-diluted scFv_Fc fusion antibody was incubated with K562-BCMA/K562 for 30 minutes on ice, and then incubated with FITC-labeled anti-human Fc as a secondary antibody. After two washing steps, the analysis was performed using a Guava easyCyte™ HT System, and the experimental data was processed using GraphPad Prism to obtain an EC50. FIG. 14 shows the binding of 25C2, 25D2 to K562-BCMA and K562 cells. The results showed that EC50s of two clones, 25C2, 25D2 with improved stability and reduced aggregation binding to K562-BCMA were 2.594 nM and 1.891 nM, respectively, which, compared with 23F10, were increased by 3 to 4 times.

2.5 Determination of Specificity of Clones 25C2, 25D2

The specificity of the antibodies 23F10, 25C2, 25D2 was determined by ELISA.

2 ug/ml recombinant human BCMA_Fc, mouse BCMA_Fc, TACI_huFc (R&D, #174TC), BAFF R (R&D, #1162-BR) were coated on immunoplates at 4° C. overnight. The next day, 300 µl/well of 2% MPBS was added for 2 hours, then 200 nM purified antibody (scFv format) was added and incubated at 37° C. for 1 hour, washed three times with PBST (PBS containing 0.05% Tween-20), and washed three times with PBS. And then 1:4000 diluted HRP-labeled anti-Flag tag antibody (sigma, #A8592-1MG) was added, incubated for 1 hour at 37° C., washed three times with PBST (PBS containing 0.05% Tween-20) and washed three times with PBS. 100 ul/well of TMBS substrate was added and developed for 10-15 minutes. The reaction was quenched by adding 50 ul of 2 M sulfuric acid.

Figure 14B:
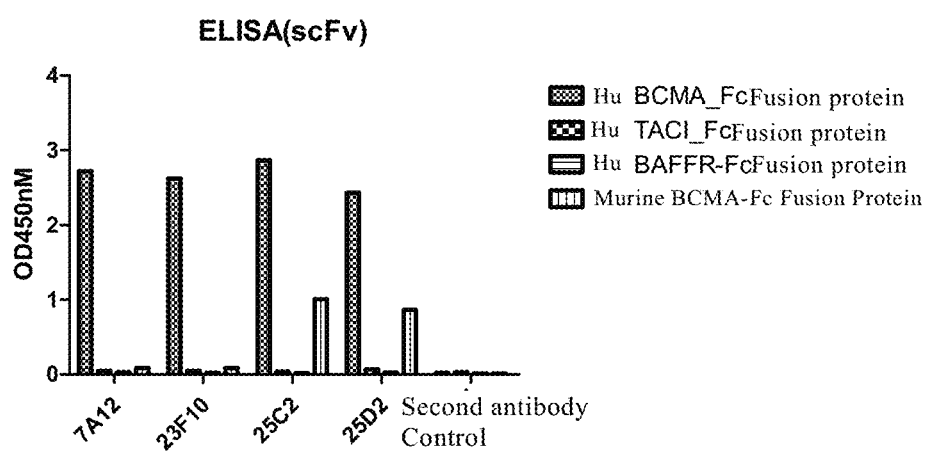
FIG. 14B shows the specificity of antibodies 23F10, 25C2 and 25D2 determined by ELISA assay.

Results are shown in FIG. 14B, wherein antibodies 7A12, 23F10, 25C2, 25D2 specifically bind to human BCMA, and do not bind human TACI and human BAFF R. Among them, the binding of antibodies 25C2, 25D2 to mouse BCMA is weaker.

Example 11. Preparation of 25C2, 25D2 CAR-T Cells

According to the procedure of Example 8, plasmids of chimeric antigen receptor of 25C2, 25D2 were constructed, respectively.

a. Construction of Plasmid of Chimeric Antigen Receptor of 25C2

Lentiviral plasmid PRRLSIN-cPPT.EF-1α-25C2-BBZ expressing the second-generation chimeric antigen receptor of antibody 25C2 was constructed using PRRLSIN-cPPT.EF-1α as a vector. Lentiviral plasmid PRRLSIN-cPPT.EF-1α-25D2-BBZ expressing the second-generation chimeric antigen receptor of antibody 25D2 was constructed using PRRLSIN-cPPT.EF-1α as a vector.

25C2-BBZ sequence consists of CD8α signal peptide (SEQ ID NO: 23), 25C2 scFv (SEQ ID NO: 64), CD8 hinge (SEQ ID NO: 25), transmembrane region (SEQ ID NO: 33), CD137 intracellular signaling domain (SEQ ID NO: 35) and CD3ξ (SEQ ID NO: 31).

25D2-BBZ sequence consists of CD8α signal peptide (SEQ ID NO: 23), 25D2 scFV (SEQ ID NO: 66), CD8 hinge (SEQ ID NO: 25), transmembrane region (SEQ ID NO: 33), CD137 intracellular signaling domain (SEQ ID NO: 35) and CD3ξ (SEQ ID NO: 31).

According to the procedure of Example 9, the plasmids PRRLSIN-cPPT.EF-1α-25C2-BBZ, PRRLSIN-cPPT.EF-1α-25D2-BBZ were subjected to lentiviral packaging, T cell infection and amplification, respectively, to obtain chimeric antigen receptor-modified T cells 25C2-BBZ and 25D2-BBZ.

Example 12. Preparation of CAR-T Cells Expressing Soluble PD1

In this example, CAR-T cells expressing soluble PD1 were prepared using scFv of antibody 7A12. The preparation method is listed as follows:

1. The signal peptide sequence of PD-1 (SEQ ID NO: 68), PD-1 extracellular segment sequence (SEQ ID NO: 69) and the sequence of CH3 (SEQ ID NO: 70) were synthesized and cloned into T Vector to obtain plasmid T-sPD1-Fc.

Using the T-sPD1-Fc plasmid as a template, the upstream primer 5'-acgcgtcctagcgctaccggtcgccaccatgcagatcc-cacaggcgccc-3' (SEQ ID NO: 71) and the downstream primer 5'-ctctcggggctgcccaccatacaccagggtttggaactggc-3' (SEQ ID NO: 72) were used in PCR amplification to obtain sPD1 sequence; and the upstream primer 5'-tatggtgggcagccccgagagccacag-3' (SEQ ID NO: 73), downstream primer 5'-aaaattcaaagtctgtttcactttacccgga-gacagggag-3' (SEQ ID NO: 74) were used in amplification to obtain sPD1-CH3 fragment.

The sPD1-CH3 fragment and the fragment of 7A12-BBZ (SEQ ID NO: 75) were PCR-spliced and amplified to obtain sPD1-CH3-7A12-BBZ, and the sequence of 7A12-BBZ consists of CD8α signal peptide (SEQ ID NO: 23), 7A12 scFv (SEQ ID NO: 47), CD8 hinge (SEQ ID NO: 25), transmembrane region (SEQ ID NO: 33), CD137 intracellular signaling domain (SEQ ID NO: 35) and CD3ξ (SEQ ID) NO: 31).

The above constructed fragment sPD1-CH3-7A12-BBZ has a MluI cleavage site at 5' end and a SalI cleavage site at 3' end, which was double-digested with MluI and SalI and ligated into indentically double-digested PRRLSIN-cPPT.EF-1α vector to obtain a plasmid expressing sPD-1-CH3 protein and a chimeric antigen receptor targeting BCMA.

According to the procedure of Example 9, T cells sPD-1-7A12-BBZ expressing sPD1 and 7A12-BBZ were obtained.

Example 13. In Vitro Cell Killing Experiment

In vitro killing experiments were performed using 25C2-BBZ T cells, 25D2-BBZ T cells, 7A12-BBZ T cells, C11D5.3-BBZ T cells, and sPD-1-7A12-BBZ T cells as effector cells, among which C11D5.3-BBZ (SEQ ID NO: 87) is a second generation CAR prepared by using anti-BCMA mouse anti-C11D5.3 (see CN201580073309.6). Target cells were human myeloma cells NCI-H929 and multiple myeloma peripheral blood B lymphocytes RPMI-8226.

CytoTox 96 non-radioactive cytotoxicity assay kit (Promega) was used according to the instruction of CytoTox 96 non-radioactive cytotoxicity test kit.

Effector cells were inoculated in 96-well plates at a effector target ratio of 3:1, 1:1 or 1:3, and 50 μL of 2×10$^5$/mL NCI-H929 and RPMI-8226 cells were inoculated into the corresponding 96-well plates.

Pentaplicate wells were set for each group, and the plates were incubated in an incubator for 18 h.

The experimental groups and the control groups were set as follows: experimental group: each target cell+T lymphocytes expressing different chimeric antigen receptors; control group 1: maximal release of LDH from target cells; control group 2: spontaneous release of LDH from target cells; Control group 3: spontaneous release of LDH from Effector cells. The calculation formula is: % cytotoxicity= [(experimental group−effector cell spontaneous group−target cell spontaneous group)/(target cell maximum−target cell spontaneous)]*100.

Figure 15:
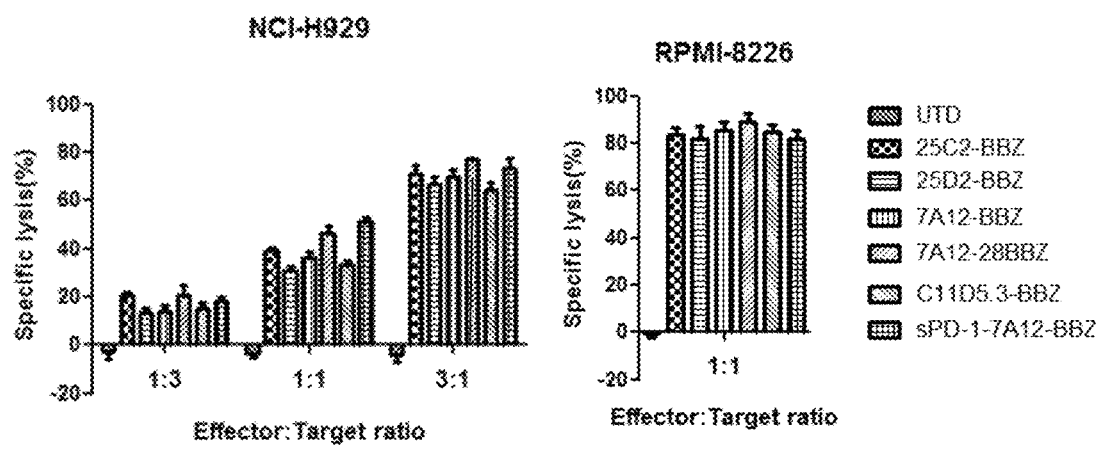
FIG. 15 shows the experiment results of cell killing of 25C2-BBZ, 25D2-BBZ, 7A12-BBZ, C11D5.3-BBZ and sPD-1-7A12-BBZ.

The experimental results of cell killing are shown in FIG. 15.

Example 14. In Vivo Cell Killing Experiment in Mice

8×10$^6$ RPMI-8226 cells were subcutaneously inoculated into the right iliac crest of B-NDG mice, and on Day 18, the average tumor volume was about 243 mm$^3$, thereby obtaining a subcutaneous xenograft model of B-NDG mice loaded with peripheral blood B lymphocytes RPMI-8226 of multiple myeloma.

The mouse subcutaneous xenograft model was divided into 3 groups (4 in each group), and injected with 25C2-BBZ, 25D2-BBZ and untransfected T cells (UTD) at a dose of 5×10$^6$, respectively. The results are shown in the following table. On Day 32 and Day 36 of inoculation of tumor cells, in all 4 mice of the 25C2-BBZ and 25D2-BBZ treatment groups, tumors regressed.

| | Cancer Free Days after tumor cell inoculation | | | | | |
|---|---|---|---|---|---|---|
| CAR T Dose: 5 × 10$^6$ | Day 25 | Day 29 | Day 32 | Day 36 | Day 39 | Day 42 |
| UTD | 0/4 | 0/4 | 0/4 | 0/4 | 0/4 | 0/4 |
| 25C2-BBZ | 1/4 | 2/4 | 4/4 | 4/4 | 4/4 | 4/4 |
| 25D2-BBZ | 0/4 | 1/4 | 3/4 | 4/4 | 4/4 | 4/4 |

Figure 16:
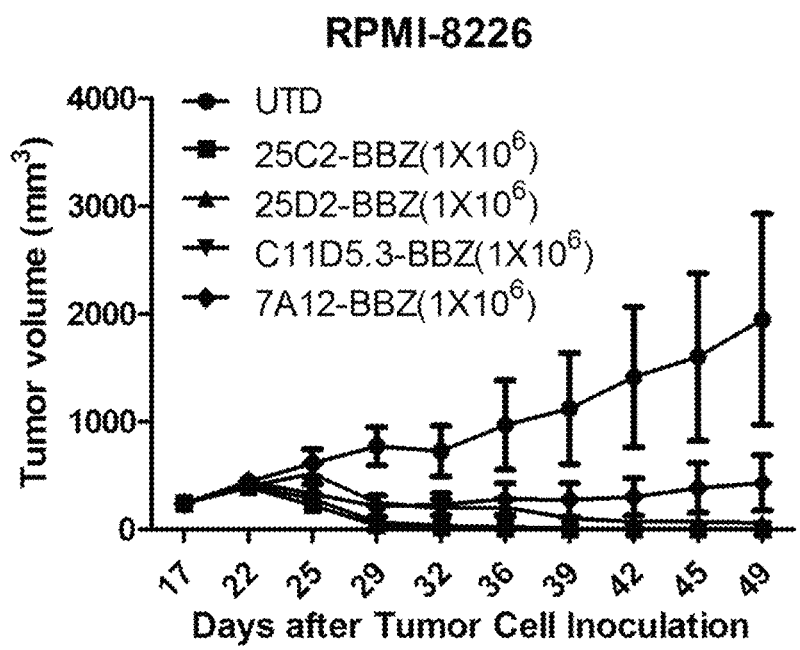
FIG. 16 shows the results of subcutaneous xenografts of 25C2-BBZ, 25D2-BBZ, C11D5.3-BBZ, 7A12-BBZ.

The mouse subcutaneous xenograft model was divided into 3 groups (4 in each group), and injected with 25C2-BBZ, 25D2-BBZ, C11D5.3-BBZ, 7A12-BBZ and untransfected T cells (UTD) at an injection dose of 1×10$^6$ CAR T. The tumor regression was shown in the following table and FIG. 16.

| | Cancer Free Days after tumor cell inoculation | | | | | | |
|---|---|---|---|---|---|---|---|
| CAR T Dose: 1 × 10$^6$ | Day 29 | Day 32 | Day 36 | Day 39 | Day 42 | Day 45 | Day 49 |
| UTD | 0/4 | 0/4 | 0/4 | 0/4 | 0/4 | 0/4 | 0/4 |
| 25C2-BBZ | 1/4 | 2/4 | 3/4 | 4/4 | 4/4 | 4/4 | 4/4 |
| 25D2-BBZ | 0/4 | 0/4 | 1/4 | 1/4 | 1/4 | 1/4 | 2/4 |
| C11D5.3-BBZ | 0/4 | 1/4 | 1/4 | 2/4 | 3/4 | 3/4 | 3/4 |
| 7A12-BBZ | 0/4 | 0/4 | 0/4 | 1/4 | 2/4 | 2/4 | 2/4 |

All documents mentioned in the present application are hereby incorporated by reference in their entireties as if each document is separately cited as a reference. In addition, it is to be understood that various modifications and changes may be made by a skilled person in the art, after reading the above teachings of the present invention, and the equivalent forms also fall within the scope defined by the claims appended hereto.

The invention claimed is:

1. An antibody that binds B cell maturation antigen (BCMA), wherein the antibody comprises a light chain variable region (VL) comprising light chain complementarity determining region (LCDR) 1, 2, and 3 and comprises a heavy chain variable region (VH) comprising heavy chain complementarity determining region (HCDR) 1, 2, and 3; wherein the antibody is selected from the group consisting of:
   (a) an antibody comprising HCDR1 as shown in SEQ ID NO: 1, HCDR2 as shown in SEQ ID NO: 2, HCDR3 as shown in SEQ ID NO: 3, LCDR1 as shown in SEQ ID NO: 6, LCDR2 as shown in SEQ ID NO: 7, and LCDR3 as shown in SEQ ID NO: 8;
   (b) an antibody comprising HCDR1 as shown in SEQ ID NO: 1, HCDR2 as shown in SEQ ID NO: 2, HCDR3 as shown in SEQ ID NO: 4, LCDR1 as shown in SEQ ID NO: 6, LCDR2 as shown in SEQ ID NO: 7, and LCDR3 as shown in SEQ ID NO: 9;
   (c) an antibody comprising HCDR1 as shown in SEQ ID NO: 1, HCDR2 as shown in SEQ ID NO: 2, HCDR3 as shown in SEQ ID NO: 5, LCDR1 as shown in SEQ ID NO: 6, LCDR2 as shown in SEQ ID NO: 7, and LCDR3 as shown in SEQ ID NO: 10;
   (d) an antibody comprising HCDR1 as shown in SEQ ID NO: 60, HCDR2 as shown in SEQ ID NO: 61, HCDR3 as shown in SEQ ID NO: 5, LCDR1 as shown in SEQ ID NO: 6, LCDR2 as shown in SEQ ID NO: 7, and LCDR3 as shown in SEQ ID NO: 10; and
   (e) an antibody comprising HCDR1 as shown in SEQ ID NO: 62, HCDR2 as shown in SEQ ID NO: 63, HCDR3 as shown in SEQ ID NO: 5, LCDR1 as shown in SEQ ID NO: 6, LCDR2 as shown in SEQ ID NO: 7, and LCDR3 as shown in SEQ ID NO: 10.

2. The antibody of claim 1, wherein the antibody is selected from the group consisting of:
   (a) an antibody comprising a heavy chain variable region that has the amino acid sequence shown in SEQ ID NO: 13 and a light chain variable region that has the amino acid sequence shown in SEQ ID NO: 11;
   (b) an antibody comprising a heavy chain variable region that has the amino acid sequence shown in SEQ ID NO: 17 and a light chain variable region that has the amino acid sequence shown in SEQ ID NO: 15;
   (c) an antibody comprising a heavy chain variable region that has the amino acid sequence shown in SEQ ID NO: 21 and a light chain variable region that has the amino acid sequence shown in SEQ ID NO: 19;
   (d) an antibody comprising a heavy chain variable region that has the amino acid sequence shown in SEQ ID NO: 56 and a light chain variable region that has the amino acid sequence shown in SEQ ID NO: 19; and
   (e) an antibody comprising a heavy chain variable region that has the amino acid sequence shown in SEQ ID NO: 58 and a light chain variable region that has the amino acid sequence shown in SEQ ID NO: 19.

3. A pharmaceutical composition comprising an antibody of claim 1 and a pharmaceutically acceptable carrier.

4. A nucleic acid encoding the antibody of claim 1.

5. An expression vector comprising the nucleic acid of claim 4.

6. A host cell comprising the expression vector of claim 5.

7. A multifunctional immunoconjugate, comprising an antibody of claim 1 and a functional molecule linked thereto, wherein the functional molecule is selected from the group consisting of a molecule that targets a tumor surface marker, a molecule that inhibits tumors, a molecule that targets a surface marker of an immune cell, and a detectable label; wherein the multifunctional immunoconjugate optionally includes a linker peptide between the antibody and functional molecule.

8. The multifunctional immunoconjugate of claim 7, wherein the molecule that inhibits tumors is an antitumor cytokine or an antitumor toxin.

9. The multifuctional immunoconjugate of claim 7, wherein the molecule that targets a surface marker of an immune cell is an antibody that binds to a surface marker of an immune cell.

10. A pharmaceutical composition comprising a multifunctional immunoconjugate of claim 7 and a pharmaceutically acceptable carrier.

11. A B cell maturation antigen (BCMA)-targeting chimeric antigen receptor (CAR) that comprises an extracellular domain, a hinge domain, a transmembrane domain, and an intracellular signal domain sequentially linked, wherein the extracellular domain comprises a BCMA-binding antibody of claim 1.

12. The chimeric antigen receptor of claim 11, wherein the intracellular signal domain further comprises one or more co-stimulatory signal domains.

13. The chimeric antigen receptor of claim 12, wherein the transmembrane domain is selected from the group consisting of alpha, beta, zeta chain of TCR, or the transmembrane domain is a transmembrane region selected from the group consisting of CD3ε, CD3ζ, CD4, CD5, CD8α, CD9, CD16, CD22, CD27, CD28, CD33, CD37, CD45, CD64, CD80, CD86, CD134, CD137, CD152, CD154 and PD1; and/or the co-stimulatory signal domain is selected from the group consisting of an intracellular signal region of CARD11, CD2, CD7, CD27, CD28, CD30, CD40, CD54, CD83, OX40, CD137, CD134, CD150, CD152, CD223, CD270, PD-L2, PD-L1, CD278, DAP10, LAT, NKD2C, SP76, TRIM, FcεRIγ, MyD88 and 41BBL.

14. The chimeric antigen receptor of claim 13, wherein the transmembrane domain is the transmembrane region of CD8 or CD28, and/or the co-stimulatory signal domain is the intracellular signal domain of CD137 or CD28.

15. The chimeric antigen receptor of claim 11, wherein the extracellular domain is a scFv antibody comprising a heavy chain variable region that has HCDR1 as shown in SEQ ID NO: 60, HCDR2 as shown in SEQ ID NO: 61 and HCDR3 as shown in SEQ ID NO: 5 and a light chain variable region that has LCDR1 as shown in SEQ ID NO: 6, LCDR2 as shown in SEQ ID NO: 7 and LCDR3 as shown in SEQ ID NO: 10.

16. A genetically modified immune cell which expresses the chimeric antigen receptor of claim 11.

17. The genetically modified immune cell of claim 16, wherein the genetically modified immune cell further expresses a sequence that encodes a cytokine selected from IL-12, IL-15, IL-21, and type I interferon; another chimeric antigen receptor; a chemokine receptor; an siRNA that reduces PD-1 expression; a protein that blocks PD-L1; a TCR; or a sequence that is a safety switch.

18. A genetically modified T cell which expresses the chimeric antigen receptor of claim 11.

19. A pharmaceutical composition comprising genetically modified immune cells of claim 16.

20. A B cell maturation antigen (BCMA)-targeting chimeric antigen receptor (CAR), wherein the chimeric antigen receptor is selected from the group consisting of:
(a) a chimeric antigen receptor that has an extracellular domain as shown in SEQ ID NO: 64, a CD8 hinge domain as shown in SEQ ID NO: 25, a transmembrane region as shown in SEQ ID NO: 33, a CD137 intracellular signaling domain as shown in SEQ ID NO: 35, and a CD3ξ primary signal domain as shown in SEQ ID NO: 31;
(b) a chimeric antigen receptor that has an extracellular domain as shown in SEQ ID NO: 66, a CD8 hinge domain as shown in SEQ ID NO: 25, a transmembrane region as shown in SEQ ID NO: 33, a CD137 intracellular signaling domain as shown in SEQ ID NO: 35, and a CD3ξ primary signal domain as shown in SEQ ID NO: 31;
(c) a chimeric antigen receptor that has an extracellular domain as shown in SEQ ID NO: 47, a CD8 hinge domain as shown in SEQ ID NO: 25, a transmembrane region as shown in SEQ ID NO: 33, a CD137 intracellular signaling domain as shown in SEQ ID NO: 35, and a CD3ξ primary signal domain as shown in SEQ ID NO: 31;
(d) a chimeric antigen receptor that has CD8α signal peptide as shown in SEQ ID NO: 23, 7A12 scFv as shown in SEQ ID NO: 47, CD8 hinge as shown in SEQ ID NO: 25, CD28 transmembrane region as shown in SEQ ID NO: 27, intracellular signaling domain as shown in SEQ ID NO: 29 and intracellular segment CD3ξ of CD3 as shown in SEQ ID NO: 31;
(e) a chimeric antigen receptor that has CD8α signal peptide as shown in SEQ ID NO: 23, 7A12 scFv as shown in SEQ ID NO: 47, CD8 hinge as shown in SEQ ID NO: 25, transmembrane region as shown in SEQ ID NO: 33, CD137 intracellular signaling domain as shown in SEQ ID NO: 35 and CD3ξ as shown in SEQ ID NO: 31;
(f) a chimeric antigen receptor that has CD8α signal peptide as shown in SEQ ID NO: 23, 7A12-scFv as shown in SEQ ID NO: 47, CD8 hinge as shown in SEQ ID NO: 25, CD28 transmembrane region as shown in SEQ ID NO: 27, intracellular segment as shown in SEQ ID NO: 29, CD137 intracellular signaling domain as shown in SEQ ID NO: 35 and CD3ξ as shown in SEQ ID NO: 31;
(g) a chimeric antigen receptor that has CD8α signal peptide as shown in SEQ ID NO: 23, 7G2 scFv as shown in SEQ ID NO: 48, CD8 hinge as shown in SEQ ID NO: 25, CD28 transmembrane region as shown in SEQ ID NO: 27, intracellular signaling domain as shown in SEQ ID NO: 29 and intracellular segment CD3ξ of CD3 as shown in SEQ ID NO: 31;
(h) a chimeric antigen receptor that has CD8α signal peptide as shown in SEQ ID NO: 23, 7G2 scFV as shown in SEQ ID NO: 48, CD8 hinge as shown in SEQ ID NO: 25, transmembrane region as shown in SEQ ID NO: 33, CD137 intracellular signaling domain as shown in SEQ ID NO: 35 and CD3ξ as shown in SEQ ID NO: 31; and
(i) a chimeric antigen receptor that CD8α signal peptide as shown in SEQ ID NO: 23, 7G2-scFv as shown in SEQ ID NO: 48, CD8 hinge as shown in SEQ ID NO: 25, CD28 transmembrane region as shown in SEQ ID NO: 27, intracellular segment as shown in SEQ ID NO: 29, CD137 intracellular signaling domain as shown in SEQ ID NO: 35 and CD3ξ as shown in SEQ ID NO: 31.

21. A genetically modified T cell which expresses a BCMA-targeting chimeric antigen receptor of claim 20.

22. A pharmaceutical composition comprising genetically modified T cells of claim 21.

23. A method of killing BCMA-expressing tumor cells comprising contacting the tumor cells with genetically modified T cells of claim 21.

24. The method of claim 23, wherein the tumor cells are multiple myeloma cells.

* * * * *